US011254720B2

(12) United States Patent
Cohen et al.

(10) Patent No.: US 11,254,720 B2
(45) Date of Patent: Feb. 22, 2022

(54) METHODS AND SYSTEMS FOR DESIGNING AND/OR CHARACTERIZING SOLUBLE LIPIDATED LIGAND AGENTS

(71) Applicants: Tufts Medical Center, Boston, MA (US); Trustees of Tufts College, Medford, MA (US); On Target Therapeutics LLC, Wellesley, MA (US)

(72) Inventors: Charles Cohen, Weston, MA (US); Krishna Kumar, Cambridge, MA (US); Jamie Raudensky Doyle, Newton, MA (US); Alan S. Kopin, Wellesley, MA (US)

(73) Assignees: On Target Therapeutics LLC, Wellesley, MA (US); Trustees of Tufts College, Medford, MA (US); Tufts Medical Center, Boston, MA (US)

( * ) Notice: Subject to any disclaimer, the term of this patent is extended or adjusted under 35 U.S.C. 154(b) by 187 days.

(21) Appl. No.: 16/245,472

(22) Filed: Jan. 11, 2019

(65) Prior Publication Data

US 2019/0135882 A1  May 9, 2019

Related U.S. Application Data

(62) Division of application No. 14/783,489, filed as application No. PCT/US2014/026662 on Mar. 13, 2014.

(60) Provisional application No. 61/813,835, filed on Apr. 19, 2013, provisional application No. 61/811,249, filed on Apr. 12, 2013.

(51) Int. Cl.
| | |
|---|---|
| *A61K 31/04* | (2006.01) |
| *C07K 7/06* | (2006.01) |
| *C07K 14/47* | (2006.01) |
| *A61K 47/54* | (2017.01) |
| *G01N 33/92* | (2006.01) |
| *C07K 7/08* | (2006.01) |
| *G01N 33/50* | (2006.01) |
| *A61K 38/00* | (2006.01) |

(52) U.S. Cl.
CPC ........ *C07K 14/4703* (2013.01); *A61K 47/543* (2017.08); *C07K 7/06* (2013.01); *C07K 7/08* (2013.01); *G01N 33/5023* (2013.01); *G01N 33/92* (2013.01); *A61K 38/00* (2013.01); *G01N 2405/00* (2013.01); *G01N 2440/10* (2013.01)

(58) Field of Classification Search
None
See application file for complete search history.

(56) References Cited

U.S. PATENT DOCUMENTS

| | | | |
|---|---|---|---|
| 5,200,473 A | 4/1993 | Jeanneret-Gris | |
| 5,284,656 A | 2/1994 | Platz et al. | |
| 5,451,569 A | 9/1995 | Wong et al. | |
| 6,416,738 B1 | 7/2002 | Theodore | |
| 7,169,892 B2 * | 1/2007 | Atsushi | ............... A61K 9/1271 435/176 |
| 9,545,452 B2 * | 1/2017 | Wang | ..................... A61P 19/08 |
| 10,233,219 B2 | 3/2019 | Cohen et al. | |
| 2002/0086020 A1 | 7/2002 | Lee | |
| 2004/0197314 A1 | 10/2004 | Delcarye | |
| 2006/0263336 A1 * | 11/2006 | Caplan | ................. C12N 5/0655 424/93.7 |
| 2008/0020942 A1 | 1/2008 | Raines | |
| 2009/0238808 A1 | 9/2009 | Drewes | |
| 2010/0260681 A1 | 10/2010 | Brennan | |
| 2012/0172235 A1 | 7/2012 | Winter | |
| 2012/0245229 A1 * | 9/2012 | Ji | ......................... A61K 31/202 514/560 |
| 2013/0004592 A1 | 1/2013 | Wu | |
| 2014/0349943 A1 | 11/2014 | Gadek | |
| 2016/0052982 A1 | 2/2016 | Cohen et al. | |
| 2019/0022168 A1 | 1/2019 | Cohen et al. | |

FOREIGN PATENT DOCUMENTS

| | | |
|---|---|---|
| JP | 2010-229093 | 10/2010 |
| WO | WO 2005/121755 A1 | 12/2005 |

OTHER PUBLICATIONS

Missirlis, D., etal Linker chemistry determines secondary structure of p5314-29 in peptide amphiphile micelles. Bioconjugate Chemistry (21) 465-475 (Year: 2010).*
Beutler, B. Innate Immunity: an overview. Molecular immunology. 40. 845-859 (Year: 2004).*
Janeway, C. et al. Principles of Innate and Adaptive immunity. Immunobiology: The Immune System in Health and Disease. 5th edition. New York: Garland Science; 2001 (Year: 2001).*
Fahy, J. Eosinophilic and Neutrophilic Inflammation in Asthma. Proceedings of the American Thoracic Society, vol. 6. pp. 256-259, 2009 (Year: 2009).*

(Continued)

*Primary Examiner* — Joanne Hama
*Assistant Examiner* — Jon M Lockard
(74) *Attorney, Agent, or Firm* — Cooley LLP; Ivor Elrifi; Matthew Pavao

(57) ABSTRACT

The present application provides methods for preparing soluble lipidated ligand agents comprising a ligand entity and a lipid entity, and in some embodiments, provides relevant parameters of each of these components, thereby enabling appropriate selection of components to assemble active agents for any given target of interest.

5 Claims, 13 Drawing Sheets

Specification includes a Sequence Listing.

(56) References Cited

OTHER PUBLICATIONS

Shimamura, K., et al. Identification of a stable chemerin analog with potent activity toward ChemR23. Peptides (30) 1529-1538 (Year: 2009).*
Song, S., et al. Novel peptide ligand directs liposomes toward EGF-R high-expressing cancer cells in vitro and in vivo. The FASEB Journal. 23, pp. 1396-1404, 2009 (Year: 2009).*
Guan, X. and Fierke, C. Understanding protein palmitoylation: Biological significance and enzymology. Sci China Chem. 54(12) 1888-1897 Dec. 2011 (Year: 2011).*
Hein, C., et al. Click Chemistry, a powerful tool for pharmaceutical sciences. Pharmaceutical Research. 25(10) pp. 2216-2230, Oct. 2008 (Year: 2008).*
Chan, A., et al. Modification of N-terminal a-amino groups of peptides and proteins using ketenes. Journal of the American Chemical Society. 134, pp. 2589-2598, Jan. 30, 2012 (Year: 2012).*
Bentley, R. Chirality in Biology. Encyclopedia of Molecular Cell Biology and Molecular Medicine, 2nd Edition. 2004 (Year: 2004).*
Pachynski, R., et al. The chemoattractant chemerin suppresses melanoma by recruiting natural killer cell antitumor defenses. Journal of Experimental Medicine. 209(8) pp. 1427-1435, Jul. 30, 2012 (Year: 2012).*
Amrizas et al. "Treatment Options for Dry Eye Disease", US Pharmacist, 2010, vol. 35, No. 4, p. 34-41.
Doyle J. R. et al. "Development of a Membrane-anchored Chemerin Receptor Agonist as a Novel Modulator of Allergic Airway Inflammation and Neuropathic Pain", Journal of Biological Chemistry, 2014, vol. 289, No. 19, p. 13385-13396.
Hamrah et al. "Alterations in Corneal Stromal Dendritic Cell Phenotype and Distribution in Inflammation", Arch Ophthalmol, 2003, vol. 121, 10 pages in total.
Katsuda et al. "A Small Molecule That Represses Translation of G-Quadruplex-Containing mRNA", J. Am. Chem. Soc. 2016, vol. 138, p. 9037-9040.
Adjei et al., "Pulmonary Delivery of Peptide Drugs: Effect of Particle Size on Bioavailability of Leuprolide Acetate in Healthy Male Volunteers", Pharm Res 7:565-569 (1990).
Al-Fulaij et al., Pharmacological analysis of human D1 and D2 dopamine receptor missense variants, 2008, J. Mol. Neurosci, 34:211-223.
Bennett and Xie, "A peripheral mononeuropathy in rat that produces disorders of pain sensation like those seen in man", 1988, Pain, 33: 87-107.
Best "Click Chemistry and Bioorthogonal Reactions: Unprecedented Selectivity in the Labeling of Biological Molecules", Biochemistry 2009, vol. 48, p. 6571-6584.
Braquet et al., "Effect of Endothelin-1 on Blood Pressure and Bronchopulmonary System of the Guinea Pig", J Cardiovasc Pharmacol 13(suppl. 5):143-146 (1989).
Brunsveld et al. "Membrane binding of lipidated Ras peptides and proteins—The structural point of view", Biochimica et Biophysica Acta 1788, 2009, p. 273-288.
Chamberlain et al., "Targeted delivery of Doxorubicin to mitochondria", 2013, ACS Chem. Biol., 8: 1389-1395.
Chen, I. et al. "Site-specific labeling of cell surface proteins with biophysical probes using biotin ligase", Nature Methods, 2005, 2, 99-104.
Cheng et al., "Luciferase reporter assay system for deciphering GPCR pathways", 2010, Curr Chem Genomics, 4:84-91.
Codelli, et al. "Second-Generation Difluorinated Cyclooctynes for Copper-Free Click Chemistry", J. Am. Chem. Soc. 2008, 130, p. 11486-11493.
Conklin et al., "Substitution of three amino acids switches receptor specificity of Gq alpha to that of Gi alpha", 1993, Nature, 363: 274-276.
Cuttitta et al., "Peptide amidation: signature of bioactivity", 1993, Anatomical Record 236:87-93, 87-93.

Dafik, L. et al. "Fluorinated Lipid Constructs Permit Facile Passage of Molecular Cargo into Living Cells", J. Am. Chem. Soc., 2009, 131, 12091-12093.
Debs et al., "Lung-specific delivery of cytokines induces sustained pulmonary and systemic immunomodulation in rats", 1988, J Immunol 140:3482-3488.
Edwards and Price, "Role of Physiochemical Properties and Ligand Lipophilicity Efficiency in Addressing Drug Safety Risks", Annual Reports in Medicinal Chemistry, 2010, 45:380-391.
Eipper et al., "The biosynthesis of neuropeptides: peptide alpha-amidation", 1992, Annu Rev Neurosci15:57- 85.
Fan et al., "Using luciferase assays to study G protein-coupled receptor pathways and screen for GPCR modulators", 2005, Cell notes, vol. 13, p. 5-7.
Flatters and Bennett, "Ethosuximide reverses paclitaxel- and vincristine-induced painful peripheral neuropathy", 2004, Pain, 109:150-161.
Fortin et al., "Discovery of Dual-Action Membrane-Anchored Modulators of Incretin Receptors", PLoS One 2011, 6, e24693, 13 pages.
Fortin et al., "Membrane-Tethered Ligands are Effective Probes for Exploring Class B1 G Protein-Coupled Receptor Function", Proc. Natl. Acad Sci., 2009, 106: 8049-8054.
Fortin et al., "The µ-opioid receptor variant N190K is unresponsive to peptide agonists yet can be rescued by small-molecule drugs", 2010, Mol. Pharmacol, 78: 837-845.
Gautier, A. et al. "An Engineered Protein Tag for Multiprotein Labeling in Living Cells", Chem. & Biol. 2008, 15, 128-136.
Gill, SC and Von Hippel, "Calculation of protein extinction coefficients from amino acid sequence data", 1989, Analytical Biochem, 182: 319-326.
Gilmore J. et al. "N-Terminal Protein Modification through a Biomimetic Transamination Reaction", Angew. Chem. Int. Ed. 2006, 45, 5307-5311.
Hang HC, "Exploring protein lipidation with chemical biology", 2011, Chem. Rev., vol. 111: 6341-6358.
Harwood et al., "Membrane Tethered Bursicon Constructs as Heterodimeric Modulators of the *Drosophila* G Protein-Coupled Receptor Rickets", Mol. Pharm., 2013, 83:814-821.
Hubbard et al., "Anti-Neutrophil-Elastase Defenses of the Lower Respiratory Tract in a 1-Antitrypsin Deficiency Directly Augmented with an Aerosol of α 1-Antitrypsin", Annal Int Med 3:206-212 (1989).
Jewett et al. "Rapid Cu-Free Click Chemistry with Readily Synthesized Biarylazacyclooctynones", J. Am. Chem. Soc. 2010, 132, p. 3688-3690.
Kolb, H.C. et al. "Click Chemistry: Diverse Chemical Function from a Few Good Reactions", Angew. Chem. Int. Ed.2001, 40, p. 2004-2021.
Kopin et al., "Identification of a series of CCK-2 receptor nonpeptide agonists: sensitivity to stereochemistry and a receptor point mutation", 2003, Proc Natl Acad Sci USA, 100: 5525-5530.
Lagerstrom and Schioth, "Structural Diversity of G Protein-Coupled Receptors and Significance for Drug Discovery", 2008, Nat Rev Drug Discov, 7:339-357.
Langer R, "New Methods of Drug Delivery", Science 249:1527-33 (1990).
Lee et al., "The human brain cholecystokinin-B/gastrin receptor. Cloning and characterization", 1993, J Biol Chem268:8164-8169.
Lipinski CA, "Lead- and Drug-Like Compounds: The Rule of Five Revolution", 2004, Drug Discovery Today, 1(4):337-341.
Los, G.V. "HaloTag: A Novel Protein Labeling Technology for Cell Imaging and Protein Analysis", ACS Chem. Biol. 2008, 3, p. 373-382.
"Medical Definition of Peptide", MedicineNet.com, 2017, 4 pages. http://www.medicinenet.com/script/main/art.asp?articlekey=24643, downloaded Mar. 14, 2017.
Meier, J. L.et al. "Synthesis and Evaluation of Bioorthogonal Pantetheine Analogues for in Vivo Protein Modification", J. Am. Chem. Soc. 2006, 128, p. 12174-12184.
Nadolski and Linder, "Protein lipidation", 2007, FEBS Journal, 274: 5202-5210.
Ning et. al. "Visualizing Metabolically Labeled Glycoconjugates of Living Cells by Copper-Free and Fast Huisgen Cycloadditions", Angew Chem Int Ed, 2008, 47, p. 2253-2255.

(56) References Cited

OTHER PUBLICATIONS

Oeswein et al., "Aerosolization of Proteins Pharmaceuticals", Proceedings of Symposium on Respiratory Drug Delivery II, 1990, Keystone, Colorado.
Overington et al., "How Many Druggable Targets Are There?" 2006, Nat Rev Drug Discov, 5:993-996.
Pap et al., "Peptide-based targeting of fluorophores to organelles in living cells", 2001, Exp. Cell Res., 265: 288-293.
Pennington, M.W., "HF cleavage and deprotection procedures for peptides synthesized using a Boc/Bzl strategy", 1994, Methods in Mol. Biol., 35: 319-326.
Pisegna et al., "Molecular cloning, functional expression, and chromosomal localization of the human cholecystokinin type A receptor", 1994, Ann N Y Acad Sci713:338-342.
Popp, M. W. et al. "Sortagging: a versatile method for protein labeling", Nat. Chem. Biol. 2007, 3, 707-708.
Rask-Andersen et al., "The Druggable Genome: Evaluation of Drug Targets in Clinical Trials Suggests Major Shifts in Molecular Class and Indication", 2013, Annu Rev Pharmacol Toxicol, 54:9-26.
Rostovtsev, V. V. et al. "A Stepwise Huisgen Cycloaddition Process: Copper(I)-Catalyzed Regioselective 'Ligation' of Azides and Terminal Alkynes", Angew. Chem, Int. Ed. 2002, 41, p. 2596-2599.
Sawhney H S et al. "Bioerodible Hydrogels Based on Photopolymerized Poly(ethylene glycol)-co-poly(α-hydroxy acid) Diacrylate Macromers ", (1993) Macromolecules 26:581-87.
Schnolzer et al., "In situ neutralization in Boc-chemistry solid phase peptide synthesis. Rapid, high yield assembly of difficult sequences", 1992, International journal of peptide and protein research 40:180-193.
Schuy S. et al. "Structure and Thermotropic phase Behavior of Fluorinated Phospholipid Bilayers: A combined Attenuated Total Reflection FTIR Spectroscopy and Imaging Ellipsometry Study", J. Phsy. Chem. B, 2008, 112, 8250-8256.
Seo et al. "Docosahexaenoic acid selectively inhibits plasma membrane targeting of lipidated proteins", FASEB Journal, 2006, vol. 20, p. 770-772.
Shimamura, Ken, et al. "Identification of a stable chemerin analog with potent activity toward ChemR23" Peptides 30 (2009); 1529-1538.
Sjödin et al., "Radioreceptor assay for formulations of salmon calcitonin", International Journal of Pharmaceutics 63:135-142 (1990).
Sletten and Bertozzi, "Bioorthoganal Chemistry: Fishing for Selectivity in a Sea of Functionality", 2009, Angewandte Chemie International Edition, 48(38): 6974-6998.
Smith et al., "Pulmonary Deposition and Clearance of Aerosolized Alpha-I-Proteinase Inhibitor Administered to Dogs and to Sheep", 1989, J Clin Invest 84:1145-1154.
Stallaert et al., Impedance Responses Reveal β2-Adrenergic Pluridimensionality and Allow Classification of Ligands with 2012, PLoS One, 7(1):e29420.
Thirumurugan et al., "Click Chemistry for Drug Developmei Applications", Chem, Rev., 2013, 113:4905-4979.
Tomoe, C. W. et al. "Peptidotriazoles on Solid Phase: [1,2,3]-Triazoles by Regiospecific Copper(I)-Catalyzed 1,3-Dipolar Cycloadditions of Terminal Alkynes to Asizes", J. Org. Chem. 2002, 67, 3057-3064.
Triola G. "the Protein Lipidation and its Analysis", Journal of Glycomics & Lipodomics, 2011, s2, 14 pages.
Valko K, "Application of High-Performance Liquid Chromatography Based Measurements of Lipophilicity to Model Biological Distribution", 2004, J. Chromatography, 1037:(1-2): 299-310.
Wang, Q. et al. "Bioconjugation by Copper(I)-Catalyzed Azide-Alkyne [3 + 2] Cycloaddition", J. Am. Chem. Soc.2003, 125, 3192-3193.
Xu et al., "Resolvin E1 inhibits neuropathic pain and spinal cord microglial activation following peripheral nerve injury", 2013, J. Neuroimmune Pharmacol, 8: 37-41.
Yildirim et al., "Drug-Target Network", 2007, Nat Biotechnol, 25:1119-1126.
Yoder et al. "Nanoscale Patterning in Mixed Fluorocarbon—Hydrocarbon Phospholipid Bilayers", J. Am. Chem. Soc. 2007, 129, 9037-9043.
Zhang and Casey, "Protein prenylation: molecular mechanisms and funcational consequences", 1996, Annu. Rev. Biochem., 65: 241-269.
Zhang et al. "Converting Peptides into Drug Leads by Lipidation", Current Medicinal Chemistry, 2012, vol. 48, p. 6571-6584.
Zimmerman et al., "Differential β-Arrestin-Dependent Conformational Signaling and Cellular Responses Revealed by Angiotensin Analogs", 2012, Sci Signal, 5(221):ra33.
Cash et al., "Resolution of inflammation: targeting GPCRs that interact with lipids and peptides", Drug Discovery Today, 2014, vol. 19, No. 8, p. 1186-1192.
NCT00799552, "A Phase II, Multi-Center, Double-Masked, Randomized, Placebo Controlled, Study on the Safety and Efficacy of RX-10045 on the Signs and Symptoms of Dry Eye in Every Day Environmental Conditions and During Provocation Using the Controlled Adverse Environment (CAE) Model", ClinicalTrials.gov, 2010, 5 pages.
Endo, H. "Resolving factors of inflammation—a bridge between Innate immunity and Adaptive immunity", Japanese Journal of Clinical Immunology, 2013, vol. 36, No. 3, p. 156-161. (English summary enclosed).
Herova M. et al., "ChemR23, the receptor for chemerin and resolving E1, is expressed and functional on M1 but not on M2 macrophages", The Journal of Immunology, 2015, vol. 194, No. 5, p. 2330-2337.
Cash et al. "Synthetic chemerin-derived peptides suppress inflammation through ChemR23", The Journal of Experimental Medicine, 2008, vol. 205, No. 4, p. 767-775.
Hesselink et al. "Resolvins and aliamides: lipid autacoids in ophthalmology—what promise do they hold?", Drug Design, Development and Therapy, 2016, vol. 10, p. 3133-3141.

* cited by examiner

A

B

| Peptides | HPLC Purity[a] (%) | Molecular Weights (Da) | |
|---|---|---|---|
| | | Calculated[b] | Observed[c] |
| l-SubP-COOH[d] | 98 | 2294.8 | 2295.1 [M+H]+ |
| s-CCK-Gly-COOH | 99 | 654.7 | 655.6 [M+H]+ |
| l-CCK-Gly-COOH[e] | 96 | 1430.7 | 1453.3 [M+Na]+ |

Figure 9

SEQUENCE LISTING

```
<160> NUMBER OF SEQ ID NOS: 16

<210> SEQ ID NO 1
<211> LENGTH: 51
<212> TYPE: PRT
<213> ORGANISM: Homo sapiens

<400> SEQUENCE: 1

Met Ser Thr Ser Met Ile Arg Asp Val Glu Leu Ala Glu Glu Ala Leu
1               5                   10                  15

Pro Lys Lys Thr Gly Gly Pro Gln Gly Ser Arg Arg Cys Leu Phe Ser
            20                  25                  30

Leu Phe Ile Val Ala Gly Ala Thr Thr Leu Phe Cys Leu Leu His Phe
        35                  40                  45

Gly Val Ile
    50
```

```
<210> SEQ ID NO 2
<211> LENGTH: 11
<212> TYPE: PRT
<213> ORGANISM: Artificial Sequence
<220> FEATURE:
<223> OTHER INFORMATION: Artificial polypeptide

<400> SEQUENCE: 2

Arg Pro Lys Pro Gln Gln Phe Phe Gly Leu Met
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Artificial polypeptide

<400> SEQUENCE: 3

Lys Gly Gly Arg Pro Lys Pro Gln Gln Phe Phe Gly Leu Met
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Artificial polypeptide

<400> SEQUENCE: 4

Trp Met Asp Phe Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Artificial polypeptide

<400> SEQUENCE: 5

Gly Gly Trp Met Asp Phe Gly
1               5

<210> SEQ ID NO 6
<211> LENGTH: 163
<212> TYPE: PRT
<213> ORGANISM: Homo sapiens

<400> SEQUENCE: 6

Met Arg Arg Leu Leu Ile Pro Leu Ala Leu Trp Leu Gly Ala Val Gly
1               5                   10                  15

Val Gly Val Ala Glu Leu Thr Glu Ala Gln Arg Arg Gly Leu Gln Val
                20                  25                  30

Ala Leu Glu Glu Phe His Lys His Pro Pro Val Gln Trp Ala Phe Gln
            35                  40                  45

Glu Thr Ser Val Glu Ser Ala Val Asp Thr Pro Phe Pro Ala Gly Ile
        50                  55                  60

Phe Val Arg Leu Glu Phe Lys Leu Gln Gln Thr Ser Cys Arg Lys Arg
65                  70                  75                  80

Asp Trp Lys Lys Pro Glu Cys Lys Val Arg Pro Asn Gly Arg Lys Arg
                85                  90                  95
```

```
            Lys Cys Leu Ala Cys Ile Lys Leu Gly Ser Glu Asp Lys Val Leu Gly
                        100                 105                 110

Arg Leu Val His Cys Pro Ile Glu Thr Gln Val Leu Arg Glu Ala Glu
                    115                 120                 125

Glu His Gln Glu Thr Gln Cys Leu Arg Val Gln Arg Ala Gly Glu Asp
                130                 135                 140

Pro His Ser Phe Tyr Phe Pro Gly Gln Phe Ala Phe Ser Lys Ala Leu
            145                 150                 155                 160

Pro Arg Ser

<210> SEQ ID NO 7
<211> LENGTH: 767
<212> TYPE: DNA
<213> ORGANISM: Homo sapiens

<400> SEQUENCE: 7
gccgccccgc gagaagaaga gcgggaagag gcggacagcg aggccaagat ttcagctgcg     60
ggacggtcag gggagaccte caggcgcagg gaaggacggc cagggtgaca cggaagcatg    120
cgacggctgc tgatccctct ggccctgtgg ctgggtgcgg tgggcgtggg cgtcgccgag    180
ctcacggaag cccagcgccg gggcctgcag gtggccctgg aggaatttca caagcacccg    240
cccgtgcagt gggccttcca ggagaccagt gtggagagcg ccgtggacac gcccttccca    300
gctggaatat ttgtgaggct ggaatttaag ctgcagcaga caagctgccg gaagagggac    360
tggaagaaac ccgagtgcaa agtcaggccc aatgggagga aacggaaatg cctggcctgc    420
atcaaactgg gctctgagga caaagttctg gccggttgg tccactgccc catagagacc    480
caagttctgc gggaggctga ggagcaccag gagacccagt gcctcagggt gcagcgggct    540
ggtgaggacc cccacagctt ctacttccct ggacagttcg ccttctccaa ggccctgccc    600
cgcagctaag ccagcactga gatgcgtggt gcctccagga ccgctgcggg tggtaaccag    660
tggaagaccc cagcccccag ggagaggaac ccgttctatc cccagccatg ataataaagc    720
tgctctccca gctgcctctc aaaaaaaaaa aaaaaaaaa aaaaaaa                   767

<210> SEQ ID NO 8
<211> LENGTH: 9
<212> TYPE: PRT
<213> ORGANISM: Homo sapiens

<400> SEQUENCE: 8

Tyr Phe Pro Gly Gln Phe Ala Phe Ser
1               5

<210> SEQ ID NO 9
<211> LENGTH: 12
<212> TYPE: PRT
<213> ORGANISM: Artificial Sequence
<220> FEATURE:
<223> OTHER INFORMATION: Artificial polypeptide

<400> SEQUENCE: 9

Lys Gly Gly Tyr Phe Pro Gly Gln Phe Ala Phe Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Artificial polypeptide
```

```
<220> FEATURE:
<221> NAME/KEY: MOD_RES
<222> LOCATION: (9)..(9)
<223> OTHER INFORMATION: X is (S)-1,2,3,4-tetrahydroisoquinoline-3-
      carboxylic acid.

<400> SEQUENCE: 10

Tyr Phe Leu Pro Ser Gln Phe Ala Xaa Ser
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (11)..(11)
<223> OTHER INFORMATION: X is (S)-1,2,3,4-tetrahydroisoquinoline-3-
      carboxylic acid.

<400> SEQUENCE: 11

Gly Gly Tyr Phe Leu Pro Ser Gln Phe Ala Xaa Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Artificial polypeptide

<400> SEQUENCE: 12

Arg Pro Lys Pro Gln Gln Phe Phe Gly Leu Met
1               5                   10

<210> SEQ ID NO 13
<211> LENGTH: 5
<212> TYPE: PRT
<213> ORGANISM: Artificial Sequence
<220> FEATURE:
<223> OTHER INFORMATION: Artificial polypeptide

<400> SEQUENCE: 13

Trp Met Asp Phe Gly
1               5

<210> SEQ ID NO 14
<211> LENGTH: 10
<212> TYPE: PRT
<213> ORGANISM: Homo sapiens

<400> SEQUENCE: 14

Glu Gln Lys Leu Ile Ser Glu Glu Asp Leu
1               5                   10

<210> SEQ ID NO 15
<211> LENGTH: 162
<212> TYPE: PRT
<213> ORGANISM: Mus musculus

<400> SEQUENCE: 15

Met Lys Cys Leu Leu Ile Ser Leu Ala Leu Trp Leu Gly Thr Val Gly
1               5                   10                  15

Thr Arg Gly Thr Glu Pro Glu Leu Ser Glu Thr Gln Arg Arg Ser Leu
            20                  25                  30
```

```
Gln Val Ala Leu Glu Glu Phe His Lys His Pro Val Gln Leu Ala
             35                  40                  45

Phe Gln Glu Ile Gly Val Asp Arg Ala Glu Glu Val Leu Phe Ser Ala
 50                  55                  60

Gly Thr Phe Val Arg Leu Glu Phe Lys Leu Gln Gln Thr Asn Cys Pro
 65                  70                  75                  80

Lys Lys Asp Trp Lys Lys Pro Glu Cys Thr Ile Lys Pro Asn Gly Arg
                 85                  90                  95

Arg Arg Lys Cys Leu Ala Cys Ile Lys Met Asp Pro Lys Gly Lys Ile
                100                 105                 110

Leu Gly Arg Ile Val His Cys Pro Ile Leu Lys Gln Gly Pro Gln Asp
            115                 120                 125

Pro Gln Glu Leu Gln Cys Ile Lys Ile Ala Gln Ala Gly Glu Asp Pro
    130                 135                 140

His Gly Tyr Phe Leu Pro Gly Gln Phe Ala Phe Ser Arg Ala Leu Arg
145                 150                 155                 160

Thr Lys

<210> SEQ ID NO 16
<211> LENGTH: 842
<212> TYPE: DNA
<213> ORGANISM: Mus musculus

<400> SEQUENCE: 16
aagaggaagg tcagggaact tgggaaaaca gaaaactcca aaactccgga ctctgggaga        60
agggtcagtg ggaaaaggcg gggctttggg gaccaagaga gaggagaaaa gggagatgag       120
agggtgagag ggaacaactg ccagggagct gttccaggga ccacacagaa aaaggcctcg       180
ctaaagcaac aaacctgatc attttcaaga accataggac tgaggtgaag ccatgaagtg       240
cttgctgatc tccctagccc tatggctggg cacagtgggc acacgtggga cagagcccga       300
actcagcgag acccagcgca ggagcctaca ggtggctctg gaggagttcc acaaacaccc       360
acctgtgcag ttggccttcc aagagatcgg tgtggacaga gctgaagaag tgctcttctc       420
agctggcacc tttgtgaggt tggaatttaa gctccagcag accaactgcc caagaagga        480 ctggaaaaag ccggagtgca caatcaaacc aaacgggaga aggcggaaat gcctggcctg       540
cattaaaatg gaccccaagg gtaaaattct aggccggata gtccactgcc caattctgaa       600
gcaagggcct caggatcctc aggagttgca atgcattaag atagcacagg ctggcgaaga       660
cccccacggc tacttcctac ctggacagtt tgccttctcc agggccctga gaaccaaata       720
agccctagac aggacttcac cttactccct gtacagctgt ggcagcaccc agcaggagca       780
tatcgtctcc cagagacttt caactccagg ctaataaaat gctgagtct gttcctttcc        840 aa                                                                      842
```

METHODS AND SYSTEMS FOR DESIGNING AND/OR CHARACTERIZING SOLUBLE LIPIDATED LIGAND AGENTS

CROSS-REFERENCE TO RELATED APPLICATIONS

This application is a divisional application of U.S. application Ser. No. 14/783,489 (now allowed), filed on Oct. 9, 2015, which is a national stage application, filed under 35 U.S.C. § 371, of International Application No. PCT/US2014/026662, filed on Mar. 13, 2014, which claims priority to, and the benefit of, U.S. provisional patent application Ser. No. 61/811,249, filed on Apr. 12, 2013 and 61/813,835, filed on Apr. 19, 2013. The contents of each application are hereby incorporated by reference in their entirety.

STATEMENT REGARDING FEDERALLY SPONSORED RESEARCH OR DEVELOPMENT

This invention was made with support under Grant Nos. R01 GM065500 and R01 CA125033, both awarded by the National Institutes of Health (NIH). The government has certain rights in the invention.

INCORPORATION BY REFERENCE OF SEQUENCE LISTING

The contents of the text file named "OKYO-001_D01US_SEQ_LISTING.txt", which was created on Jun. 20, 2017 and is 8561 bytes in size, are hereby incorporated by reference in their entireties.

BACKGROUND

A significant fraction of effective therapeutic agents act through interaction with cell surface receptors or other membrane-associated targets (e.g., ion channels, enzymes, etc). Significant investment has been directed to development of additional such agents. Of particular interest are agents susceptible to tissue-specific delivery.

SUMMARY

The present invention provides soluble lipidated ligand agents useful in a variety of diagnostic, therapeutic and/or research contexts. In general, provided agents comprise a ligand entity associated with a lipid entity. In some embodiments, the ligand and lipid entities are associated with one another by means of a linker entity. In some embodiments, provided soluble lipidated ligand agents associate with membranes (e.g., cell membranes). In some embodiments, provided soluble lipidated ligand agents that bind to membrane-associated targets are referred to herein as "Soluble Membrane Associated Ligands" (i.e., "SMALs").

Among other things, the present invention encompasses the recognition that linking a lipid entity to a ligand entity that interacts with a membrane-associated target can improve targeting (e.g., localization and/or retention) of the ligand entity to a site of interest (e.g., the vicinity of its target) which, in some embodiments, may reduce risk of off-target effects. Alternatively or additionally, the present invention encompasses the recognition that linking such a lipid entity to such a ligand entity may improve half-life of the ligand entity, particularly in a physiological setting and/or under relevant storage conditions. Still further, the present invention encompasses the surprising finding that a standardized system can be provided that permits design, identification and/or characterization of particular ligand entities with useful characteristics including susceptibility to lipidation with beneficial effects (including achieving and/or maintaining solubility) and/or lipid entities that impart desirable characteristics to a (ligand entity)-(lipid entity) conjugate, which system is generalizable and effective for a range of ligand entities, including ligand entities of different chemical composition (e.g., ligand entities comprising or consisting of peptide moieties, small molecule moieties, carbohydrate moeities, etc.) and/or directed to different membrane-associated targets of interest. The invention particularly encompasses the surprising finding that such system can effectively and reliably permit design, identification, and/or selection of ligand entities and/or lipid entities that, when linked together, form a conjugate that is soluble under relevant physiological conditions.

In some embodiments, provided systems for designing, identifying and/or selecting ligand entities and/or lipid entities may include comparison of one or more attributes or characteristics of a tethered form of a ligand entity with an untethered form of the ligand entity (e.g., an agent consisting of the ligand entity) using one or more in vitro assays. Alternatively or additionally, in some embodiments, provided systems for designing, identifying and/or selecting ligand entities and/or lipid entities may include comparison of one or more attributes or characteristics of a tethered form of a ligand entity with an untethered form of the ligand entity (e.g., an agent consisting of the ligand entity) using one or more in vivo assays. In some embodiments, a desirable lipid entity may be one that shows a difference (e.g., a statistically significant difference) in one or more such attributes or characteristics when in tethered form as compared with untethered form. For example, in some embodiments, a desirable lipid entity may show greater affinity for, increased on-rate to, decreased off-rate from, and/or greater effect on a relevant target (e.g., receptor) when utilized in tethered form as compared with untethered form. In some embodiments, difference may be or include an enhanced beneficial effect. In some embodiments, a difference may be or include a diminished negative effect.

In some embodiments, soluble lipidated ligand agents show a solubility under physiologically relevant conditions that is reasonably comparable to that of the unlipidated form of the ligand entity. In some embodiments, a lipidated ligand agent shows a solubility that is not reasonably comparable to that of the unlipidated form of the ligand entity. In some embodiments, a lipidated ligand agent shows solubility that is statistically significantly different from that of the unlipidated form of the ligand entity. In some embodiments, a soluble lipidated ligand agent will show a solubility that is 5%, 10%, 20%, 30%, 40%, or greater than that of the unlipidated form of the ligand entity. In some embodiments, a soluble lipidated ligand agent will show a solubility that is 5%, 10%, 20%, 30%, 40%, or lower than that of the unlipidated form of the ligand entity. In some embodiments, provided soluble lipidated ligand agents are soluble under physiologically relevant conditions in that they do not violate Lipinski's Rule.

In some embodiments, provided lipidated ligand agents show improved half-life (e.g., relative to an otherwise comparable non-lipidated form of the ligand entity, and/or to another appropriate reference) under relevant physiological conditions. In some embodiments, provided lipidated ligand entities show improved half-life (e.g., relative to an otherwise comparable non-lipidated form of the ligand entity or other appropriate reference) under relevant storage conditions. In some embodiments, improved half-life under relevant physiological conditions is statistically significantly different half-life as compared to a non-lipidated form of the ligand entity. In some embodiments, improved half-life under relevant storage conditions is statistically significantly greater half-life as compared to a non-lipidated form of the ligand entity.

In many embodiments, ligand entities useful in accordance with the present invention bind specifically with cell surface targets of interest. The present invention encompasses the finding that lipidation of certain such ligands can improve their localization, affinity and/or avidity and/or can stabilize interaction with their targets. Without wishing to be bound by any particular theory, the present inventors propose that lipidation of ligand entities that bind to cell surface targets (e.g., ion channels, enzymes, receptors such as G-Protein Coupled Receptors [GPCRs], etc) allows the lipidated ligand entities to associate preferentially with cell membranes, thereby effectively increasing the local concentration of the ligand in the vicinity of their cognate targets. Among other things, the present invention encompasses the recognition that such an effective increase in local concentration may permit utilization of ligand entities that might not be effective if administered absent lipidation, for example due to low affinity, or other issues that interfere with effective delivery to and/or interaction with or action on a relevant cognate target. Alternatively or additionally, in some embodiments, the present invention encompasses the recognition that enhanced membrane association and/or increased local concentration of ligand entities in the vicinity of their targets can reduce unintended and/or undesired off-target effects. In some embodiments, provided lipidated ligand agents exhibit substantially no off-target binding.

In some embodiments, a soluble lipidated ligand agent as described herein shows one or more improved properties as compared with an otherwise comparable non-lipidated version of the ligand entity. For example, in some embodiments, a lipidated ligand agent shows increased binding (affinity and/or avidity) to its target. In some embodiments, a lipidated ligand agent shows increased selectivity for its target. In some embodiments, a lipidated ligand agent shows increased inhibition of target activity (e.g., channel, enzyme, or receptor-mediated activity). In some embodiments, a lipidated ligand agent shows increased activation of target activity (e.g., channel, enzyme, or receptor-mediated activity).

In some embodiments, a soluble lipidated ligand agent interacts with its target at a site corresponding to and/or including that at which another ligand (e.g., a natural ligand, a drug, etc) for the target interacts. In some embodiments, a soluble lipidated ligand agent interacts with its target at a site remote from that at which another ligand (e.g., a natural ligand, a drug, etc), for example so that it has an allosteric effect on the target. In some embodiments, a soluble lipidated ligand agent competes with one or more other ligands (e.g., one or more natural ligands, drugs, etc) for the relevant target.

In some embodiments, a soluble lipidated ligand agent interacts directly with its target in that it makes direct non-covalent association (e.g., via an interaction that includes one or more of hydrogen bonds, hydrophobic interactions, van der Waals interactions, pi-cation interactions, pi-pi stacking, Coulombic and electrostatic interactions, pi-halogen interaction, aliphatic stacking, and/or any other non-covalent interaction).

In some embodiments, the present invention provides particular advantages associated with localized delivery and/or activity of provided soluble lipidated ligand agents. In some embodiments, provided soluble lipidated ligand agents are administered via a delivery route that itself achieves a degree of localization (e.g., non-systemic delivery such as via laparoscopy, arthroscopy, localized injection, topical application, or other means of localized delivery). Alternatively or additionally, in some embodiments, provided soluble lipidated ligand agents may self-localize, at least to a degree, for example as a result of inclusion of a localization moiety. For clarity, in some embodiments, a lipid entity may be or comprise a localization moiety, particularly given that certain lipid entities may themselves show preferential localization in vivo. To give but one example, in some embodiments, a lipid entity may be comprised of lipids that are preferentially found in and/or associate with a certain location or site (or plurality thereof) in vivo. Alternatively or additionally, in some embodiments, a ligand entity may be or comprise a localization entity, particularly given that certain ligand entities may themselves show preferential localization in vivo. To give but one example, in some embodiments, a ligand entity may be one that preferentially interacts with target(s) (e.g., particular group(s), class(es), or subclass(es) of receptors, enzymes, or channels) that are preferentially found in certain location(s) or site(s) in vivo. Alternatively or additionally, in some embodiments, a soluble lipidated ligand agents may include one or more localization moiet(ies) that are not lipid entities (or even lipids), and/or that are not ligand entities. In some embodiments, an administered soluble lipidated ligand agent is not detected systemically at significant levels. In some embodiments, an administered soluble lipidated ligand agent is not detected at one or more sites remote from its intended site of action.

In some embodiments, ligand entities for use in accordance with the present invention are or comprise peptides. In some embodiments peptidic ligand entities have a length between about 3 and about 500 amino acids. In some embodiments, peptidic ligand entities may comprise one or more modified and/or non-natural amino acids.

In some embodiments, ligand entities for use in accordance with the present invention are or comprise small molecules.

In some embodiments, the present invention provides systems for designing, characterizing, and/or manufacturing soluble lipidated ligand agents.

In some particular embodiments, the present invention provides systems that utilize a membrane-tethered configuration to identify and/or characterize ligand entities. For example, the present invention encompasses the finding that desirable ligand entities can be identified and/or characterized in a membrane-tethered configuration (i.e., a membrane-tethered ligand, or MTL) in which they are linked with a membrane-compatible entity that anchors them in a membrane. The present invention establishes specifically that such a membrane-tethered format can usefully reveal desirable attributes and/or characteristics of ligand entities, which ligand entities can then function effectively when incorporated into soluble lipidated ligand agents as described herein. In some particular embodiments, where both the ligand entity and the membrane tether are or comprise polypeptides, a membrane-tethered ligand entity conjugate can be prepared through recombinant technology. Those of ordinary skill in the art will appreciate that a recombinant format permits rapid generation and testing of a huge number of ligand entity-membrane tether conjugates, and particularly permits ready modification or substitution of possible ligand entity components (e.g., fused with the same membrane tether) for rapid identification and/or characterization of lipid entities of interest. Thus, creation of MTLs provide a low-cost and low-complexity alternative that allows for the rapid testing of therapeutic candidates that might otherwise be overlooked due to an undesirable side effect profile or low affinity for a target of interest.

Alternatively or additionally, in some embodiments, the present invention encompasses the recognition that various chemistries are available that permit modular assembly of covalently linked entities, so that, for example, different ligand entity-lipid entity combinations, with or without intervening linker entities, can readily be prepared and/or tested.

For example, in some embodiments, the present invention provides a first collection of potential ligand entities, each of which is attached to a chemically reactive moiety of a first type. In some embodiments, the present invention also provides a second collection of potential lipid entities, each of which is attached to a chemically reactive moiety of a second type, wherein reaction between the first and second types of chemically reactive moieties generates a covalent linkage. In some embodiments, such first and second types of chemically reactive moieties are so-called "click chemistry" moieties.

In general, provided soluble lipidated ligand agents include a ligand entity, a lipid entity, and, in some embodiments, an optional linker component. In a some aspects, the present invention defines relevant structural and/or functional parameters of each of these components and/or of their linkage to one another, thereby enabling appropriate selection of components to assemble active agents for any given target of interest. In some embodiments, the invention defines and/or provides sets of such components that include appropriate reactive moieties for linking components to one another, for example using simple and/or robust chemistries (e.g., click chemistry), so that selected components are readily linked to one another in the production of agents as described.

The present invention also provides, in some embodiments, compositions including at least one soluble lipidated ligand entity and a pharmaceutically acceptable carrier.

In some embodiments, a ligand entity binds to a membrane-associated target, for example, a cell-surface associated target or an intracellular target. In some embodiments, a membrane-associated target is or comprises a receptor, enzyme, or ion channel. In some embodiments, a ligand entity is or comprises a receptor ligand, an enzyme ligand, and/or an enzyme substrate.

In some embodiments, a soluble lipidated ligand agent will comprise a linker entity. In some embodiments a linker entity is or comprises a peptide. In some embodiments, a linker is or comprises a non-peptidic linker moiety. In some embodiments, a linker entity is formed at least in part as a result of a Click reaction. In some embodiments, the click reaction is an azide-alkyne Huisgen cycloaddition reaction. In some embodiments, a linker entity is or comprises at least one molecule of polyethylene glycol (PEG).

In accordance with the present invention, a lipid moiety may be linked to a ligand entity in any of a variety of sites on the ligand entity. To give but one example, in those embodiments in which a ligand entity is or comprises a peptide, a lipid entity may be linked to such peptide at or near the N-terminus, the C-terminus, and/or at one or more other positions (e.g., on a side chain, etc). In some embodiments, lipid entities are attached at a plurality of different locations on a particular ligand entity In many embodiments that utilize a peptide ligand entity, a lipid entity is attached at one or the other end of the ligand entity. Attachment of the lipid entity (and/or the linker entity) does not preclude interaction of the ligand entity with its target.

Typically, lipid entities are associated with ligand entities in accordance with the present invention by way of one or more covalent bonds.

Various embodiments of the present invention may be used to treat one or more diseases, disorders and/or conditions. Accordingly, in some embodiments, the present invention provides methods of treating a disease, disorder, or condition including administering to a subject in need thereof a soluble lipidated ligand agent comprising at least one ligand entity, at least one lipid entity, and, optionally, a linker entity connecting the at least one ligand entity to the at least one lipid entity. In some embodiments, a soluble lipidated ligand agent is administered in one or more doses that together delivery an amount effective such that at least one symptom or feature of a disease, disorder or condition is reduced in intensity, severity, duration, or frequency, and/or has delayed onset. In some embodiments, the soluble lipidated ligand agent is administered daily, twice a week, once a week, once every two weeks, once every three weeks, once a month, or at a variable interval. In some embodiments, soluble lipidated ligand agents may be administered in combination with one or more other therapeutically active agents.

In accordance with the present invention, provided lipidated ligand agents may be formulated, together with one or more pharmaceutically acceptable carriers, for delivery by any appropriate route. In some embodiments, soluble lipidated ligand entities are administered intravenously, intradermally, transdermally, orally, by inhalation, subcutaneously, and/or transmucosally.

BRIEF DESCRIPTION OF THE DRAWING

The Figures described below, that together make up the Drawing, are for illustration purposes only, and are not for limitation.

Data points represent the mean±S.E.M. from at least three independent experiments, each performed in triplicate.

Figure 5:
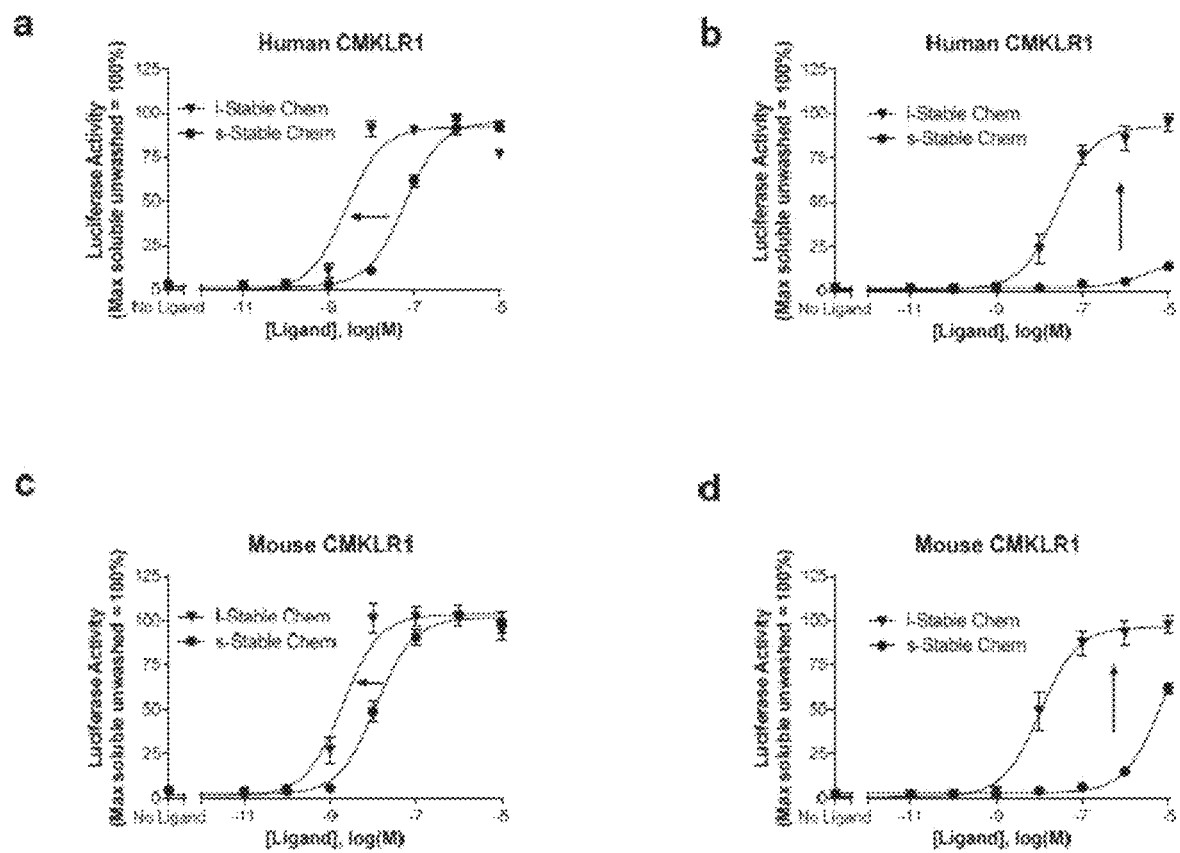

FIG. 5 shows a series of four exemplary graphs depicting the relative potency of a lipidated, stable chemerin analog (l-Stable Chem) as compared to the corresponding soluble peptide (s-Stable Chem) on the (A) human and (C) mouse CMKLR1. Panels (B) and (D) show the effects of serial washing on the activity of each peptide in human and mouse CMKLR1, respectively. Data points represent the mean±S.E.M. from at least three independent experiments, each performed in triplicate.

Figure 6:
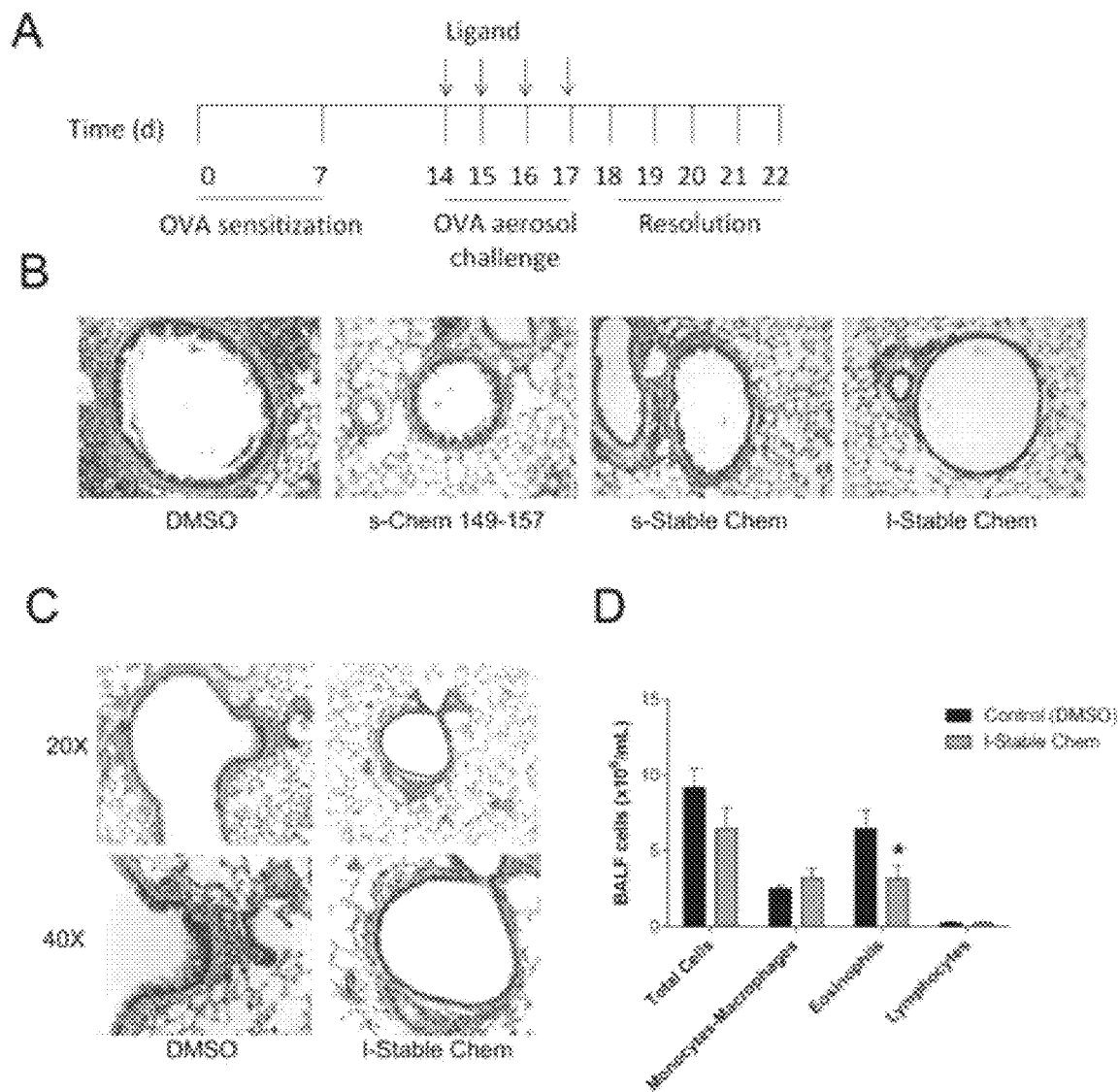

FIG. 6 depicts (A) an exemplary protocol for assessing allergic airway inflammation wherein mice are sensitized with intraperitoneal OVA on days 0 and 7, and ligand is administered 30 minutes prior to challenge with aerosolized OVA on days 14-17, panel (B) shows lung tissue sections from mice treated with DMSO, s-Chem149-157, s-Stable Chem, or l-Stable Chem and sacrificed at Day 18 were stained with periodic acid-Schiff reagent. Representative photographs are taken at 20× magnification. (C) Lung tissue sections at Day 18 were obtained from fixed, paraffin-embedded lung tissue stained with hematoxylin and eosin. Representative photographs are taken at both 20× and 40×. (D) Total BALF cells and leukocyte subsets were quantified on Day 18 and compared between mice receiving DMSO or l-Stable Chem. Data are representative of the mean±S.E.M. from n=3-8 mice per group. Comparison of DMSO control to l-Stable Chem: *$p<0.05$.

Figure 7:
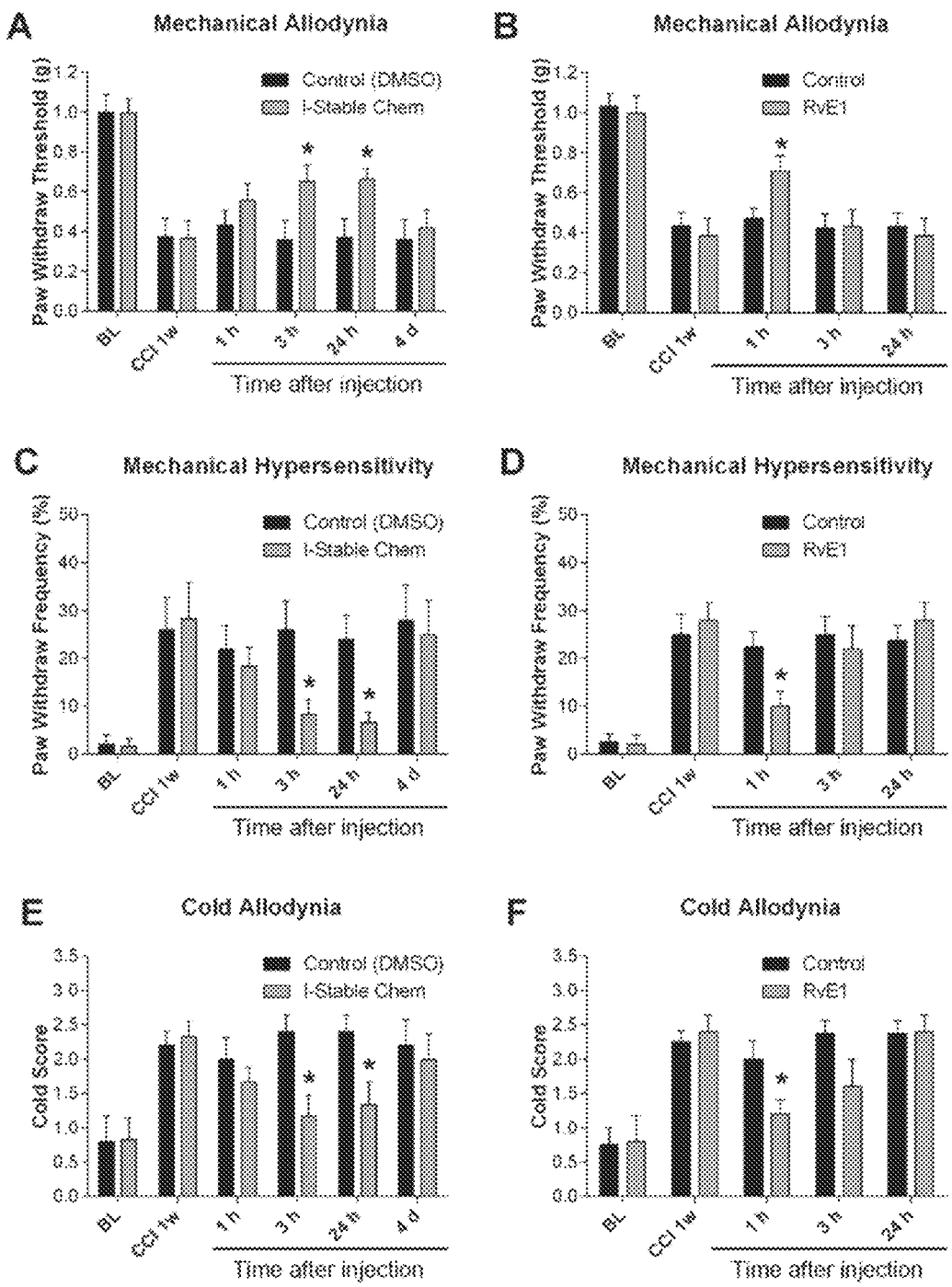

FIG. 7 shows exemplary graphs depicting the effect of intrathecal treatment with l-stable chem on CCI-induced neuropathic pain. Intrathecal injection of l-stable chem (100 pmol), 1 week after CCI, reduces CCI-induced mechanical hypersensitivity (panels A+C) and cold allodynia (panel E). Intrathecal injection of ResolvinE1 (RvE1)(100 pmol), 1 week after CCI, reduces CCI-induced mechanical hypersensitivity (panels B+D) and cold allodynia (panel F). BL=baseline before surgery.

Figure 8:
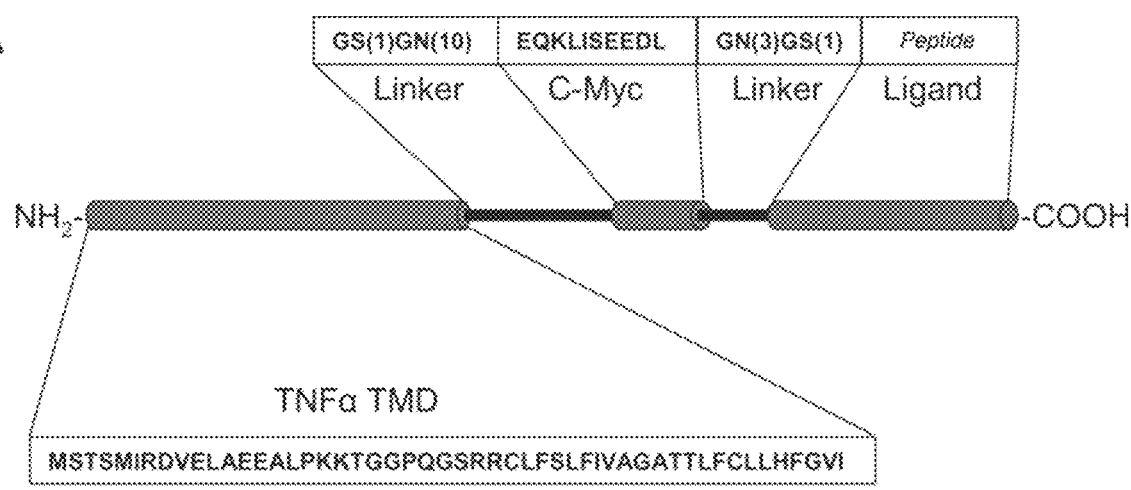
Figure 8:
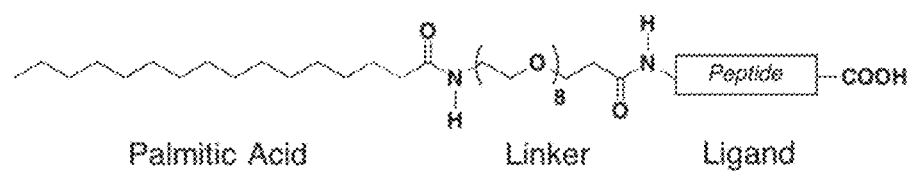

FIG. 8 shows exemplary schematic models depicting A) recombinant membrane tethered ligand and B) corresponding soluble lipidated ligand agent. Abbreviations: TNFα TMD=Tumor necrosis factor α transmembrane domain (SEQ ID NO.: 1); PEG=polyethylene glycol; amino acids are represented in single letter code. C-Myc (SEQ ID NO.: 14).

Figure 10:
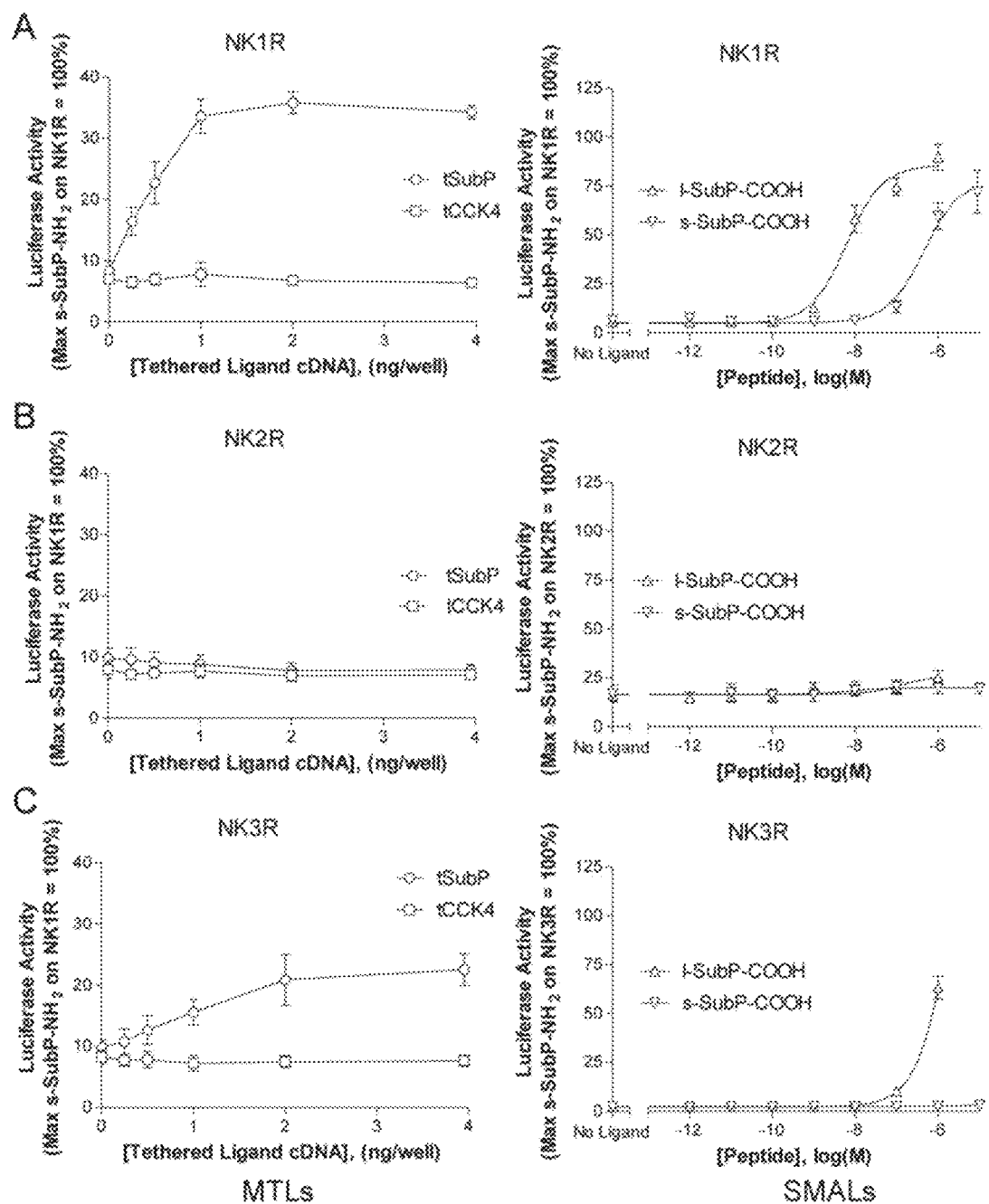
Figure 11:
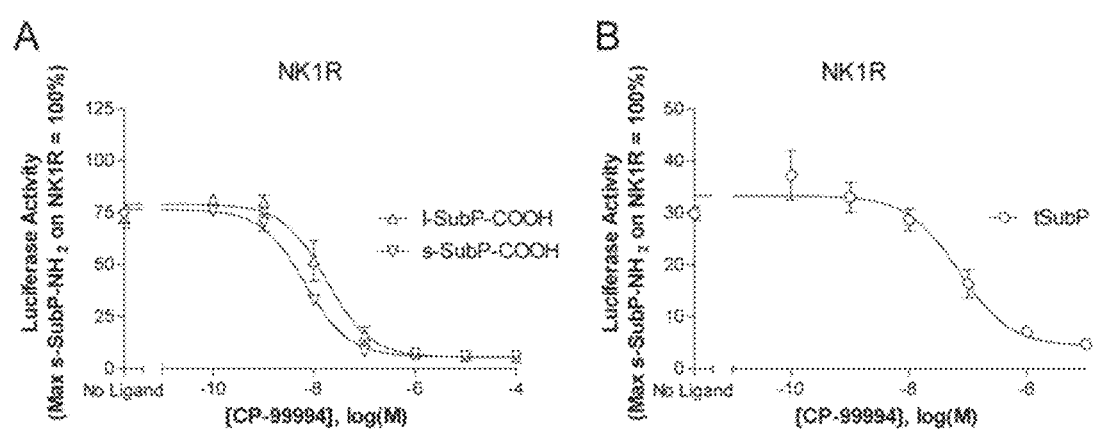

FIG. 9 depicts the chemical structure, purity, and molecular weight of exemplary synthesized peptides (s-Subp-COOH (SEQ ID NO.: 2); 1-SubP-COOH (SEQ ID NO.: 3); s-CCK4-Gly-COOH (SEQ ID NO.: 4); and 1-CCK4-Gly-COOH (SEQ ID NO.: 5)). Purity as determined by analytical RP-HPLC [Vydac C18, 5 im, 4 mm×250 mm] using a binary solvent system [A: $H_2O/CH_3CN/TFA$ (99/1/0.1); B: $CH_3CN/H_2O/TFA$ (90/10/0.07)] with a linear gradient of 65-80% solvent B over 20 min. The flow rate was set at 1 mL/min and elution was monitored by absorbance at 230 nm. Expected molecular weights were calculated using Peptide mass calculator v3.2 and confirmed by the analysis tool in ChemBioDraw Ultra v12.0.3.c) Observed molecular weights as determined using MALDI-TOF MS in reflectron positive mode using á-cyano-4-hydroxycinnamic acid as the matrix.d) KGG and e) GG spacer coupled to the N-terminus of the peptide before pegylation FIG. 10 shows exemplary results of provided tethered and lipidated peptides on neurokinin receptor signaling. Both tSubP and 1-SubP-COOH appear to activate NK1R (A) and NK3R (C) with no observed activity at NK2R (B). HEK293 cells were transiently cotransfected for 24 hours with cDNAs encoding: the designated NK receptor subtype, a 5X-SRE-Luc-pest reporter gene (pGL4.33), tethered ligand (for MTL assays, left panels), and a β-galactosidase gene to control for transfection variability. For assessment of soluble lipidated ligand agent induced signaling, cells were stimulated with ligand for 4 hours. Luciferase activity was quantified and normalized relative to a 4 hour stimulation with 1 μM soluble amidated substance P (s-SubP-$NH_2$) on the corresponding NK receptor subtype. Abbreviations: tSubP, tethered Substance P; tCCK4, tethered CCK4; s-SubP-COOH, soluble Substance P with a C-terminal free acid; l-SubP-COOH, lipidated Substance P with a C-terminal free acid; NK1R, neurokinin 1 receptor; NK2R, neurokinin 2 receptor; and NK3R, neurokinin 3 receptor. Data points represent the mean±S.E.M. from at least three independent experiments, each performed in triplicate FIG. 11 shows graphs of exemplary results of provided tethered and lipidated peptides on NK1R signaling in the presence of the small molecule NK1R antagonist, CP99994.CP 99994 appears to inhibit NK1R signaling induced by either a recombinant SubP MTL, soluble SubP with a C-terminal free acid (s-SubP-COOH), or the corresponding soluble lipidated ligand agent (l-SubP-COOH). A small molecule, CP 99994, inhibits NK1R activation by tSubP (A), s-SubP-COOH and 1-SubP-COOH (B). HEK293 cells were transiently cotransfected with cDNAs as outlined in Methods For tSubP experiments (A), 4 hours following transfection, cells were treated with increasing concentrations of CP 99994 for 20 hours. For s-SubP-COOH and 1-SubP-COOH experiments (B), 20 hours after transfection cells were treated with increasing concentrations of CP 99994 and 1 μM of indicated soluble ligands for an additional 4 hours. Luciferase activity was quantified and normalized relative to a parallel preparation of NK expressing cells stimulated for 4 hours with s-SubP-$NH_2$ (1 μM). Data represent the mean±SEM from 3 independent experiments, each performed in triplicate.

Figure 12:
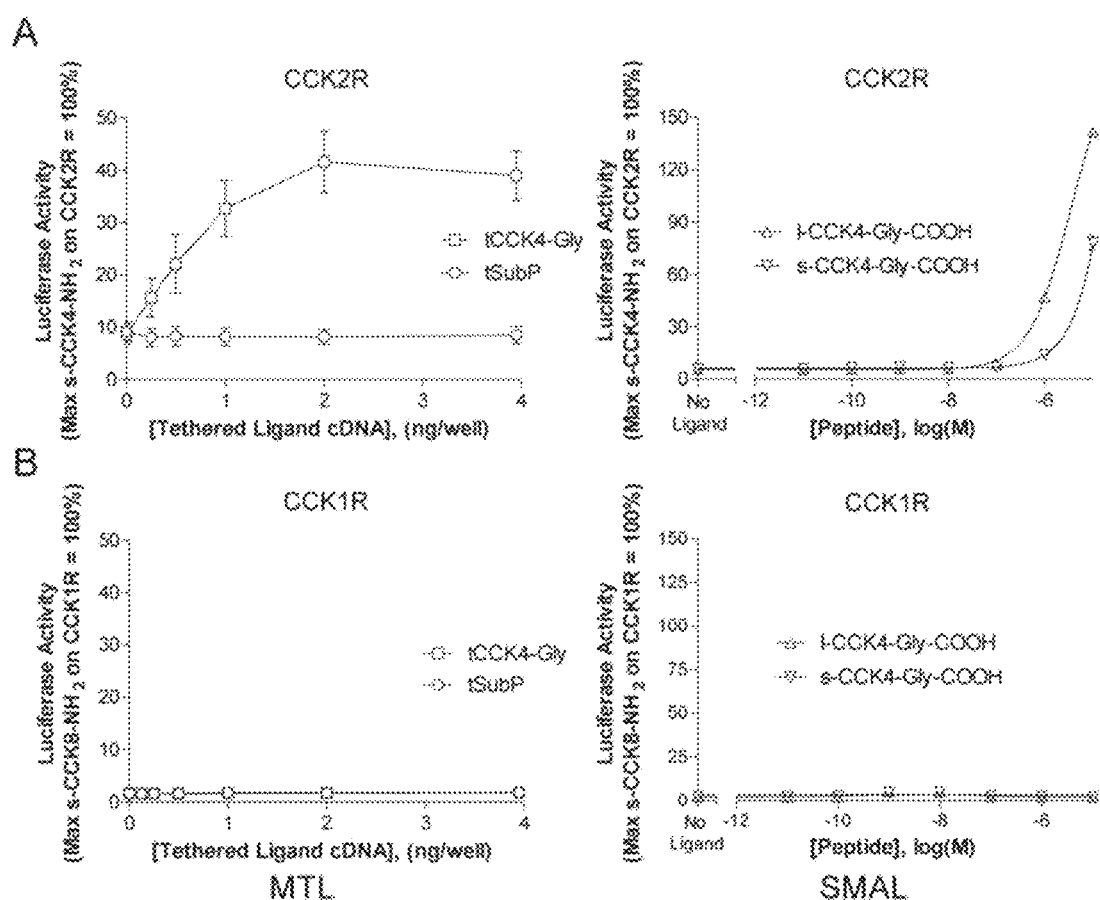
Figure 13:
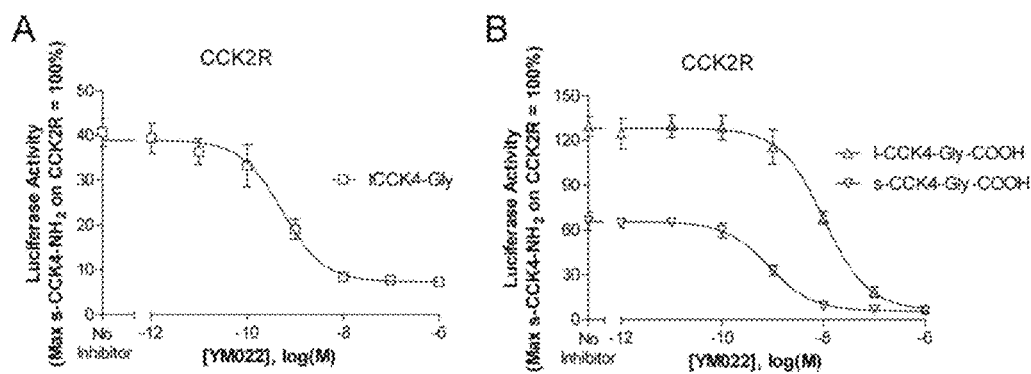

FIG. 12 shows graphs of exemplary results with provided anchored and lipidated peptides on CCK receptors. A) Tethered CCK4-Gly activates the CCK2 receptor (left panel). Potency of the corresponding soluble lipidated ligand agent (1-CCK4-Gly) exceeds that of soluble CCK-4-Gly (right panel). B) CCK4-Gly as a tethered (left panel), soluble or lipidated (right panel) ligand fails to activate the CCK1 receptor. HEK293 cells were transiently cotransfected with cDNAs encoding: the designated CCK receptor subtype, a 5X-SRE-Luc-pest reporter gene (pGL4.33), tethered ligand (as indicated) and a β-galactosidase gene to control for transfection efficiency. Tethered ligand activity was measured 24 hours following transfection. To assess activity of soluble and lipidated CCK-4-Gly, cells were stimulated for 4 hours with ligand. Both soluble and tethered ligand activity was quantified relative to a parallel preparation of CCK receptor expressing cells stimulated for 4 hours with soluble amidated CCK-4 (s-CCK4-$NH_2$, 10 μM) for CCK-2R and soluble amidated CCK-8 (s-CCK8-$NH_2$, 10 μM) for CCK-1R. Data represent the mean±SEM from 3 independent experiments, each performed in triplicate. Abbreviations: tCCK4-Gly, tethered glycine extended CCK4; tSubP, tethered Substance P; s-CCK4-Gly-COOH, soluble glycine extended CCK4 with a C-terminal free acid; l-CCK4-Gly-COOH, lipidated glycine extended CCK4 with a C-terminal free acid; CCK2R, cholecystokinin 2 receptor; CCK1R, cholecystokinin 1 receptor FIG. 13 shows graphs of exemplary results of provided tethered and lipidated peptides on CCK2R signaling in the presence of the small molecule CCK2R antagonist, YM022. A) YM022 blocks tethered CCK4-Gly mediated CCK2R signaling. HEK293 cells were cotransfected with cDNAs encoding: CCK2R, a 5X-SRE-Luc-pest reporter gene, tCCK4-Gly (as indicated), and a β-galactosidase gene to control for transfection efficiency. Four hours following transfection, cells were with treated with increasing concentrations of YM022 for 20 hours. Luciferase activity was quantified and normalized relative to a parallel preparation of CCK2R expressing cells stimulated for 4 hours with soluble amidated CCK-4 (s-CCK4-NH$_2$, 10 µM). B) YM022 blocks s-CCK-4-Gly-COOH and l-CCK4-Gly-COOH mediated activation of CCK2R. HEK293 cells were transfected as indicated above. Twenty hours after transfection, cells were with treated with increasing concentrations of YM022 together with either 10 µM of l-CCK4-Gly-COOH or s-CCK4-Gly-COOH. Following an additional four hour stimulation, luciferase activity was quantified and normalized as outlined for panel A. Data represent the mean±SEM from 3 independent experiments, each performed in triplicate. Abbreviations: tCCK4-Gly, tethered glycine extended CCK4; s-CCK4-Gly-COOH, soluble glycine extended CCK4 with a C-terminal free acid; l-CCK4-Gly-COOH, lipidated glycine extended CCK4 with a C-terminal free acid; CCK2R, cholecystokinin 2 receptor.

Figure 14:
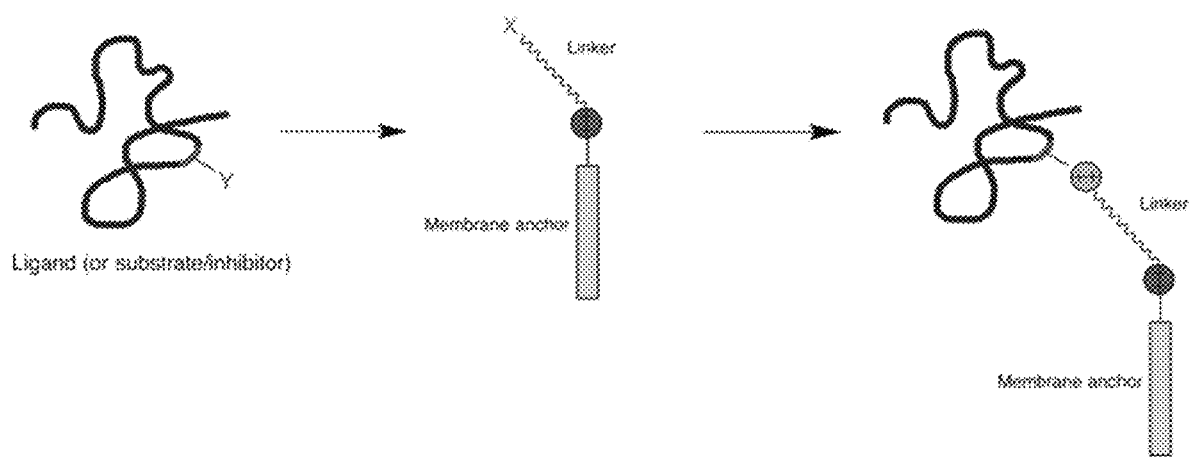

FIG. 14 is a schematic diagram a non-limiting exemplary association between a ligand entity and a lipid entity.

DEFINITIONS

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Administration: As used herein, the term "administration" refers to the administration of one or more agents or compositions to a subject. Administration may be by any appropriate route. For example, in some embodiments, administration may be bronchial (including by bronchial instillation), buccal, enteral, interdermal, intra-arterial, intraarticular, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal. In some embodiments, administration is systemic administration. In some embodiments, administration is tissue specific administration.

Animal: As used herein, the term "animal" refers to any member of the animal kingdom. In some embodiments, "animal" refers to humans, at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

Amino acid: As used herein, the term "amino acid," in its broadest sense, refers to any compound and/or substance that can be incorporated into a polypeptide chain, e.g., through formation of one or more peptide bonds. In some embodiments, an amino acid has the general structure H2N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

Approximately: As used herein, the term "approximately" and "about" is intended to encompass normal statistical variation as would be understood by those of ordinary skill in the art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a substance that has activity in a biological system (e.g., in a cell (e.g., isolated, in culture, in a tissue, in an organism), in a cell culture, in a tissue, in an organism, etc.). For instance, a substance that, when administered to an organism, has a biological effect on that organism, is considered to be biologically active. It will be appreciated by those skilled in the art that often only a portion or fragment of a biologically active substance is required (e.g., is necessary and sufficient) for the activity to be present; in such circumstances, that portion or fragment is considered to be a "biologically active" portion or fragment.

Combination therapy: As used herein, the term "combination therapy" refers to those situations in which a subject is simultaneously exposed to two or more therapeutic agents. In some embodiments, such agents are administered simultaneously; in some embodiments, such agents are administered sequentially; in some embodiments, such agents are administered in overlapping regimens.

Corresponding to: As used herein, the term "corresponding to" is often used to designate the position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the 190$^{th}$ residue in the first polymer but rather corresponds to the residue found at the 190$^{th}$ position in the reference polymer; those of ordinary skill in the art readily appreciate how to identify "corresponding" amino acids, including through use of one or more commercially-available algorithms specifically designed for polymer sequence comparisons.

Dosage form: As used herein, the term "dosage form" refers to a physically discrete unit of a therapeutic agent for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen).

Dosing regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, a dosing regimen is correlated with a desired or beneficial outcome when administered across a relevant population (i.e., is a therapeutic dosing regimen).

Effective Amount: As used herein, the term "effective amount" refers to a quantity of a substance that is sufficient to achieve a desired biological effect. Combined with the teachings provided herein, by choosing among the various provided agents and weighing factors such as potency, relative bioavailability, patient body weight, severity of adverse side effects and preferred mode of administration, an effective prophylactic or therapeutic treatment regimen can be planned which does not cause substantial unwanted toxicity and yet is effective to treat a particular subject. The effective amount for any particular application can vary depending on such factors as the disease or condition being treated, the particular agent(s) being administered, the size of the subject, and/or the severity of the disease or condition. One of ordinary skill in the art can empirically determine the effective amount of a particular embodiment without necessitating undue experimentation. It is preferred generally that a maximum does be used, that is, the highest safe dose according to sound medical judgment. Multiple doses per day may be contemplated to achieve appropriate systemic levels of provided agents. Appropriate systemic levels can be determined by, for example, measurement of the subject's peak or sustained plasma level of the agent. "Dose" and "dosage" are used interchangeably herein.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Functional: As used herein, the term "functional" is used to refer to a form or fragment of an entity that exhibits a particular property and/or activity.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

Human: In some embodiments, a human is an embryo, a fetus, an infant, a child, a teenager, an adult, or a senior citizen.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. As will be understood by those skilled in the art, a variety of algorithms are available that permit comparison of sequences in order to determine their degree of identity, including by permitting gaps of designated length in one sequence relative to another when considering which residues "correspond" to one another in different sequences. Calculation of the percent identity between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. Representative algorithms and computer programs useful in determining the percent identity between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined for example using the GAP program in the GCG software package using an NWSgapdna.CMP matrix.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients.

Ligand: As used herein, the term "ligand" refers to an ion, molecule, or molecular group that binds to another chemical entity to form a larger complex. In some cases, when a ligand binds to a protein, such as a receptor, a ligand may be an agonist, an antagonist, or an inverse agonist and may bind in a direct or allosteric manner.

Lipid: As used herein, the term "lipid" refers to any fatty, waxy, or other nonpolar compound (e.g., cholesterol) that is readily soluble in a nonpolar solvent (e.g., 2-octanol or a hydrocarbon solvent like n-hexane), but is substantially insoluble in a polar solvent (e.g., water). Examples of lipids include, but are not limited to, oils, waxes, isoprenoids, and steroids.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long.

Patient: As used herein, the term "patient" or "subject" refers to a human or any non-human animal (e.g., mouse, rat, rabbit, dog, cat, cattle, swine, sheep, horse or primate) to whom therapy is administered. In many embodiments, a patient is a human being. In some embodiments, a patient is a human presenting to a medical provider for diagnosis or treatment of a disease, disorder or condition. In some embodiments, a patient displays one or more symptoms or characteristics of a disease, disorder or condition. In some embodiments, a patient does not display any symptom or characteristic of a disease, disorder, or condition. In some embodiments, a patient is someone with one or more features characteristic of susceptibility to or risk of a disease, disorder, or condition.

Pharmaceutically acceptable: The term "pharmaceutically acceptable" as used herein, refers to agents that, within the scope of sound medical judgment, are suitable for use in contact with tissues of human beings and/or animals without excessive toxicity, irritation, allergic response, or other problem or complication, commensurate with a reasonable benefit/risk ratio.

Polypeptide: The term "polypeptide", as used herein, generally has its art-recognized meaning of a polymer of at least three amino acids. In some embodiments, the term is used to refer to specific functional classes of polypeptides, such as, for example, cell surface receptor ligands, ion channel modulators, etc. For each such class, the present specification provides several examples of amino acid sequences of known exemplary polypeptides within the class; in some embodiments, such known polypeptides are reference polypeptides for the class. In such embodiments, the term "polypeptide" refers to any member of the class that shows significant sequence homology or identity with a relevant reference polypeptide. In many embodiments, such member also shares significant activity with the reference polypeptide. For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region, often including a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids.

Precursor Polypeptide: As used herein, the term "precursor polypeptide" refers to i) a precursor form of a biologically active polypeptide and/or ii) a polypeptide this is not biologically active until modified in some way. For example, in some embodiments, a precursor polypeptide differs from a biologically active polypeptide in the presence or absence of one or more particular post-translational modifications (e.g., one or more alkyl, phosphate, sulfonate, glycan, or lipid groups whose presence, absence, or level correlates with activity (or lack thereof) of the relevant peptide). In some embodiments, a precursor polypeptide differs from a biologically active polypeptide in the presence or absence of a particular set of, typcically contiguous, amino acids (e.g., a pro-moiety that is cleaved to form the active polypeptide, or a set of amino acids that is spliced onto the precursor polypeptide to form the active polypeptide). In some particular embodiments, action of one or more enzymes, for example, a kinase, a phosphatase, a protease, and/or an amidase, converts a precursor polypeptide to a biologically active polypeptide. In some embodiments, a precursor polypeptide is or comprises a zymogen and/or a proenzyme. In some embodiments, a precursor peptide is converted to an active polypeptide via one or more post-translational modification. Exemplary post translational modifications include, but are not limited to, octanylation, myristoylation, palmitoylation, isoprenylation, glypiation, lipoylation, flavin, heme C attachment, phosphopantetheinylation, retinylidene Schiff base formation, diphtamide formation, ethanolamine phosphoglycerol attachment, hypusine formation, acylation, alkylation, amide bond formation, butyrylation, gamma-carboxylation, glycosylation, malonylation, hydroxylation, iodination, nnucleotide addition, oxidation, phosphate ester or phosphoramide formation, propionylation, phyroglutamate formation, S-glutathionylation, S-nitrosylation, succinylation, sulfation, selenoylation, glycation, biotinylation, pegylation, ISGylation, SUMOylation, ubiquitination, Neddylation, Pupylation, citrullination, deamidation, eliminylation, carbamylation, and/or disulfide bridge formation.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Small molecule: As used herein, the term "small molecule" means a low molecular weight organic compound that may serve as an enzyme substrate or regulator of biological processes. In general, a "small molecule" is a molecule that is less than about 5 kilodaltons (kD) in size. In some embodiments, provided nanoparticles further include one or more small molecules. In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, one or more small molecules are encapsulated within the nanoparticle. In some embodiments, small molecules are non-polymeric. In some embodiments, in accordance with the present invention, small molecules are not proteins, polypeptides, oligopeptides, peptides, polynucleotides, oligonucleotides, polysaccharides, glycoproteins, proteoglycans, etc. In some embodiments, a small molecule is a therapeutic. In some embodiments, a small molecule is an adjuvant. In some embodiments, a small molecule is a drug.

Stable: The term "stable," when applied to compositions herein, means that the compositions maintain one or more aspects of their physical structure (e.g., size range and/or distribution of particles) over a period of time. In some embodiments, a stable composition is one for which a biologically relevant activity is maintained for a period of time. In some embodiments, the period of time is at least about one minute; in some embodiments the period of time is about 90 seconds, about 2 minutes, about 5 minutes, about 10 minutes, about 15 minutes, about 30 minutes, about 45 minutes, about 1 hour, about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. In some embodiments, a stable composition is stable at ambient conditions. In some embodiments, a stable composition is stable under biologic conditions (i.e. 37° C. in phosphate buffered saline).

Subject: As used herein, the term "subject" refers to a living mammal. In various embodiments a subject is a non-human mammal, including, without limitation, a mouse, rat, hamster, guinea pig, rabbit, sheep, goat, cat, dog, pig, horse, cow, or non-human primate. In one embodiment a subject is a human.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition has been diagnosed with and/or exhibits or has exhibited one or more symptoms or characteristics of the disease, disorder, or condition.

Susceptible to: An individual who is "susceptible to" a disease, disorder, or condition is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from the disease, disorder, or condition).

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom.

Therapeutic agent: As used herein, the phrase "therapeutic agent" refers to any agent that has a therapeutic effect and/or elicits a desired biological and/or pharmacological effect, when administered to a subject. In some embodiments, an agent is considered to be a therapeutic agent if its administration to a relevant population is statistically correlated with a desired or beneficial therapeutic outcome in the population, whether or not a particular subject to whom the agent is administered experiences the desired or beneficial therapeutic outcome.

Therapeutically effective amount: As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc). Those of ordinary skill in the art will appreciate that, in some embodiments, a therapeutically effective agent may be formulated and/or administered in a single dose. In some embodiments, a therapeutically effective agent may be formulated and/or administered in a plurality of doses, for example, as part of a dosing regimen.

Therapeutic regimen: A "therapeutic regimen", as that term is used herein, refers to a dosing regimen whose administration across a relevant population is correlated with a desired or beneficial therapeutic outcome.

Treatment: As used herein, the term "treatment" (also "treat" or "treating") refers to any administration of a substance that partially or completely alleviates, ameliorates, relieves, inhibits, delays onset of, reduces severity of, and/or reduces frequency, incidence or severity of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION OF CERTAIN EMBODIMENTS

As described herein, the present invention provides, among other things, soluble lipidated ligand agents, compositions comprising such agents, and methods for the identification, characterization, and development of soluble lipidated ligand agents. The present invention encompasses the insight that lipidation of certain ligand entities can improve localization, affinity and/or avidity of such agents and/or can stabilize interaction with their cognate membrane-associated targets (e.g., channels, enzymes, and/or receptors, etc) such that the agent has a desired biological activity. The present invention teaches, in some embodiments, that even ligand entities that are inactive in other forms can surprisingly be rendered biologically active in a lipidated format as described herein. Furthermore, the present invention demonstrates that lipidated forms of ligand entities of interest can be identified that are sufficiently soluble in physiologically relevant contexts to permit formulation, administration, and activity of provided agents to achieve desired biological effects.

The present invention also provides systems for identifying, characterizing, and/or manufacturing such lipidated ligand agents. In some embodiments, provided systems utilize a membrane-tethered format to identify and/or characterize ligand, linker, and/or lipid entities of interest. In some embodiments, modular systems are provided that permit facile linkage of various ligand entities, linker entities, and/or lipid entities with one another. In some embodiments, such modular system permit ready re-assortment of components.

Ligand Entities

Any of a variety of ligand entities may be utilized in accordance with the present invention. In some embodiments, a ligand entity is or comprises a receptor ligand, an ion channel ligand, an enzyme ligand, and/or enzyme substrate.

In some embodiments, a ligand entity binds to a membrane-associated target. In some embodiments, a membrane-associated target may be or comprise a receptor (e.g., a G-protein-coupled receptor), an enzyme, and/or a channel (e.g., an ion channel). In some embodiments, a target is associated with an extracellular membrane. In some embodiments, a target is associated with an intracellular membrane. In some embodiments, a target is associated with an extracellular surface of a membrane. In some embodiments, a target is associated with an intracellular surface of a membrane.

In some embodiments, a ligand entity shows enhanced activity when linked to a lipid entity than when tested under otherwise comparable conditions not linked to the lipid entity. In some embodiments, a ligand entity shows comparable activity in a membrane-tethered form as in a lipidated form.

In some embodiments, a ligand entity is soluble. In some embodiments, a ligand entity's solubility is altered by linkage to a lipid moiety. In some embodiments, a ligand entity's solubility is increased by linkage to a lipid moiety. In some embodiments, a ligand entity's solubility is decreased by linkage to a lipid moiety.

Lipidated ligand agents of particular interest herein are soluble under physiologically relevant conditions. In some embodiments, soluble lipidated ligand agents show a solubility under physiologically relevant conditions that is reasonably comparable to that of the unlipidated form of the ligand entity. In some embodiments, a lipidated ligand agent shows a solubility that is not reasonably comparable to that of the unlipidated form of the ligand entity. In some embodiments, a lipidated ligand agent shows solubility that is statistically significantly different from that of the unlipidated form of the ligand entity. In some embodiments, a soluble lipidated ligand agent will show a solubility that is 5%, 10%, 20%, 30%, 40%, or greater than that of the unlipidated form of the ligand entity (e.g. in a nonpolar solvent). In some embodiments, a soluble lipidated ligand agent will show a solubility that is 5%, 10%, 20%, 30%, 40%, or lower than that of the unlipidated form of the ligand entity. (e.g. in water) In some embodiments, a lipidated ligand agent is considered to be appropriately soluble if it does not violate Lipinski's Rule (for more information, see Lipinski C A, Lead- and Drug-Like Compounds: The Rule of Five Revolution, 2004, Drug Discovery Today, 1(4):337-341). Briefly, Lipinski's Rule states that a candidate drug may make a good oral therapeutic if it meets the following criteria: 1) it does not contain more than 5 hydrogen bond donors (nitrogen or oxygen atoms with one or more hydrogen atoms), 1) it does not contain more than 10 hydrogen bond acceptors (nitrogen or oxygen atoms), 3) it has a molecular mass of less than 500 daltons, and 4) is has an octanol-water partition coefficient log P not greater than 5, According to a specific application of some embodiments, a desirable definition of solubility may vary. Exemplary descriptions of desirable solubility characteristics appropriate for certain embodiments may be found, inter alia, in Edwards and Price, Role of Physiochemical Properties and Ligand Lipophilicity Efficiency in Addressing Drug Safety Risks, Annual Reports in Medicinal Chemistry, 2010, 45:380-391; and Valko K, Application of High-Performance Liquid Chromatography Based Measurements of Lipophilicity to Model Biological Distribution, 2004, J. Chromatography, 1037:(1-2): 299-301, the disclosures of which are hereby incorporated by reference in their entirety.

Those of ordinary skill in the art will appreciate that a ligand entity for use in accordance with the present invention may be of any chemical type. For example, in some embodiments, a ligand entity is or comprises a polypeptide. In some embodiments, a ligand entity is or comprises a small molecule. In some embodiments, a ligand entity is or comprises a lipid or a free fatty acid.

In some embodiments, a ligand entity included in a soluble lipidated ligand agent as described herein consists of a target ligand, e.g., a naturally occurring target ligand such as a receptor ligand or an enzyme substrate. That is, In some embodiments, a ligand entity has a structure that is substantially or wholly identical to that of a reference ligand (e.g., a naturally-occurring ligand or a ligand that is otherwise known to bind the target, such as for example a receptor ligand or enzyme substrate). In some embodiments, a ligand entity included in a soluble lipidated ligand agent as described herein has one or more structural modifications (e.g., one or more additional pendant groups, or missing moieties) as compared with a reference ligand.

In general, any agent that, when linked to a lipid entity as described herein, binds appropriately to a target of interest, may be utilized as a ligand entity in accordance with the present invention. In some embodiments, the present invention is applicable to virtually any "druggable target". Those of skill in the art will be able to determine appropriate targets, and exemplary, non-limiting appropriate targets may be found, inter alia, in Overington et al., How Many Druggable Targets Are There?, 2006, *Nat Rev Drug Discov*, 5:993-996; Yildirim et al., Drug-Target Network, 2007, *Nat Biotechnol*, 25:1119-1126; Rask-Andersen et al, The Druggable Genome: Evaluation of Drug Targets in Clinical Trials Suggests Major Shifts in Molecular Class and Indication, 2013, *Annu Rev Pharmacol Toxicol*, 54:9-26; and Lagerstrom and Schioth, Structural Diversity of G Protein-Coupled Receptors and Significance for Drug Discovery, 2008, *Nat Rev Drug Discov*, 7:339-357.

In some embodiments, a target may be selected based on consideration of one or more factors such as, for example, tissue accessibility (i.e., ease of getting agent to the target). In some embodiments, tissues which may be considered accessible, and thus providing desirable targets, include tissues of: the respiratory tract including nasal mucosa, gastrointestinal tract (including mouth, stomach, small intestine, colon), skin, joint space, tendons, intrathecal space, vertebral space, conjunctiva, and eye.

In some embodiments, a ligand entity is or comprises a channel ligand, such as an ion channel ligand. Any of a variety of ion channel ligands may be used according to various embodiments. Exemplary ion channels that may be targeted by some embodiments include, but are not limited to: voltage-gated ion channels and ligand-gated ion channels. Exemplary voltage-gated ion channels include, but are not limited to: CatSper and two-pore channels, cyclic nucleotide-regulated channels, potassium channels, calcium-activated potassium channels, inwardly rectifying potassium channels, two-p potassium channels, voltage-gated potassium channels, transient receptor potential channels, voltage-gated calcium channels, and voltage-gated sodium channels. Exemplary ligand-gated ion channels include, but are not limited to: 5-$HT_3$ receptors, $GABA_A$ receptors, glycine receptors, ionotropic glutamate receptors, nicotinic acetylcholine receptors, P2X receptors, and zinc-activated ion channels.

In some embodiments, a ligand entity is or comprises a channel blocker, such as an ion channel blocker. Any of a variety of channel blockers may be used in accordance with some embodiments. Exemplary ion channel blockers include, but are not limited to: calcium channel blockers, chloride channel blockers, potassium channel blockers, sodium channel blockers (e.g., alkaloid based toxins, saxitoxin, neosaxitoxin, tetrodotoxin). Exemplary ligand-gated ion channel antagonists include, but are not limited to: 5-$HT_3$ receptor antagonists. AMPA receptor antagonists, $GABA_A$ receptor antagonists, Glycine receptor antagonists, Kainate receptor antagonists, nACh receptor antagonists, NMDA receptor antagonists, P2X receptor antagonists, and Zinc-activated channel antagonists.

In some embodiments, a ligand entity is or comprises an enzyme ligand, such as a substrate. In some embodiments, an enzyme ligand associates with one or more known membrane-associated enzymes. Non-limiting exemplary enzymes to which certain embodiments may associate include: kinases, peptidases, proteinases, and cyclo-ligases. Exemplary kinases include, but are not limited to, members of the: AGC Containing PKA, PKG, and PKC families; DMPK family (e.g., GEK subfamily, Other DMPK family kinases, or Rho kinase); RSK family (e.g., MSK subfamily, p70 subfamily, RSK subfamily, RSKR subfamily); MAST family; NDR family; G protein-coupled receptor kinases (e.g., BARK subfamily, GRK subfamily); PDK1 family; Protein kinase A; Akt (Protein kinase B); Protein kinase C (PKC, e.g., Alpha subfamily, Delta subfamily, Eta subfamily, Iota subfamily); Protein kinase G (PKG); Protein kinase N (PKN) family; RSKL family; SGK family; and the YANK family. In some embodiments, an enzyme ligand is an agonist or partial agonist. In some embodiments, an enzyme ligand is an antagonist.

Exemplary atypical kinases include, but are not limited to, members of the: ABC1 family (e.g., ABC1-A subfamily, ABC1-B subfamily); Alpha kinase family (e.g., ChaK subfamily, eEF2K subfamily); Phosphatidyl inositol 3' kinase-related kinases (PIKK) family (e.g., ATR subfamily, FRAP subfamily, SMGI subfamily, TRRAP subfamily); RIO family (e.g., RIO1 subfamily, RIO2 subfamily, RIO3 subfamily); Bromodomain kinase (BRD) family; G11 family; PDHK family; Pyruvate dehydrogenase kinase (PDHK) family; TAF1 family; TIF1 family; CAMK: Calcium/calmodulin-dependent protein kinases; CAMK-like (CAMKL) family (e.g., AMPK subfamily, BRSK subfamily, CHK1 subfamily, HUNK subfamily, LKB subfamily, MARK subfamily, MELK subfamily, NuaK subfamily, PASK subfamily, QIK subfamily, SNRK subfamily); MAPK-Activated Protein Kinase (MAPKAPK) family; CAMK1 family; CAMK2 family; CAMK-unique family; CASK family; DCAMKL family; Death-associated kinase (DAPK) family; Myosin Light Chain Kinase (MLCK) family; Phosphorylase Kinase (PHK) family; PIM family; Protein kinase D (PKD) family; PSK family; RAD53 family; Testis specific kinase (TSSK) family; Trbl family; Trio family; Casein kinase 1 (CK1) family; Tau tubulin kinase (TTBK) family; Vaccina related kinase (VRK) family; Cyclin-dependent kinase (CDK) family (e.g., CCRK subfamily, CDK4 subfamily, CDK9 subfamily, CDK1 subfamily, CDK10 subfamily, CDK5 subfamily, CDK7 subfamily, CDK8 subfamily, CRK7 subfamily, PITSLRE subfamily, TAIRE subfamily); Dual-specificity tyrosine-(Y)-phosphorylation regulated kinase (DYRK) family (e.g., Dyrk1 subfamily, Dyrk2 subfamily, HIPK subfamily, PRP4 subfamily); Glycogen synthase kinase (GSK) family; CLK family; Cyclin-dependent kinase-like (CDKL) family; Mitogen-activated protein kinases (e.g., ERK subfamily, Erk7 subfamily, JNK subfamily, p38 subfamily, nmo subfamily); RCK family; and SRPK family.

Exemplary lipid modifying kinases include, but are not limited to members of the: 1-phosphatidylinositol 4-kinase family, Phosphatidylinositol-4-phosphate 3-kinase family, Phosphatidylinositol 3-kinase family, Phosphatidylinositol-4,5-bisphosphate 3-kinase family, 1-phosphatidylinositol-5-phosphate 4-kinase family, 1-phosphatidylinositol-4-phosphate 5-kinase family, and Sphingosine kinase family.

Oher exemplary kinases include, but are not limited to members of the: Receptor Guanylate Cyclase (RGC) family, CAMKK family, Aurora kinase (Aur) family, Bub family, Bud32 family, Casein kinase 2 (CK2) family, CDC1$_7$ family, Haspin family, IKK family, IRE family, MOS family, NAK family, NIMA (never in mitosis gene a)-related kinase (NEK) family, NKF1 family, NKF2 family, NKF4 family, NKF5 family, NRBP family, Numb-associated kinase (NAK) family, Polo-like kinase (PLK) family, PEK family (e.g., GCN2 subfamily, PEK subfamily, or other PEK family kinases), SgK493 family, Slob family, TBCK family, TOPK family, Tousled-like kinase (TLK) family, TTK family, Unc-51-like kinase (ULK) family, VPS15 family, WEE family, Wnk family; receptor tyrosine kinases including Type I RTKs: ErbB (epidermal growth factor) receptor family, Type II RTKs: Insulin receptor family, Type III RTKs: PDGFR, CSFR, Kit, FLT3 receptor family, Type IV RTKs: VEGF (vascular endothelial growth factor) receptor family, Type V RTKs: FGF (fibroblast growth factor) receptor family, Type VI RTKs: PTK7/CCK4, Type VII RTKs: Neurotrophin receptor/Trk family, Type VIII RTKs: ROR family, Type IX RTKs: MuSK, Type X RTKs: HGF (hepatocyte growth factor) receptor family, Type XI RTKs: TAM (TYRO3-, AXL- and MER-TK) receptor family, Type XII RTKs: TIE family of angiopoietin receptors, Type XIII RTKs: Ephrin receptor family, Type XIV RTKs: RET, Type XV RTKs: RYK, Type XVI RTKs: DDR (collagen receptor) family, Type XVII RTKs: ROS receptors, Type XVIII RTKs: LMR family, Type XIX RTKs: Leukocyte tyrosine kinase (LTK) receptor family, and Type XX RTKs: STYK1.

Exemplary peptidases and proteinases include, but are not limited to: Aspartic (A) Peptidases (e.g., Pepsin, Presenillin); Cysteine (C) Peptidases (e.g., Papain, Calpain, Ubiquitin C-terminal hydrolase, Ubiquitin-specific protease, Aut2 peptidase, Legumain, Caspase, Gamma-glutamyl hydrolase), Metallo (M) Peptidases (e.g., Prenyl protease 2, Aminopeptidase N, M2: Angiotensin-converting enzyme peptidase unit 1, Matrix metallopeptidase, Astacin/Adamalysin, Neprilysin, Dipeptidyl-peptidase III, Metallo (M) Peptidases, Carboxypeptidase A, pitrilysin, leucyl aminopeptidase, Methionyl aminopeptidase, Aminopeptidase I; Carnosine dipeptidase, Aminopeptidase Y; Membrane dipeptidase; PSMD14 peptidase); Serine (S) Peptidases (e.g., Chymotrypsin, Subtilisin, Prolyl oligopeptidase, Carboxypeptidase Y, Lysosomal Pro-Xaa carboxypeptidase); and Threonine (T) Peptidases.

In some embodiments, a ligand entity is or comprises a receptor ligand, such as a GPCR ligand. According to various embodiments, a variety of freely soluble as well as membrane-associated receptor ligands may be used. In some embodiments, a receptor ligand is a GPCR ligand that associates with one or more of the following exemplary GCPRs: orphan and non-orphan 7TM receptors such as Class A, Class B, Class C, Taste 1 receptors, and other 7TM proteins; 5-Hydroxytryptamine receptors; acetylcholine receptors (muscarinic); adenosine receptors; adhesion class GPCRs; adrenoceptors; angiotensin receptors; apelin receptor; bile acid receptors; bombesin receptors; bradykinin receptors; calcitonin receptors; calcium-sensing receptors; cannabinoid receptors; chemerin receptor; chemokine receptors; cholecystokinin receptors; complement peptide receptors; corticotropin-releasing factor receptors; dopamine receptors; endothelin receptors; estrogen (G protein-coupled) receptor; formylpeptide receptors; free fatty acid receptors; frizzled Class GPCRs; GABAB receptors; galanin receptors; ghrelin receptor; glucagon receptor family receptors such as the: GHRH receptor, GIP receptor, GLP-1 receptor, GLP-2 receptor, glucagon receptor, and secretin receptor; glycoprotein hormone receptors; gonadotrophin-releasing hormone receptors; histamine receptors; hydroxycarboxylic acid receptors; kisspeptin receptor; leukotriene receptors; lysophospholipid (LPA) receptors; lysophospholipid (SIP) receptors; melanin-concentrating hormone receptors; melanocortin receptors; melatonin receptors; metabotropic glutamate receptors; motilin receptor; neuromedin U receptors; neuropeptide FF/neuropeptide AF receptors; neuropeptide S receptor; neuropeptide W/neuropeptide B receptors; neuropeptide Y receptors; neurotensin receptors; opioid receptors; orexin receptors; oxoglutarate receptor; P2Y receptors; parathyroid hormone receptors; peptide P518 receptor; platelet-activating factor receptor; prokineticin receptors; prolactin-releasing peptide receptor; prostanoid receptors; proteinase-activated receptors; relaxin family peptide receptors; somatostatin receptors; succinate receptor; tachykinin receptors; thyrotropin-releasing hormone receptors; trace amine receptor; urotensin receptor; vasopressin and oxytocin receptors; vasoactive intestinal peptide (VIP) and pituitary adenylate cyclase-activating peptide (PACAP) receptors.

In some embodiments, a receptor ligand binds to one or more nuclear hormone receptors including, but not limited to: thyroid hormone receptors; retinoic acid receptors; peroxisome proliferator-activated receptors; rev-erb receptors; retinoic acid-related orphans; liver X receptor-like receptors; vitamin D receptor-like receptors; hepatocyte nuclear factor-4 receptors; retinoid X receptors; testicular receptors; tailless-like receptors; COUP-TF-like receptors; estrogen-related receptors; nerve growth factor IB-like receptors; Fushi tarazu F1-like receptors; germ cell nuclear factor receptors; DAX-like receptors; steroid hormone receptors such as estrogen receptors and 3-Ketosteroid receptors.

In some embodiments, a receptor ligand binds to one or more enzyme-linked receptors. In some embodiments, a receptor ligand binds to one or more catalytic receptors (e.g., receptor kinases). One of skill in the art will recognize that there are at least six known types of enzyme-linked receptors: receptor tyrosine kinases; tyrosine kinase associated receptors; receptor-like tyrosine phosphatases; receptor serine/threonine kinases; receptor guanylyl cyclases and histidine kinase associated receptors. Generally, the majority of these molecules are receptors for growth factors and hormones like epidermal growth factor (EGF), platelet derived growth factor (PDGF), fibroblast growth factor (FGF), hepatocyte growth factor (HGF), insulin, nerve growth factor (NGF) etc.

In some embodiments, a ligand entity is or comprises a transporter ligand. According to certain embodiments, ligand entities may bind to one or more of the following exemplary transporters or members of the following transporter families: ATP-binding cassette transporter family (e.g., ABCA subfamily, ABCB subfamily, ABCC subfamily, ABCD subfamily of peroxisomal ABC transporters, ABCG subfamily); F-type and V-type ATPases (e.g., F-type ATPase, V-type ATPase); P-type ATPases (e.g., Na$^+$/K$^+$-

ATPases, $Ca^{2+}$-ATPases, $H^+/K^+$-ATPases, $Cu^+$-ATPases, Phospholipid-transporting ATPases); and SLC superfamily of solute carriers (e.g., SLC1 family of amino acid transporters, SLC2 family of hexose and sugar alcohol transporters, SLC3 and SLC7 families of heteromeric amino acid transporters (HATs), SLC4 family of bicarbonate transporters, SLC5 family of sodium-dependent glucose transporters, SLC6 neurotransmitter transporter family, SLC8 family of sodium/calcium exchangers, SLC9 family of sodium/hydrogen exchangers, SLC10 family of sodium-bile acid co-transporters, SLC11 family of proton-coupled metal ion transporters, SLC12 family of cation-coupled chloride transporters, SLC13 family of sodium-dependent sulphate/carboxylate transporters, SLC14 family of facilitative urea transporters, SLC15 family of peptide transporters, SLC16 family of monocarboxylate transporters, SLC17 phosphate and organic anion transporter family, SLC18 family of vesicular amine transporters, SLC19 family of vitamin transporters, SLC20 family of sodium-dependent phosphate transporters, SLC22 family of organic cation and anion transporters, SLC23 family of ascorbic acid transporters, SLC24 family of sodium/potassium/calcium exchangers, SLC25 family of mitochondrial transporters, SLC26 family of anion exchangers, SLC27 family of fatty acid transporters, SLC28 and SLC29 families of nucleoside transporters, SLC30 zinc transporter family, SLC31 family of copper transporters, SLC32 vesicular inhibitory amino acid transporter, SLC33 acetyl CoA transporter, SLC34 family of sodium phosphate co-transporters, SLC35 family of nucleotide sugar transporters, SLC36 family of proton-coupled amino acid transporters, SLC37 family of phosphosugar/phosphate exchangers, SLC38 family of sodium-dependent neutral amino acid transporters, SLC39 family of metal ion transporters, SLC40 iron transporter, SLC41 family of divalent cation transporters, SLC42 family of Rhesus glycoprotein ammonium transporters, SLC43 family of large neutral amino acid transporters, SLC44 choline transporter-like family, SLC45 family of putative sugar transporters, SLC46 family of folate transporters, SLC47 family of multidrug and toxin extrusion transporters, SLC48 heme transporter, SLC49 family of FLVCR-related heme transporters, SLC50 sugar transporter, SLC51 family of steroid-derived molecule transporters, SLC52 family of riboflavin transporters).

Those of skill in the art will know of or be able to determine additional ligand entities appropriate for particular application(s). Additional ligand entities may be found, inter alia, at www.sigmaaldrich.com/life-science/biochemicals/biochemical-products.html?TablePage=14572942, and pepnet.com.

Peptidic Ligand Entities

In some embodiments, a ligand entity is or comprises a peptide.

In some embodiments, a peptidic ligand entity has a length between a lower limit length and an upper limit length, the upper limit length being longer than the lower limit length. In some embodiments, the lower limit length is about 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more amino acids. In some embodiments, the upper limit length is about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 22, 230, 24, 250, 260, 270, 280, 290, 300, 350, 400, 450, 500, 550, 600, 650, 700, 750, 800, 850, 900, 950, 1000 or more amino acids. In some embodiments, a peptidic ligand entity has a length within the range of about 10 amino acids to about 500 amino acids. In some embodiments, a peptidic ligand entity has a length within a range of about 20 amino acids to about 400 amino acids.

In some embodiments, a peptidic ligand entity comprises or consists of natural amino acids. In some embodiments, a peptidic ligand entity comprises or consists of non-natural amino acids.

In some embodiments, a peptidic ligand entity has an amino acid sequence that shows significant homology or identity with that of a reference peptide ligand (e.g., that occurs in nature and/or otherwise is known to bind to the target). In some embodiments, a peptidic ligand entity has an amino acid sequence that is identical to that of a reference peptide ligand. In some embodiments, a peptidic ligand entity has an amino acid sequence that is longer at one end or the other than a reference peptide ligand. In some embodiments, a peptidic ligand entity has an amino acid sequence that includes one or several amino acid insertions, deletions, or substitutions as compared with a reference peptide ligand, but typically retains one or more key residues or characteristic sequence elements and/or an overall degree of sequence identity with the peptide ligand. In some embodiments such substitutions are conservative substitutions in that they are substitutions by residues with one or more similar chemical, physical, or biological properties or attributes in common with the residues that they replace. Exemplary suitable peptidic ligand entities may be found, inter alia, in the Phoenix Pharmaceuticals catalog (available at: www.phoenixpeptide.com/catalog).

In some embodiments, a peptidic ligand entity is or comprises a recombinant ligand entity with one or more ends (e.g., an N- or C-terminus) modified to increase amenability to lipidation. In some embodiments, such modifications comprise the introduction or addition or a lipidation site or sequence. In some embodiments, a lipidation site or sequence is a known lipidation site or sequence. Non-limiting exemplary lipidation sites, sequences, and/or mechanisms include: sites amenable to prenylation (e.g., addition of either a farnesyl or geranylgeranyl isoprenoid to one or more conserved cysteine residues at or near the C-terminus of a protein) such as peptides comprising at least one CaaX motif and/or CC- or CxC-cmotif; myristoylation (e.g., N-myristoylation); palmitoylation (e.g., S-palmitoylation); and/or acylation (e.g., O-acylation). Additional lipidation sites, sequences and mechanisms may be found, inter alia, in Zhang and Casey, Protein prenylation: molecular mechanisms and functional consequences, 1996, *Annu. Rev. Biochem.*, 65: 241-269; and Hang H C, Exploring protein lipidation with chemical biology, 2011, *Chem. Rev.*, 111: 6341-6358; Nadolski and Linder, Protein lipidation, 2007, *FEBS Journal*, 274: 5202-5210, the disclosures of which are hereby incorporated by reference in their entirety.

In some embodiments, a recombinant ligand entity is modified to increase amenability to lipidation at a position other than an end (e.g., other than an N- or C-terminus). In some embodiments, a peptidic ligand entity is or comprises a non-recombinant ligand entity. In some embodiments, a non-recombinant ligand entity comprises one or more modifications, for example, to one or more of the N- or C-terminus.

In some embodiments, a peptidic ligand entity is or comprises one or more sequence elements. In some embodiments, a sequence element is or comprises a lipidation site. In some embodiments, a sequence element is a particular sequence that is characteristic of a particular class or subclass of ligand entity (e.g., GPCR, growth factor, venom).

In some embodiments, peptidic ligand entities comprise or consist of naturally occurring amino acid residues; in some embodiments, peptidic ligand entities comprises or consist of non-naturally-occurring amino acid residues or amino acid residue analogs.

In some embodiments, peptidic ligand entities comprise or consist of residues having one or several chemical modifications as compared with a reference residue structure (e.g., with a naturally-occurring amino acid, a non-naturally-occurring amino acid, or an amino acid analog). To give but a few examples, in some embodiments, peptidic ligand entities comprise or consist of residues having one or more altered (e.g., added or altered) pendant groups such as, for example, sugars, lipids, etc.

In some embodiments, a peptidic ligand is or comprises a toxin. A variety of peptide toxins, and derivatives thereof, are known in the art. In some embodiments, a toxin is a venom. Those of skill in the art will recognize that there are more than 173,000 species of venomous animals, and more than 40 million peptides and combinations of peptides that comprise one or more venoms. It is contemplated that any venom or venom peptide is compatible with some embodiments, with certain venoms or venom peptides benefitting from, or requiring, modifications in order to be suitable for lipidation. In particular, venoms with recognized beneficial effects, including those that have been formulated as therapeutic molecules, are desirable ligand entities according to various embodiments. By way of non-limiting example, certain snake venoms (e.g., those formulated as CAPTOPRIL®, EPTIFIBATIDE®, or TIROFIBAN®), cone snail venoms (e.g., that formulated as PRIALT®), and toxic lizard salivas (e.g., such as that formulated as BYETTA®) may be used in some embodiments as a ligand entity. Other suitable venom ligand entities may be found through the "Venoms for Health" project sponsored by the European Commission under the 7$^{th}$ Framework Program (see www.venomics.eu).

In some embodiments, a peptidic ligand is or comprises a GPCR ligand. A variety of GPCR peptide ligands, and derivatives thereof, are known in the art. Exemplary such GPCR ligands include those disclosed herein, for example, chemerin, substance P, CCL20, met-enkephalin, CGRP, BAMS-22, γ1MSH, γ2MSH, NPFF, and FMRF. In some embodiments, a GPCR ligand entity binds to one or more GPCR receptors. Alternatively or additionally, exemplary peptide GPCR ligands are listed below in Table 1.

In some embodiments, a peptidic ligand entity is or comprises a precursor peptide. Another of the advantages of some embodiments is that lipidation of a precursor peptide may allow the precursor peptide to exert a desired biological effect, for example, an effect normally associated with the activated form of the peptide, without undergoing the modifications normally thought to be required to activate the precursor peptide. In some embodiments, a soluble lipidated precursor peptide is able to bind to its target and exert a biological effect when the precursor peptide alone is not able to do so.

In some embodiments, a ligand entity is or comprises a peptide with an amino acid sequence showing at least 40% sequence identity to one or more reference peptides. In some embodiments, a ligand entity is or comprises a peptide showing at least 40%, 50%, 60%, 70%, 75%, 80%, 85%, 90%, 95%, 99% or greater sequence identity to one or more reference peptides. In some embodiments, a ligand entity is or comprises a peptide showing at least 70% sequency identity to one or more characteristic sequence elements of a reference peptide. In some embodiments, a ligand entity is or comprises a peptide showing at least 75%, 80%, 85%, 90%, 95%, or 99% or greater sequence identity to one or more characteristic sequence elements of a reference peptide. In some embodiments, a characteristic sequence element may be characterized through the use of alanine scanning or other technique for defining characteristic sequence elements. In some embodiments, a reference peptide may be or comprise one of the peptides listed in Table 1.

In some embodiments, a ligand entity is or comprises a variant of a reference peptide that differs from the reference peptide by no more than 30 amino acids. In some embodiments, a variant differs from a reference peptide by no more than 25, 20, 15, 10, 9, 8, 7, 6, 5, 4, 3, 2, or 1 amino acid. In some embodiments, a ligand entity is or comprises a variant of a reference peptide that differs from a characteristic sequence element of the reference peptide by no more than 30 amino acids. In some embodiments, a variant differs from a characteristic sequence element of a reference peptide by no more than 25, 20, 15, 10, 9, 8, 7, 6, 5, 4, 3, 2, or 1 amino acid. In some embodiments, a reference peptide may be or comprise one of the peptides listed in Table 1.

In some embodiments, the present invention demonstrates that a given peptidic ligand entity may have a preferred lipidation site for use in accordance with the present invention.

TABLE 1

| Exemplary Peptidic Ligands* | |
|---|---|
| Name | |
| ACTH {Sp: Human} | ACTH (1-39), adrenocorticotrophin, adrenocorticotropic hormone, adrenocorticotropic hormone (1-39), corticotropin |
| ACTH {Sp: Mouse, Rat} | ACTH (1-39), adrenocorticotrophin, adrenocorticotropic hormone (1-39), corticotropin |
| activin A {Sp: Human} | |
| activin AB {Sp: Human} | |
| activin B {Sp: Human} | |
| adiponectin {Sp: Human} | ACRP30, adipocyte, C1Q and collagen domain-containing protein, flAdipo, full-length adiponectin, gelatin-binding protein |
| ADP-ribosylation factor 1 {Sp: Human} | Arf1, ADP-ribosylation factor, ARF, ARF1, ARF-1 |
| adrenomedullin {Sp: Human} | AM, adrenomedullin (human), human adrenomedullin |
| adrenomedullin {Sp: Mouse} | AM, mouse adrenomedullin |
| adrenomedullin {Sp: Rat} | AM, rat adrenomedullin |
| adrenomedullin 2/intermedin {Sp: Human} | AM2/IMD |
| adrenomedullin 2/intermedin {Sp: Mouse} | |
| adrenomedullin 2/intermedin {Sp: Rat} | |
| agouti {Sp: Human} | |

TABLE 1-continued

Exemplary Peptidic Ligands*
Name

| | |
|---|---|
| agouti {Sp: Mouse} | agouti-signaling protein, ASIP, ASP |
| agouti-related protein {Sp: Human} | AGRP, agouti-related peptide |
| alarin {Sp: Rat} | |
| amphiregulin {Sp: Human} | AREG, colorectal cell-derived growth factor, CRDGF |
| amylin {Sp: Human} | AMY, AMY, islet amyloid polypeptide |
| amylin {Sp: Mouse, Rat} | AMY, rat amylin |
| amyloid β {Sp: Human} | beta-amyloid protein |
| angiopoietin-1 {Sp: Human} | ANG-1 |
| angiopoietin-2 {Sp: Human} | Ang2, ANG-2, angiopoietin 2 |
| angiopoietin-4 {Sp: Human} | ANG-4 |
| angiotensin-(1-7) {Sp: Human, Mouse, Rat} | ang 1-7, angiotensin 1-7 |
| angiotensin-(1-9) {Sp: Human, Mouse, Rat} | ang 1-9, angiotensin 1-9 |
| angiotensin A {Sp: Human} | ang A |
| angiotensin I {Sp: Human, Mouse, Rat} | ang I |
| angiotensin II {Sp: Human, Mouse, Rat} | ang II |
| angiotensin III {Sp: Human, Mouse, Rat} | ang III |
| angiotensin IV {Sp: Human, Mouse, Rat} | AT II (3-8) |
| annexin I {Sp: Human} | annexin 1, ANXA1 |
| annexin I-(2-26) {Sp: Human} | annexin-derived peptide, annexin I, Ac2-26, ANXA1-derived peptide |
| annexin I {Sp: Mouse} | |
| annexin I {Sp: Rat} | |
| apelin-36 {Sp: Human} | |
| apelin-13 {Sp: Human, Mouse, Rat} | [Pyr1]-Apelin-13 |
| apelin-17 {Sp: Human, Mouse, Rat} | K17F |
| apelin-36 {Sp: Mouse, Rat} | |
| APRIL {Sp: Human} | A proliferation-inducing ligand, CD256, TALL2, TNF-and APOL-related leukocyte expressed ligand 2, TNF-related death ligand 1, TNFSF13, TNFSF13A, TRDL-1, ZTNF2 |
| artemin {Sp: Human} | ARTN, enovin, neublastin |
| atrial natriuretic peptide {Sp: Human} | ANP, ANF, atrial natriuretic factor |
| B | |
| BAFF {Sp: Human} | B cell-activating factor, B lymphocyte stimulator, BLyS, CD257 antigen, dendritic cell-derived TNF-like molecule, DTL, TALL-1, THANK, TNF- and APOL-related leukocyte expressed ligand 1, TNFSF13B, Tumor necrosis factor ligand superfamily member 13b, membrane form, zTNF4 |
| BAM8-22 {Sp: Human} | 8-22-BAM, BAM-15, BAM (8-22), bovine adrenal medulla peptide 8-22 |
| B and T lymphocyte attenuator {Sp: Human} | BTLA, B-and T-lymphocyte-associated protein, B-and T-lymphocyte attenuator, CD_antigen = CD272 |
| 4-1BB ligand {Sp: Human} | CDw137L, TNFSF9 |
| BDNF {Sp: Human} | brain-derived neurotrophic factor |
| bestrophin-3 {Sp: Human} | vitelliform macular dystrophy 2-like protein 3 |
| betacellulin {Sp: Human} | BTC |
| beta-defensin 4A {Sp: Human} | BD-2, beta-defensin 2, DEFB-2, hBD-2, HBD2, SAP1, skin-antimicrobial peptide 1 |
| BH3 interacting-domain death agonist {Sp: Human} | BID, Bid, BID |
| big dynorphin {Sp: Human, Mouse, Rat} | big dyn |
| Big LEN {Sp: Mouse} | Big LEN, b-LEN, SAAS CT(25-40) |
| BMP-10 {Sp: Human} | BMP10, bone morphogenetic protein 10 |
| BMP-2 {Sp: Human} | BMP2, BMP-2A, bone morphogenetic protein 2, bone morphogenetic protein 2A |
| BMP-4 {Sp: Human} | BMP-2B, BMP4, bone morphogenetic protein 2B, bone morphogenetic protein 4 |
| BMP-5 {Sp: Human} | BMP5, bone morphogenic protein 5 |
| BMP-6 {Sp: Human} | BMP6, bone morphogenetic protein 6, VG-1-R, VG-1-related protein, VGR-1 |
| BMP-7 {Sp: Human} | BMP7, bone morphogenetic protein 7, OP-1, osteogenic protein 1 |
| BMP-9 {Sp: Human} | BMP9, bone morphogenetic protein 9, GDF-2, growth/differentiation factor 2 |
| BMP-8A {Sp: Human} | BMP8A, bone morphogenetic protein 8A |
| BMP-8B {Sp: Human} | BMP-8, BMP8B, bone morphogenetic protein 8B, OP-2, osteogenic protein 2 |
| bradykinin {Sp: Human, Mouse, Rat} | BK, kallidin I, kinin 9 |
| brain natriuretic peptide {Sp: Human} | BNP, BNP(1-32), BNP-32, brain natriuretic peptide, brain natriuretic peptide 32 |
| C | |
| C3a {Sp: Human} | C3a anaphylatoxin, C3a anaphylatoxin polypeptide, complement component C3a |
| C4a {Sp: Human} | acidic complement C4, C3 and PZP-like alpha-2-macroglobulin domain-containing protein 2, complement C4-A |
| C5a {Sp: Human} | C5a anaphylatoxin, complement component 5a, human complement protein |
| C3a {Sp: Mouse} | C3a anaphylatoxin, complement component C3a |
| C5a {Sp: Mouse} | C5a anaphylatoxin, complement component C5a |

TABLE 1-continued

| | Exemplary Peptidic Ligands* Name |
|---|---|
| C3a {Sp: Rat} | C3a anaphylatoxin, C3a anaphylatoxin polypeptide, complement component C3a |
| C5a {Sp: Rat} | C5a anaphylatoxin, complement component C5a |
| C3a des Arg {Sp: Human} | |
| C5a des-Arg {Sp: Human} | C5a des-Arg$^{74}$ |
| calcitonin {Sp: Human} | CT, calcitonin (human), Human CT |
| calcitonin {Sp: Mouse, Rat} | CT |
| calmodulin {Sp: Human} | calcium-calmodulin, CaM, Ca$^{2+}$/calmodulin, Ca$^{2+}$/CaM |
| cardiotrophin-1 {Sp: Human} | CTF1, B-cell stimulatory factor 3, BSF3, CT-1 |
| cardiotrophin-like cytokine factor 1 {Sp: Human} | CLCF1, B-cell-stimulating factor 3, BSF-3, cardiotrophin-like cytokine, NNT-1, novel neurotrophin-1 |
| β-catenin {Sp: Human} | catenin beta-1 |
| cathepsin G {Sp: Human} | |
| cathepsin G {Sp: Mouse} | |
| cathepsin G {Sp: Rat} | |
| CCK-33 {Sp: Human} | CCRIS 3307, Cecekin vitrum, cholecystokinin, cholecystokinin 33, cholecystokinin triacontatriapeptide |
| CCK-4 {Sp: Human} | cholecystokinin fragment 30-33 amide |
| CCK-8 {Sp: Human, Mouse, Rat} | CCK-8 (sulphated), cholecystokinin 8, cholecystokinin fragment 26-33 amide (sulphated), cholecystokinin octapeptide, pancreozymin C-terminal octapeptide, sincalide |
| CCK-33 {Sp: Mouse} | |
| CCK-33 {Sp: Rat} | |
| CCL1 {Sp: Human} | I309, I-309, P500, TCA-3 |
| CCL11 {Sp: Human} | eotaxin |
| CCL13 {Sp: Human} | MCP-4, monocyte chemotactic protein-4 |
| CCL14 {Sp: Human} | CCL14a, CKβ1, haemofiltrate CC chemokine 1, HCC-1, HCC-1(1-74), MCIF |
| CCL15 {Sp: Human} | HCC-2, Lkn-1 [Leukotactin-1], macrophage inflammatory protein-1δ, MIP-1δ, MIP-5 |
| CCL16 {Sp: Human} | CKb12, HCC-4, LCC-1, LEC |
| CCL17 {Sp: Human} | TARC, thymus-and activation-regulated chemokine |
| CCL19 {Sp: Human} | β-chemokine exodus-3, ckβ11, CK β-11, EBI-1-Ligand Chemokine, ELC, MIP-3β |
| CCL2 {Sp: Human} | MCAF, MCP-1, monocyte chemotactic protein-1 |
| CCL20 {Sp: Human} | LARC, liver and activation-regulated chemokine, macrophage inflammatory protein-3α, MIP-3α |
| CCL21 {Sp: Human} | 6Ckine, ckβ9, Secondary lymphoid-tissue chemokine, SLC, TCA-4 |
| CCL22 {Sp: Human} | abcd-1, dc/β-ck, macrophage-derived chemokine, MDC, STCP1 |
| CCL23 {Sp: Human} | ckβ8-1, MPIF-1, myeloid progenitor inhibitor factor-1 |
| CCL24 {Sp: Human} | eotaxin-2, MPIF-2 |
| CCL25 {Sp: Human} | TECK, thymus-expressed chemokine |
| CCL26 {Sp: Human} | eotaxin-3, MIP-4α, PTEC |
| CCL27 {Sp: Human} | ALP, CTACK, cutaneous T-cell attracting chemokine, Eskine |
| CCL28 {Sp: Human} | CC chemokine CCL28, MEC, mucosae-associated epithelial chemokine |
| CCL3 {Sp: Human} | macrophage inflammatory protein-1α, MIP-1α |
| CCL4 {Sp: Human} | HC21, macrophage inflammatory protein-1β, MIP-1β, Small inducible cytokine A4 |
| CCL5 {Sp: Human} | eosinophil chemotactic cytokine [EoCP], RANTES, regulated upon activation normal T cell expressed and secreted |
| CCL7 {Sp: Human} | MCP-3, monocyte chemotactic protein-3 |
| CCL8 {Sp: Human} | MCP-2, monocyte chemotactic protein-2 |
| CCL1 {Sp: Mouse} | |
| CCL11 {Sp: Mouse} | murine eotaxin |
| CCL19 {Sp: Mouse} | |
| CCL2 {Sp: Mouse} | |
| CCL20 {Sp: Mouse} | |
| CCL22 {Sp: Mouse} | |
| CCL24 {Sp: Mouse} | |
| CCL25 {Sp: Mouse} | |
| CCL27 {Sp: Mouse} | |
| CCL28 {Sp: Mouse} | |
| CCL3 {Sp: Mouse} | |
| CCL4 {Sp: Mouse} | |
| CCL7 {Sp: Mouse} | |
| CCL8 {Sp: Mouse} | |
| CCL5 {Sp: Mouse, Rat} | |
| CCL11 {Sp: Rat} | |
| CCL2 {Sp: Rat} | |
| CCL20 {Sp: Rat} | |
| CCL3 {Sp: Rat} | |
| CCL4 {Sp: Rat} | |
| CCL7 {Sp: Rat} | |
| CD70 {Sp: Human} | CD27 ligand, Ki-24, TNFSF7 |
| CD30 ligand {Sp: Human} | CD153, TNFSF8 |

TABLE 1-continued

| | Exemplary Peptidic Ligands*<br>Name |
|---|---|
| CD40 ligand {Sp: Human} | CD154, CD40 ligand, membrane form, gp39, TNF-related activation protein, TNFSF5, TRAP |
| α-CGRP {Sp: Human} | α-calcitonin gene-related peptide (human), αCGRP, calcitonin gene-related peptide 1, CGRP, human α-calcitonin gene-related peptide |
| β-CGRP {Sp: Human} | β-calcitonin gene-related peptide, βCGRP, calcitonin gene-related peptide 2, human β-calcitonin gene-related peptide |
| β-CGRP {Sp: Mouse} | β-calcitonin gene-related peptide, βCGRP, calcitonin gene-related peptide 2, human β-calcitonin gene-related peptide |
| α-CGRP {Sp: Mouse, Rat} | αCGRP, rat α-calcitonin gene-related peptide |
| β-CGRP {Sp: Rat} | pCGRP, rat β-calcitonin gene-related peptide |
| chemerin {Sp: Human} | RARRES2, retinoic acid receptor responder protein 2, tazarotene-induced gene 2 protein, TIG2 |
| chondroitin sulphate proteoglycan 3 {Sp: Human} | CSPG3 |
| choriomammotropin {Sp: Human} | chorionic somatomammotropin hormone, CSH, lactogen |
| chorionic gonadotropin beta subunit {Sp: Human} | CG-beta, choriogonadotropin subunit beta, chorionic gonadotrophin chain beta |
| chorionic somatomammotropin hormone-like 1 {Sp: Human} | chorionic somatomammotropin-like, lactogen-like |
| chromogranin A {Sp: Human} | CgA, parathyroid secretory protein 1, pituitary secretory protein I, SP-1 |
| ciliary neurotrophic factor {Sp: Human} | CNTF |
| COL1A1 {Sp: Human} | alpha-1 type I collagen, collagen alpha-1(I) chain |
| COL2A1 {Sp: Human} | alpha-1 type II collagen, collagen alpha-1(II) chain |
| COL3A1 {Sp: Human} | collagen alpha-1(III) chain |
| COL4A1 {Sp: Human} | collagen alpha-1(IV) chain |
| contactin-1 {Sp: Human} | |
| contactin-3 {Sp: Human} | BIG-1, PANG |
| contactin-4 {Sp: Human} | BIG-2 |
| contactin-5 {Sp: Human} | hNB-2, NB-2 |
| contactin-6 {Sp: Human} | NB-3, neural adhesion molecule |
| CRAMP {Sp: Mouse} | cathelin-related antimicrobial peptide |
| CRCF1/CLCF1 heterodimer {Sp: Human} | |
| CRF {Sp: Human, Mouse, Rat} | corticoliberin, corticotropin-releasing factor, corticotropin-releasing hormone, CRH |
| CST-17 {Sp: Human} | cortistatin-17 |
| CST-14 {Sp: Mouse, Rat} | cortistatin, cortistatin-14 |
| C-type natriuretic peptide {Sp: Human} | CNP, CNP-22 |
| CXCL1 {Sp: Human} | GROα, melanocyte growth-stimulator activity, MGSA, MIP-2 |
| CXCL10 {Sp: Human} | CRG-2, IP-10 |
| CXCL11 {Sp: Human} | b-R1, chemokine (C-X-C motif) ligand 11, CXCL11_(22-73)_(52AA), H174, IP9, ITAC, I-TAC, SCYB11, SCYB9B, small inducible cytokine subfamily B (Cys-X-Cys), member 11 |
| CXCL13 {Sp: Human} | ANGIE, ANGIE2, BCA-1, B-cell chemoattractant, BLC, BLR1L |
| CXCL14 {Sp: Human} | BMAC, BRAK |
| CXCL16 {Sp: Human} | CXCLG16, SRPSOX, SR-PSOX |
| CXCL17 {Sp: Human} | C-X-C motif chemokine 17, dendritic cell and monocyte chemokine-like protein, DMC, VEGF co-regulated chemokine 1 |
| CXCL2 {Sp: Human} | GROβ, MIP-2α |
| CXCL3 {Sp: Human} | GROγ, MIP-2β |
| CXCL4 {Sp: Human} | PF4, platelet factor 4 |
| CXCL5 {Sp: Human} | ENA-78 |
| CXCL6 {Sp: Human} | CKA-3, GCP-2 |
| CXCL7 {Sp: Human} | NAP-2, PPBP, pro-platelet basic protein (chemokine (C-X-C motif) ligand 7) |
| CXCL8 {Sp: Human} | IL-8, interleukin-8 |
| CXCL9 {Sp: Human} | crg-10, Humig, MIG, SCYB9 |
| CX3CL1 {Sp: Human} | fractalkine, neurotactin |
| CXCL1 {Sp: Mouse} | mouse KC |
| CXCL10 {Sp: Mouse} | |
| CXCL11 {Sp: Mouse} | |
| CXCL13 {Sp: Mouse} | |
| CXCL15 {Sp: Mouse} | lungkine (mouse) |
| CXCL16 {Sp: Mouse} | |
| CXCL2 {Sp: Mouse} | macrophage inflammatory protein 2, Mip-2, MIP2 |
| CXCL3 {Sp: Mouse} | |
| CXCL5 {Sp: Mouse} | |
| CXCL9 {Sp: Mouse} | |
| CX3CL1 {Sp: Mouse} | |
| CXCL1 {Sp: Rat} | CINC, CINC-1, cytokine-induced neutrophil chemoattractant GROα, growth-regulated alpha protein, macrophage inflammatory protein-2, platelet-derived growth factor-inducible protein KC |
| CXCL10 {Sp: Rat} | |
| CXCL16 {Sp: Rat} | |
| CXCL2 {Sp: Rat} | |
| CXCL3 {Sp: Rat} | |
| CXCL5 {Sp: Rat} | |
| CX3CL1 {Sp: Rat} | |

TABLE 1-continued

| | Exemplary Peptidic Ligands*<br>Name |
|---|---|
| cytokine domain of tyrosyl tRNA synthetase {Sp: Human} | cytoplasmic, tyrosine tRNA ligase 1, tyrosyl-tRNA synthetase, tyrRS, YRS, YTS |
| cytokine receptor-like factor 1 {Sp: Human} | CRLF1, CISS, CISS1, CLF, CLF-1, cytokine receptor-like factor 1, NR6 |

D

| | |
|---|---|
| [des-Arg9]bradykinin {Sp: Human, Mouse, Rat} | [des-Arg$^9$]BK |
| [des-Arg10]kallidin {Sp: Human} | kallidin$_{1-9}$, Lys-[des-Arg$^9$]BK, [Lys,des-Arg$^9$]bradykinin, Lys-[des-Arg$^9$]-bradykinin |
| des-Br-neuropeptide B-23 {Sp: Human} | des-Br-NPB-23 |
| des-Br-neuropeptide B-29 {Sp: Human} | des-Br-NPB-29 |
| [des-Gln14]ghrelin {Sp: Human} | des-Gln$^{14}$-ghrelin |
| [des-Gln14]ghrelin {Sp: Mouse, Rat} | |
| [des-octanoyl]ghrelin {Sp: Human} | [des-octanoyl] ghrelin, des-octanoyl ghrelin |
| Dickkopf 1 {Sp: Human} | Dickkopf-related protein 1, Dkk 1, DKK 1, hDkk-1, SK |
| dynorphin A {Sp: Human, Mouse, Rat} | dynA, dynorphin 1-17, dynorphin A (1-17) |
| dynorphin A-(1-13) {Sp: Human, Mouse, Rat} | dynorphin 1-13, dynorphin A (1-13) |
| dynorphin A-(1-8) {Sp: Human, Mouse, Rat} | dynorphin A (1-8) |
| dynorphin B {Sp: Human, Mouse, Rat} | rimorphin |

E

| | |
|---|---|
| ectodysplasin A1 {Sp: Human} | ectodysplasin-A isoform 1, ectodysplasin-A, membrane form, membrane isoform of ectodysplasin-A |
| ectodysplasin A2 {Sp: Human} | ectodysplasin-A, secreted form, secreted form of ectodysplasin-A |
| EGF {Sp: Human} | epidermal growth factor, urogastrone |
| endomorphin-1 {Sp: Human} | (2S)-1-[(2S)-2-amino-3-(4-hydroxphenyl)propanoyl]-N-[(1S)-1-[[(1S)-1-carbamoyl-2-phenyl-ethyl]carbamoyl]-2-(1H-indol-3-yl)ethyl]pyrrolidine-2-carboxamide |
| endomorphin-2 {Sp: Human} | |
| β-endorphin {Sp: Human} | β-end |
| β-endorphin {Sp: Mouse} | β-end |
| β-endorphin {Sp: Rat} | β-end |
| endothelin-2 {Sp: Human} | ET-2 |
| endothelin-1 {Sp: Human, Mouse, Rat} | ET-1 |
| endothelin-3 {Sp: Human, Mouse, Rat} | ET-3 |
| ephrin-A1 {Sp: Human} | EFNA1, ECKLG, EPH-related receptor tyrosine kinase ligand 1, EPLG1, immediate early response protein B61, LERK1, TNFAIP4, TNF alpha-induced protein 4, tumor necrosis factor alpha-induced protein 4 |
| ephrin-A2 {Sp: Human} | EFNA2, ELF-1, EPH-related receptor tyrosine kinase ligand 6, EPLG6, HEK7-L, HEK7 ligand, LERK6 |
| ephrin-A3 {Sp: Human} | EFNA3, EFL-2, Ehk1-L, EHK1 ligand, EPH-related receptor tyrosine kinase ligand 3, EPLG3, LERK3 |
| ephrin-A4 {Sp: Human} | EFNA4, EPH-related receptor tyrosine kinase ligand 4, EPLG4, LERK4, LERK-4 |
| ephrin-A5 {Sp: Human} | EFNA5, AF1, AL-1, EPH-related receptor tyrosine kinase ligand 7, EPLG7, LERK7, LERK-7 |
| ephrin-B1 {Sp: Human} | EFNB1, EFL-3, ELK-L, ELK ligand, EPH-related receptor tyrosine kinase ligand 2, LERK-2 |
| ephrin-B2 {Sp: Human} | EFNB2, EPH-related receptor tyrosine kinase ligand 5, HTK-L, HTK ligand, LERK-5 |
| ephrin-B3 {Sp: Human} | EFNB3, EPH-related receptor transmembrane ligand ELK-L3, EPH-related receptor tyrosine kinase ligand 8, LERK-8 |
| epigen {Sp: Human} | EPG, epithelial mitogen |
| epiregulin {Sp: Human} | |
| erythropoietin {Sp: Human} | EPO |

F

| | |
|---|---|
| Fas ligand {Sp: Human} | Apol L, apoptosis antigen ligand, CD178, CD95L, TNFSF6, tumor necrosis factor ligand superfamily member 6, membrane form |
| FGF-1 {Sp: Human} | acidic fibroblast growth factor, aFGF, beta-endothelial cell growth factor, ECGF-beta, fibroblast growth factor 1, HBGF-1, heparin-binding growth factor 1 |
| FGF-2 {Sp: Human} | basic fibroblast growth factor, bFGF, fibroblast growth factor 2, HBGF-2, heparin-binding growth factor 2 |
| FGF-4 {Sp: Human} | fibroblast growth factor 4, HBGF-4, heparin-binding growth factor 4, heparin secretory-transforming protein 1, HST, HST-1, HSTF-1, transforming protein KS3 |
| FGF-5 {Sp: Human} | fibroblast growth factor 5, HBGF-5, heparin-binding growth factor 5, Smag-82 |
| FGF-6 {Sp: Human} | fibroblast growth factor 6, HBGF-6, heparin-binding growth factor 6, heparin secretory-transforming protein 2, HST-2, HSTF-2 |
| FGF-7 {Sp: Human} | fibroblast growth factor 7, HBGF-7, heparin-binding growth factor 7, keratinocyte growth factor |
| FGF-8 {Sp: Human} | AIGF, androgen-induced growth factor, fibroblast growth factor 8, HBGF-8, heparin-binding growth factor 8 |

TABLE 1-continued

Exemplary Peptidic Ligands*
Name

| | |
|---|---|
| FGF-9 {Sp: Human} | fibroblast growth factor 9, GAF, glia-activating factor, HBGF-9, heparin-binding growth factor 9 |
| fibrinogen {Sp: Human} | |
| fibrinogen alpha chain {Sp: Human} | |
| fibrinogen beta chain {Sp: Human} | |
| fibrinogen gamma chain {Sp: Human} | |
| fibronectin {Sp: Human} | |
| F2L {Sp: Human} | |
| FLICE-like inhibitory protein {Sp: Human} | FLIP, CASP8 and FADD-like apoptosis regulator |
| FLICE-like inhibitory protein subunit p12 {Sp: Human} | FLIP subunit p12, CASP8 and FADD-like apoptosis regulator subunit p12 |
| FLICE-like inhibitory protein subunit p43 {Sp: Human} | FLIP subunit p43, CASP8 and FADD-like apoptosis regulator subunit p43 |
| FLRT3 {Sp: Rat} | fibronectin-like domain-containing leucine-rich transmembrane protein 3, leucine-rich repeat transmembrane protein FLRT3 |
| Fms-related tyrosine kinase 3 ligand {Sp: Human} | FLT3L, Flt3 ligand, SL cytokine |
| follistatin {Sp: Human} | activin-binding protein, FS |
| FSH {Sp: Human} | follitropin, human follicle stimulating hormone |
| FSH {Sp: Mouse} | follicle stimulating hormone |
| FSH {Sp: Rat} | follicle stimulating hormone |
| FSH β subunit {Sp: Human} | follicle-stimulating hormone beta subunit, follitropin beta chain, follitropin subunit beta, FSHB, FSH-B, FSH-beta, FSH beta subunit |
| FSH β subunit {Sp: Mouse} | follicle-stimulating hormone beta subunit, follitropin beta chain, follitropin subunit beta, FSHB, FSH-B, FSH-beta, FSH beta subunit |
| FSH β subunit {Sp: Rat} | follicle-stimulating hormone beta subunit, follitropin beta chain, follitropin subunit beta, FSHB, FSH-B, FSH-beta, FSH beta subunit |

G

| | |
|---|---|
| galanin {Sp: Human} | |
| galanin {Sp: Mouse, Rat} | |
| galanin-like peptide {Sp: Human} | GALP |
| galanin-like peptide {Sp: Mouse} | GALP |
| galanin-like peptide {Sp: Rat} | GALP |
| galectin-1 {Sp: Human} | GBP |
| galectin-3 {Sp: Human} | galectin 3, GALIG, LGALS2, MAC-2 |
| galectin-3 binding protein {Sp: Human} | BTBD17B, L3 antigen, Mac-2-binding protein, MAC-2-BP, TANGO10B |
| gastric inhibitory polypeptide {Sp: Human} | GIP, gastric inhibitory peptide, $GIP_{1-42}$, glucose-dependent insulinotropic polypeptide |
| gastric inhibitory polypeptide {Sp: Mouse} | GIP, gastric inhibitory peptide, glucose-dependent insulinotropic pol peptide |
| gastric inhibitory polypeptide {Sp: Rat} | GIP, gastric inhibitory peptide, glucose-dependent insulinotropic polypeptide |
| gastrin-17 {Sp: Human} | gastrin, gastrin I |
| gastrin-17 {Sp: Mouse} | |
| gastrin-17 {Sp: Rat} | |
| gastrin-releasing peptide {Sp: Human} | GRP |
| gastrin-releasing peptide {Sp: Mouse, Rat} | GRP |
| G-CSF {Sp: Human} | colony stimulating factor 3 (granulocyte), CSF3, granulocyte colony stimulating factor, granulocyte colony stimulating factor, MGC45931, pluripoietin |
| GDNF {Sp: Human} | astrocyte-derived trophic factor, ATF, glial cell-derived neurotrophic factor, hGDNF |
| ghrelin {Sp: Human} | |
| ghrelin {Sp: Mouse, Rat} | |
| GHRH {Sp: Human} | GHRF, GHRH (1-44), GRF, GRF (1-44), growth hormone-releasing factor, growth hormone-releasing hormone (1-44) amide, somatocrinin, somatoliberin, somatorelin |
| GHRH {Sp: Mouse} | growth hormone-releasing factor, somatoliberin (mouse) |
| GHRH {Sp: Rat} | growth hormone-releasing factor, somatoliberin (rat) |
| globular adiponectin {Sp: Human} | ACRP30, adipocyte, C1Q and collagen domain-containing protein, gAdipo, gelatin-binding protein |
| glucagon {Sp: Human, Mouse, Rat} | |
| glucagon-like peptide 2 {Sp: Human} | GLP-2, GLP-2 (1-33), glucagon-like peptide 2 (1-33) |
| glucagon-like peptide 2-(3-33) {Sp: Human} | GLP-2 (3-33) |
| glucagon-like peptide 1 {Sp: Human, Mouse, Rat} | GLP-1, GLP1 |
| glucagon-like peptide-1-(7-37) {Sp: Human, Mouse, Rat} | GLP-1-(7-37), GLP-1(7-37) |
| glucagon-like peptide 2 {Sp: Mouse} | GLP-2, GLP-2 (1-33) |
| glucagon-like peptide 2-(3-33) {Sp: Mouse} | GLP-2 (3-33) |
| glucagon-like peptide 2 {Sp: Rat} | GLP-2, GLP-2 (1-33), glucagon-like peptide 2 (1-33) |
| glucagon-like peptide 2-(2-33) {Sp: Rat} | GLP-2 (2-33), rat glucagon-like peptide 2 (2-33) |
| glucagon-like peptide 2-(3-33) {Sp: Rat} | GLP-2 (3-33) |
| glucagon-like peptide 1-(7-36) amide {Sp: Human, Mouse, Rat} | GLP-1, GLP-1(7-36)amide, glucagon-like peptide 1 |

TABLE 1-continued

| | Exemplary Peptidic Ligands* Name |
|---|---|
| glycoprotein hormone common alpha subunit {Sp: Human} | alpha polypeptide, chorionic gonadotropin alpha chain, common alpha subunit, follicle-stimulating hormone alpha subunit, FSH alpha chain, glycoprotein hormones alpha polypeptide, GPHa, GPHA1, HCG alpha chain, LH alpha chain, luteinizing hormone alpha chain, TSH alpha chain |
| glycoprotein hormone common alpha subunit {Sp: Mouse} | alpha polypeptide, chorionic gonadotropin alpha chain, common alpha subunit, follicle-stimulating hormone alpha subunit, FSH alpha chain, glycoprotein hormones alpha polypeptide, GPHa, GPHA1, HCG alpha chain, LH alpha chain, luteinizing hormone alpha chain, TSH alpha chain |
| glycoprotein hormone common alpha subunit {Sp: Rat} | alpha polypeptide, chorionic gonadotropin alpha chain, common alpha subunit, follicle-stimulating hormone alpha subunit, FSH alpha chain, glycoprotein hormones alpha polypeptide, GPHa, GPHA1, HCG alpha chain, LH alpha chain, luteinizing hormone alpha chain, TSH alpha chain |
| GM-CSF {Sp: Human} | colony-stimulating factor, CSF, CSF2, granulocyte-macrophage CSF, molgramostin, sargramostim |
| GnRH I {Sp: Human, Mouse, Rat} | GnRH, GnRH (natural sequence), gonadoliberin, gonadotropin releasing hormone, LH-RH |
| GnRH II {Sp: Human} | gonadoliberin-2, gonadoliberin II, gonadotropin-releasing hormone II, LH-RH II, luliberin II, luteinizing hormone-releasing hormone II |
| growth arrest specific protein 6 {Sp: Human} | Gas6, AXL receptor tyrosine kinase ligand |
| growth/differentiation factor-1 {Sp: Human} | GDF1, embryonic growth/differentiation factor 1, GDF-1 |
| growth/differentiation factor-10 {Sp: Human} | GDF10, BIP, BMP-3B, bone-inducing protein, bone morphogenetic protein 3B, GDF-10, growth/differentiation factor 10 |
| growth/differentiation factor-9 {Sp: Human} | GDF9, GDF-9, growth differentiation factor 9 |
| growth/diffferentiation factor-3 {Sp: Human} | GDF3, GDF-3, growth differentiation factor 3 |
| growth hormone 1 {Sp: Human} | GH1, GHN, hGH-N, pituitary growth hormone, somatotropin |
| growth hormone 2 {Sp: Human} | GH2, GHL, GH-V, hGH-V, placenta-specific growth hormone |
| GRP-(18-27) {Sp: Human, Pig} | GRP (18-27), GRP-18-27, GRP(18-27), Neuromedin C |
| GRP-(18-27) {Sp: Mouse, Rat} | GRP (18-27), GRP(18-27), neuromedin C |
| guanylin {Sp: Human} | guanylate cyclase activator 2A |
| H | |
| β-haemoglobin {Sp: Human} | beta-globin, hemoglobin beta chain, hemoglobin subunit beta |
| HB-EGF {Sp: Human} | diptheria toxin receptor, DT-R, HBEGF, heparin-binding EGF-like growth factor |
| hCG {Sp: Human} | CG, human chorionic gonadotropin |
| hemokinin 1 {Sp: Mouse} | HEK-1, HK-1 |
| hepatocyte growth factor {Sp: Human} | HGF, hepapoietin A, scatter factor, SF |
| hepatocyte growth factor alpha chain {Sp: Human} | HGF alpha chain |
| hepatocyte growth factor beta chain {Sp: Human} | HGF beta chain |
| hepcidin-20 {Sp: Human} | Hepc20 |
| hepcidin-25 {Sp: Human} | Hepc25 |
| H1 relaxin {Sp: Human} | human gene 1 relaxin |
| H2 relaxin {Sp: Human} | human gene 2 relaxin |
| H3 relaxin {Sp: Human} | human gene 3 relaxin |
| H1 relaxin (A chain) {Sp: Human} | |
| H2 relaxin (A chain) {Sp: Human} | |
| H3 relaxin (A chain) {Sp: Human} | |
| H1 relaxin (B chain) {Sp: Human} | |
| H2 relaxin (B chain) {Sp: Human} | |
| H3 relaxin (B chain) {Sp: Human} | insulin-like peptide INSL7 |
| hsp60 {Sp: Human} | 60 kDa chaperonin, 60 kDa heat shock protein, mitochondrial, chaperonin 60, CPN60, heat shock protein 60, HSP-60, HuCHA60, mitochondrial matrix protein P1, P60 lymphocyte protein |
| hsp90 {Sp: Human} | heat shock 84 kDa, heat shock protein HSP 90-beta, HSP84, HSP 84 |
| humanin {Sp: Human} | formyl humanin |
| huntingtin {Sp: Human} | huntingtin protein |
| [Hyp3]bradykinin {Sp: Human} | [Hyp$^3$]-BK, [Hydroxyproline$^3$]-bradykinin, [Hyp$^3$]-bradykinin |
| I | |
| ICAM-1 {Sp: Human} | CD_antigen = CD54, intercellular adhesion molecule 1, major group rhinovirus receptor |
| ICAM-2 {Sp: Human} | CD_antigen = CD102, intercellular adhesion molecule 2 |
| IFN-α10 {Sp: Human} | IFN alpha-10, interferon alpha-10, interferon alpha-6L, interferon alpha-C |
| IFN-α1/13 {Sp: Human} | IFN-α1, IFN-alpha 1/13, IFN-α13, interferon alpha-1/13, interferon alpha-D |
| IFN-α14 {Sp: Human} | IFN alpha-14, interferon alpha-14, interferon alpha-H, interferon lambda-2-H |
| IFN-α16 {Sp: Human} | IFN alpha-16, interferon alpha-16, interferon alpha-WA |
| IFN-α17 {Sp: Human} | IFN alpha-17, interferon alpha-17, interferon alpha-88, interferon alpha-I', interferon alpha-T |
| IFN-α2 {Sp: Human} | IFN-alpha-2, interferon alpha-2 |

TABLE 1-continued

| | Exemplary Peptidic Ligands*<br>Name |
|---|---|
| IFN-α21 {Sp: Human} | IFN-alpha 21, interferon alpha-21, interferon alpha-F |
| IFN-α4 {Sp: Human} | IFN-alpha-4, interferon alpha-4, interferon alpha-4B, interferon alpha-76, interferon alpha-M1 |
| IFN-α5 {Sp: Human} | IFN-alpha-5, interferon alpha-5, interferon alpha-61, interferon alpha-G |
| IFN-α6 {Sp: Human} | IFN-alpha-6, interferon alpha-54, interferon alpha-6, interferon alpha-K |
| IFN-α7 {Sp: Human} | IFN-alpha-7, interferon alpha-7, interferon alpha-J, interferon alpha-J1 |
| IFN-α8 {Sp: Human} | IFN-alpha-8, interferon alpha-8, interferon alpha-B, interferon alpha-B2 |
| IFN-β {Sp: Human} | fibroblast interferon, interferon beta |
| IFN-γ {Sp: Human} | immune interferon, interferon gamma |
| IFN-κ {Sp: Human} | interferon kappa |
| IFN-λ1 {Sp: Human} | cytokine Zcyto21, IFN-lambda-1, IL-29, interferon lambda-1, interferon-λ1, interleukin-29 |
| IFN-λ2 {Sp: Human} | cytokine Zcyto20, IFN-lambda-2, interferon lambda-2, interferon-λ2, interleukin-28A |
| IFN-λ3 {Sp: Human} | cytokine Zcyto22, IFN-lambda-3, IFN-lambda-4, IL-28C, interferon lambda-3, interferon-λ3, interferon-lambda-4, interleukin-28B, interleukin-28C |
| IFN-ω {Sp: Human} | interferon alpha-II-1, interferon omega-1 |
| IGF1 {Sp: Human} | insulin-like growth factor I, mechano growth factor, MGF, somatomedin-C |
| IGF2 {Sp: Human} | insulin-like growth factor II, somatomedin-A |
| IL-10 {Sp: Human} | CSIF, cytokine synthesis inhibitory factor, interleukin-10 |
| IL-11 {Sp: Human} | adipogenesis inhibitory factor, AGIF, interleukin-11, oprelvekin |
| IL-12 {Sp: Human} | |
| IL-13 {Sp: Human} | hematopoietic growth factor, interleukin-13, mast cell growth factor, multipotential colony-stimulating factor, P-cell-stimulating factor |
| IL-15 {Sp: Human} | interleukin-15 |
| IL-18 {Sp: Human} | ibocatdekin, Il-1 gamma, interferon gamma-inducing factor, interferon-γ-inducing factor, interleukin-18, interleukin-1 gamma |
| IL-19 {Sp: Human} | interleukin-19, melanoma differentiation-associated protein-like protein, NG. 1 |
| IL-1α {Sp: Human} | hematopoietin-1, interleukin-1 alpha |
| IL-1β {Sp: Human} | catabolin, interleukin-1 beta |
| IL-2 {Sp: Human} | aldesleukin, interleukin-2, T cell growth factor, TCGF |
| IL-20 {Sp: Human} | cytokine Zcyto10, interleukin-20 |
| IL-21 {Sp: Human} | interleukin-21, ZA11 |
| IL-22 {Sp: Human} | cytokine Zcyto18, IL-10-related T-cell-derived-inducible factor, interleukin-22 |
| IL-23 {Sp: Human} | |
| IL-24 {Sp: Human} | interleukin-24, MDA-7, melanoma differentiation-associated gene 7 protein, suppression of tumorigenicity 16 protein |
| IL-25 {Sp: Human} | IL-17E, interleukin-17E, interleukin-25 |
| IL-27 {Sp: Human} | |
| IL-3 {Sp: Human} | hematopoietic growth factor, interleukin-3, mast cell growth factor, MCGF, MGC79398, MGC79399, MULTI-CSF, multilineage-colony-stimulating factor, multipotential colony-stimulating factor, P-cell stimulating factor |
| IL-31 {Sp: Human} | interleukin-31 |
| IL-33 {Sp: Human} | IL-1F11, interleukin-1 family member 11, interleukin-33, NF-HEV, Nuclear factor from high endothelial venules |
| IL-36α {Sp: Human} | FIL1 epsilon, IL-1 epsilon, IL-1F6, interleukin-1 epsilon, interleukin-1 family member 6, interleukin-36 alpha |
| IL-36β {Sp: Human} | FIL1 eta, IL-1 eta, IL-1F8, IL-1H2, interleukin-1 eta, interleukin-1 family member 8, interleukin-1 homolog 2 |
| IL-36γ {Sp: Human} | IL-1 epsilon, IL-1F9, IL-1H1, IL-1-related protein 2, IL-1RP2, interleukin-1 epsilon, interleukin-1 family member 9, interleukin-1 homolog 1, interleukin-36 gamma |
| IL-37 {Sp: Human} | FIL1 zeta, IL-1F7, IL-1H, IL-1H4, IL-1RP1, IL-1X, IL-1 zeta, interleukin-1 family member 7, interleukin-1 homolog 4, interleukin-1-related protein, interleukin-1 zeta, interleukin-23 |
| IL-4 {Sp: Human} | B-cell stimulatory factor 1, binetrakin, interleukin-4, lymphocyte stimulatory factor 1, pitrakinra |
| IL-5 {Sp: Human} | B cell differentiation factor I, EDF, eosinophil differentiation factor, interleukin-5, T-cell replacing factor, TRF |
| IL-6 {Sp: Human} | B-cell stimulatory factor 2, CTL differentiation factor, hybridoma growth factor, interferon ?-2, interleukin-6 |
| IL-7 {Sp: Human} | interleukin-7 |
| IL-9 {Sp: Human} | HP40, interleukin-9, P40 |
| IL-12A {Sp: Human} | CLMF, cytotoxic lymphocyte maturation factor 1, IL12A, IL35 subunit, interleukin 12, interleukin-12A, interleukin-12 alpha chain, interleukin-12 subunit alpha, natural killer cell stimulatory factor 1, 35 kD subunit, NF cell stimulatory factor chain 1, NFSK, NKSF1, p35, subunit p35 |
| IL-17A {Sp: Human} | CTLA8, CTLA-8, cytotoxic T-lymphocyte-associated antigen 8, cytotoxic T-lymphocyte-associated serine esterase 8, interleukin-17 alpha |
| IL-23A {Sp: Human} | IL23A, IL-23p19, interleukin-23A, interleukin-23 subunit alpha |
| IL-17A/IL-17F {Sp: Human} | |

TABLE 1-continued

| | Exemplary Peptidic Ligands* Name |
|---|---|
| IL-12B {Sp: Human} | cytotoxic lymphocyte maturation factor 2, IL12B, IL-12B monomer, interleukin-12B, interleukin-12 beta chain, interleukin-12 subunit beta, natural killer cell stimulatory factor 2, natural killer cell stimulatory factor, 40 kD subunit, NKSF, p40 |
| IL-17B {Sp: Human} | |
| IL-17C {Sp: Human} | cytokine CX2, interleukin-17C |
| IL-17F {Sp: Human} | Cytokine ML-1, Interleukin-17F |
| IL-1 receptor antagonist {Sp: Human} | ICIL-1RA, IL1 inhibitor, IL-1ra, IL-1 RN, interleukin-1 receptor antagonist protein, IRAP |
| IL-36 receptor antagonist {Sp: Human} | FIL1 delta, IL-1 delta, IL-1F5, IL-1HY1, IL1L1, IL-1ra homolog 1, IL-1-related protein 3, IL-1RP3, interleukin-1 delta, interleukin-1 family member 5, interleukin-1 HY1, interleukin-1-like protein 1, interleukin-1 receptor antagonist homolog 1, interleukin-36 receptor antagonist protein |
| IL-27 subunit α {Sp: Human} | IL27A, IL-27-A, IL27-A, IL-27 subunit alpha, interleukin-27 subunit alpha, p28 |
| IL-27 subunit β {Sp: Human} | EBV-induced gene 3 protein, Epstein-Barr virus-induced gene 3 protein, IL-27B, IL-27 subunit beta, interleukin-27 subunit beta |
| inhibin α {Sp: Human} | inhibin alpha chain |
| inhibin A {Sp: Human} | |
| inhibin βA {Sp: Human} | activin βA, activin beta-A chain, EDF, erythroid differentiation factor, erythroid differentiation protein, follicle-stimulating hormone-releasing protein, inhibin beta A chain |
| inhibin B {Sp: Human} | |
| inhibin βB {Sp: Human} | activin beta-B chain, inhibin beta B chain |
| INSL3 {Sp: Human} | insulin-like peptide 3 |
| INSL5 {Sp: Human} | insulin-like peptide 5 |
| INSL5 {Sp: Mouse} | |
| INSL3 (A chain) {Sp: Human} | insulin-like peptide 3 (A chain) |
| INSL5 (A chain) {Sp: Human} | insulin-like peptide 5 (A chain) |
| INSL5 (A chain) {Sp: Mouse} | |
| INSL3 (B chain) {Sp: Human} | insulin-like peptide 3 B chain |
| INSL5 (B chain) {Sp: Human} | insulin-like peptide 5 (B chain) |
| INSL5 (B chain) {Sp: Mouse} | |
| INSL3 B chain dimer {Sp: Human} | |
| insulin {Sp: Human} | |
| insulin A chain {Sp: Human} | |
| insulin B chain {Sp: Human} | |
| insulin-like growth factor I {Sp: Mouse} | IGF-I, somatomedin |
| K | |
| kallidin {Sp: Human} | kallidin II, KD, Lys-BK, [Lys]bradykinin, Lysyl-bradykinin |
| kisspeptin-10 {Sp: Human} | KP10, KP-10 |
| kisspeptin-13 {Sp: Human} | KP13, KP-13 |
| kisspeptin-14 {Sp: Human} | KP-14 |
| kisspeptin-54 {Sp: Human} | KP54, KP-54, metastin |
| kisspeptin-52 {Sp: Mouse} | KP-52 |
| kisspeptin-10 {Sp: Mouse, Rat} | KP-10 |
| kisspeptin-52 {Sp: Rat} | KP-52 |
| kremen 1 {Sp: Human} | Dickkopf receptor, Kremen protein 1, Kringle-containing protein marking the eye and the nose, Kringle domain-containing transmembrane protein 1 |
| kremen 2 {Sp: Human} | Dickkopf receptor 2, Kremen protein 2, Kringle-containing protein marking the eye and the nose, Kringle domain-containing transmembrane protein 2 |
| L | |
| large neuromedin N {Sp: Human} | Large NN, NmN-125 |
| large neuromedin N {Sp: Mouse} | NmN-125 |
| large neuromedin N {Sp: Rat} | NmN-125 |
| large neurotensin {Sp: Human} | large NT |
| leptin {Sp: Human} | OB, OBS |
| [Leu]enkephalin {Sp: Human, Mouse, Rat} | 2-[[2-[[2-[[2-[[2-amino-3-(4-hydroxphenyl)propanoyl]amino]acetyl]amino]acetyl]amino]-3-phenyl-propanoyl]amino]-4-methyl-pentanoic acid, leucine enkephalin, [Leu]-enkephalin |
| LH {Sp: Human} | human luteinising hormone, human luteinizing hormone |
| LH {Sp: Mouse} | luteinising hormone, luteinizing hormone |
| LH {Sp: Rat} | luteinising hormone, luteinizing hormone |
| LH β, subunit {Sp: Human} | LHB, LH-B, LHβ, LH beta subunit, LSH-B, LSH-beta, luteinising hormone subunit beta, luteinizing hormone subunit beta, lutropin subunit beta |
| LH β, subunit {Sp: Mouse} | LHB, LH-B, LHβ, LH beta subunit, LSH-B, LSH-beta, luteinising hormone subunit beta, luteinizing hormone subunit beta, lutropin beta chain, lutropin subunit beta |

TABLE 1-continued

| | Exemplary Peptidic Ligands*<br>Name |
|---|---|
| LH β subunit {Sp: Rat} | LH-B, LH beta subunit, LSH-B, LSH-beta, luteinising hormone subunit beta, luteinizing hormone subunit beta, lutropin beta chain, lutropin subunit beta |
| LIF {Sp: Human} | CDF, cholinergic differentiation factor, DIA, differentiation-inducing factor, differentiation inhibitory activity, hepatocyte-stimulating factor III, HILDA, human interleukin in DA cells, leukemia inhibitory factor |
| LIGHT {Sp: Human} | CD258, Herpesvirus entry mediator-ligand, LTg, TNFSF14, TR2, Tumor necrosis factor ligand superfamily member 14, membrane form |
| LL-37 {Sp: Human} | antibacterial protein LL-37, cathelicidin LL 37 (human) |
| 5-LOX activating protein {Sp: Human} | FLAP, 5-lipoxygenase-activating protein, arachidonate 5-lipoxygenase-activating protein, MK-886-binding protein |
| LVV-hemorphin {Sp: Human} | |
| lymphotoxin-α {Sp: Human} | TNFSF1, LTα, TNFβ |
| lymphotoxin-β {Sp: Human} | TNFSF3, LTB, LTβ, TNFC |
| lymphotoxin β2α1 heterotrimer {Sp: Human} | |
| Lys-[Hyp3]-bradykinin {Sp: Human, Mouse, Rat} | [Hyp$^3$]-lysyl-bradykinin, Lys-[Hyp$^3$]-BK |

M

| | |
|---|---|
| macrophage stimulating protein 1 {Sp: Human} | MST1, hepatocyte growth factor-like |
| matrix metalloproteinase 1 {Sp: Human} | |
| matrix metalloproteinase 13 {Sp: Human} | |
| matrix metalloproteinase 2 {Sp: Human} | 72 kDa type IV collagenase, gelatinase A, MMP-2 |
| matrix metalloproteinase 2 {Sp: Mouse} | 72 kDa type IV collagenase, gelatinase A, MMP-2 |
| matrix metalloproteinase 2 {Sp: Rat} | 72 kDa type IV collagenase, gelatinase A, MMP-2 |
| M-CSF {Sp: Human} | colony stimulating factor 1, colony stimulating factor 1 (macrophage), CSF1, CSF-1, lanimostim, macrophage-CSF, MCSF |
| melanin-concentrating hormone {Sp: Human, Mouse, Rat} | human MCH, human melanin-concentrating hormone, MCH |
| [Met]enkephalin {Sp: Human, Mouse, Rat} | (2S)-2-[[(2S)-2-[[2-[[2-[[(2S)-2-amino-3-(4-hydroxphenyl)propanoyl]amino]acetyl]amino]acetyl]amino]-3-phenyl-propanoyl]amino]-4-methylsulfanyl-butanoic acid, [Met]-enkephalin, methionine enkephalin |
| Müllerian inhibiting substance {Sp: Human} | |
| motilin {Sp: Human} | |
| motilin-associated peptide {Sp: Human} | |
| β-MSH {Sp: Human} | β-melanocyte stimulating hormone |
| α-MSH {Sp: Human, Mouse, Rat} | α-melanocyte stimulating hormone |
| γ-MSH {Sp: Human, Mouse, Rat} | γ-melanocyte stimulating hormone, melanotropin gamma |
| β-MSH {Sp: Mouse} | β-melanocyte stimulating hormone |
| β-MSH {Sp: Rat} | β-melanocyte stimulating hormone |

N

| | |
|---|---|
| α-neodynorphin {Sp: Human} | α-neo-dynorphin, prodynorphin |
| α-neoendorphin {Sp: Human, Mouse, Rat} | |
| β-neoendorphin {Sp: Human, Mouse, Rat} | |
| netrin-G3 ligand {Sp: Human} | LRIG4 |
| neuregulin-1 {Sp: Human} | NRG-1, acetylcholine receptor-inducing activity, ARIA, breast cancer cell differentiation factor p45, glial growth factor, heregulin, Neu differentiation factor, neuregulin 1, NRG1, sensory and motor neuron-derived factor |
| neuregulin-2 {Sp: Human} | NRG-2, divergent of neurregulin-1, DON-1, Neural-and thymus-derived activator for ERBB kinases, neuregulin 2, NTAK |
| neuregulin-3 {Sp: Human} | NRG-3, neuregulin 3 |
| neuregulin-4 {Sp: Human} | NRG-4, neuregulin 4 |
| neurokinin A {Sp: Human, Mouse, Rat} | NKA, substance K |
| neurokinin B {Sp: Human, Mouse, Rat, Pig} | neurokinin β, neuromedin K, NKB |
| neuromedin B {Sp: Human, Mouse, Rat, Pig} | NMB |
| neuromedin N {Sp: Human} | |
| neuromedin N {Sp: Mouse, Rat} | 2,7,11-triamino-3-[2-amino-3-(4-hydroxyphenyl)propanoyl]-2,4-bis(2-amino-3-methyl-pentanoyl)-4-methyl-6-oxo-3-(pyrrolidine-2-carbonyl)undecanoic acid, NN |
| neuromedin S-33 {Sp: Human} | NMS-33, NMS |
| neuromedin S-36 {Sp: Mouse} | NMS-36, NMS |
| neuromedin S-36 {Sp: Rat} | NMS-36, NMS |
| neuromedin U-25 {Sp: Human} | NMU-25, human neuromedin U-25, neuromedin U, NMU |
| neuromedin U-23 {Sp: Mouse} | NMU-23, mouse neuromedin U |
| neuromedin U-23 {Sp: Rat} | NMU-23, rat neuromedin U, rat neuromedin U-23 |
| neuronostatin {Sp: Human, Pig} | neuronostatin-13 |
| neuropeptide γ {Sp: Human, Mouse, Rat} | |
| neuropeptide AF {Sp: Human} | NPAF, FMRFAL |
| neuropeptide AF {Sp: Mouse} | NPAF |
| neuropeptide AF {Sp: Rat} | NPAF |
| neuropeptide B-23 {Sp: Human} | NPB-23 |
| neuropeptide B-29 {Sp: Human} | NPB-29 |
| neuropeptide B-23 {Sp: Mouse} | NPB-23 |

TABLE 1-continued

| Exemplary Peptidic Ligands* | Name |
|---|---|
| neuropeptide B-29 {Sp: Mouse} | NPB-29 |
| neuropeptide B-23 {Sp: Rat} | NPB-23 |
| neuropeptide B-29 {Sp: Rat} | NPB-29 |
| neuropeptide EI {Sp: Human} | NEI, neuropeptide E-I, neuropeptide-glutamic acid-isoleucine |
| neuropeptide FF {Sp: Human, Mouse, Rat} | NPFF |
| neuropeptide GE {Sp: Human} | neuropeptide G-E, neuropeptide-glycine-glutamic acid, NGE |
| neuropeptide K {Sp: Human, Rat} | NP-K |
| neuropeptide S {Sp: Human} | NPS, human neuropeptide S |
| neuropeptide S {Sp: Mouse} | NPS, mouse neuropeptide S |
| neuropeptide S {Sp: Rat} | NPS, rat neuropeptide S |
| neuropeptide SF {Sp: Human} | NPSF |
| neuropeptide W-23 {Sp: Human} | NPW-23 |
| neuropeptide W-30 {Sp: Human} | NPW-30 |
| neuropeptide W-30 {Sp: Mouse} | NPW-30 |
| neuropeptide W-23 {Sp: Mouse, Rat} | NPW-23 |
| neuropeptide W-30 {Sp: Rat} | NPW-30 |
| neuropeptide Y {Sp: Human, Mouse, Rat} | NPY, human neuropeptide Y, mouse neuropeptide Y, rat neuropeptide Y |
| neuropeptide Y-(3-36) {Sp: Human, Mouse, Rat} | NPY 3-36, NPY-(3-36) |
| neurotensin {Sp: Human, Mouse, Rat} | NT |
| neurotrophin-3 {Sp: Human} | NT-3, HDNF, nerve growth factor 2, neurotrophic factor, NGF-2, NT3 |
| neurotrophin-4 {Sp: Human} | NT-4, neurotrophin-5, NT-5 |
| neurturin {Sp: Human} | NRTN |
| NGF {Sp: Human} | beta-nerve growth factor, beta-NGF, nerve growth factor |
| nociceptin/orphanin FQ {Sp: Human, Mouse, Rat} | N/OFQ, nociceptin, orphanin FQ |
| norrin {Sp: Human} | Norrie disease protein, X-linked exudative vitreoretinopathy 2 protein |
| norrin {Sp: Mouse} | |
| O | |
| obestatin {Sp: Human} | |
| oncostatin M {Sp: Human} | OSM |
| orexin-A {Sp: Human, Mouse, Rat} | hypocretin-1 |
| orexin-B {Sp: Human} | hypocretin-2, orexin b |
| orexin-B {Sp: Mouse, Rat} | hypocretin-2 |
| osteocrin {Sp: Human} | musclin |
| osteopontin {Sp: Human} | bone sialoprotein 1, nephropontin, secreted phosphoprotein 1, SPP-1, urinary stone protein, uropontin |
| OX-40 ligand {Sp: Human} | CD252, glycoprotein Gp34, TAX transcriptionally-activated glycoprotein 1, TNFSF4, TXGP-1 |
| oxytocin {Sp: Human, Mouse, Rat} | OT, pitocin, syntocinon |
| P | |
| PACAP-27 {Sp: Human, Mouse, Rat} | pituitary adenylate cyclase activating polypeptide-27 |
| PACAP-38 {Sp: Human, Mouse, Rat} | pituitary adenylate cyclase activating polypeptide-38 |
| PAMP-20 {Sp: Human} | Human PAMP(1-20), Proadrenomedullin N-terminal 20 peptide (human) |
| pancreatic polypeptide {Sp: Human} | PP |
| pancreatic polypeptide {Sp: Mouse} | PP |
| pancreatic polypeptide {Sp: Rat} | PP |
| PDGFA {Sp: Human} | PDGF1, PDGF-1, PDGF subunit A, platelet-derived growth factor A chain, platelet-derived growth factor alpha polypeptide, platelet-derived growth factor subunit A |
| PDGF AA {Sp: Human} | platelet-derived growth factor AA homodimer |
| PDGF AB {Sp: Human} | platelet-derived growth factor AB heterodimer |
| PDGFB {Sp: Human} | PDGF-2, PDGF subunit B, platelet-derived growth factor B chain, platelet-derived growth factor beta polypeptide, platelet-derived growth factor subunit B, proto-oncogene c-Sis, SIS, SSV |
| PDGF BB {Sp: Human} | becaplermin, platelet-derived growth factor BB homodimer |
| peptide YY {Sp: Human} | PYY, peptide tyrosine tyrosine |
| peptide YY {Sp: Mouse, Rat, Pig} | PYY, peptide tyrosine tyrosine, porcine peptide tyrosine tyrosine, porcine peptide YY |
| persephin {Sp: Human} | PSPN |
| PHI {Sp: Mouse, Rat} | intestinal peptide PHI-27, peptide histidine isoleucine, PHI-27 |
| PHM {Sp: Human} | peptide histidine-methionine |
| PHV {Sp: Human} | intestinal peptide PHV-42, peptide histidine valine |
| PHV {Sp: Rat} | intestinal peptide PHV-42, peptide histidine-valine |
| pleiotrophin {Sp: Human} | HBGF8, HBNF, heparin binding growth factor 8, NEGF1, neurite growth-promoting factor 1 |
| p122-RhoGAP {Sp: Rat} | deleted in liver cancer 1 protein homolog, rho GTPase-activating protein 7 |
| proinsulin C-peptide {Sp: Human} | |
| prokineticin-1 {Sp: Human} | EG-VEGF, endocrine gland-derived vascular endothelial growth factor, mambakine, PROK1, prokineticin 1 |
| prokineticin-2 {Sp: Human} | PROK2, protein Bv8 homologue |
| prokineticin-2β {Sp: Human} | PK2β |

TABLE 1-continued

| | Exemplary Peptidic Ligands* |
|---|---|
| | Name |
| prokineticin-1 {Sp: Mouse} | endocrine gland vascular endothelial growth factor, PROK1, prokineticin 1 |
| prokineticin-2 {Sp: Mouse, Rat} | prokineticin 2 |
| prokineticin-1 {Sp: Rat} | endocrine gland vascular endothelial growth factor, PROK1 |
| prolactin {Sp: Human} | |
| prosaptide {Sp: Human} | |
| protein C {Sp: Human} | activated protein C, anticoagulant protein C, autoprothrombin IIA, inactivator of coagulation factors Va and VIIIa, vitamin K-dependent protein C |
| protein C {Sp: Mouse} | |
| protein C {Sp: Rat} | |
| protein C heavy chain {Sp: Human} | |
| protein C heavy chain {Sp: Mouse} | |
| protein C heavy chain {Sp: Rat} | |
| protein C light chain {Sp: Human} | |
| protein C light chain {Sp: Mouse} | |
| protein C light chain {Sp: Rat} | |
| protein S {Sp: Human} | protein Sα, vitamin K-dependent protein S |
| PrRP-20 {Sp: Human} | human prolactin-releasing peptide-20, PRH, PrRP20 |
| PrRP-31 {Sp: Human} | human prolactin-releasing peptide-31, PRH, PrP31, PrRP31 |
| PrRP-20 {Sp: Rat} | rat prolactin-releasing peptide-20 |
| PrRP-31 {Sp: Rat} | rat prolactin-releasing peptide-31 |
| PTH {Sp: Human} | human parathyroid hormone |
| PTH {Sp: Mouse} | mouse parathyroid hormone |
| PTH {Sp: Rat} | rat parathyroid hormone |
| PTHrP {Sp: Human} | parathyroid hormone-like hormone, parathyroid hormone-related peptide |
| PTHrP-(1-36) {Sp: Human} | human parathyroid hormone related peptide, parathyroid hormone-like protein, PTHrP (1-36), PTHrP-1-36 |
| [Pyr1]apelin-13 {Sp: Human, Mouse, Rat} | Glu$^1$-apelin-13 |
| PYY-(3-36) {Sp: Human} | human peptide tyrosine tyrosine (3-36), human peptide YY (3-36), PYY (3-36), PYY$_{3-36}$ |
| PYY-(3-36) {Sp: Mouse, Rat} | peptide tyrosine tyrosine (3-36), peptide YY (3-36), PYY (3-36), PYY$_{3-36}$ |
| Q | |
| QRFP {Sp: Human} | 26RFa, pyroglutamylated arginine-phenylalanine-amide peptide, QRFP-43 |
| QRFP26 {Sp: Human} | P518 |
| QRFP {Sp: Mouse} | pyroglutamylated arginine-phenylalanine-amide peptide, QRFP-43 |
| QRFP26 {Sp: Mouse} | mouse homologue of P518, P550 |
| QRFP {Sp: Rat} | pyroglutamylated arginine-phenylalanine-amide peptide, QRFP-43 |
| R | |
| Rac1 {Sp: Human} | cell migration-inducing gene 5 protein, p21-Rac1, ras-like protein TC25, ras-related C3 botulinum toxin substrate 1 |
| Rac2 {Sp: Human} | GX, p21-Rac2, ras-related C3 botulinum toxin substrate 2, small G protein |
| Rac3 {Sp: Human} | p21-Rac3, ras-related C3 botulinum toxin substrate 3 |
| RANK ligand {Sp: Human} | CD254 antigen, ODF, OPGL, osteoclast differentiation factor, osteoprotegerin ligand, RANKL, Receptor activator of nuclear factor κB ligand, TNF-related activation-induced cytokine, TNFSF11, TRANCE, Tumor necrosis factor ligand superfamily member 11, membrane form |
| relaxin {Sp: Rat} | |
| relaxin A chain {Sp: Rat} | |
| relaxin B chain {Sp: Rat} | |
| retinoblastoma-associated protein {Sp: Human} | Rb, pRb, retinoblastoma cell cycle regulation protein |
| RFRP-1 {Sp: Human} | neuropeptide RFRP-1 |
| RFRP-2 {Sp: Human} | neuropeptide RFRP-2 |
| RFRP-3 {Sp: Human} | neuropeptide RFRP-3, NPVF |
| RGS2 {Sp: Human} | cell growth-inhibiting gene 31 protein, G0/G1 switch regulatory protein 8, regulator of G-protein signalling 2 |
| Rho GDP dissociation inhibitor beta {Sp: Human} | D4-GDI, GDP dissociation inhibitor, Ly-GDI, Rho-GDI 2, Rho-GDI beta, Rho GDP-dissociation inhibitor 2 |
| ribosomal protein S19 {Sp: Human} | RP-S19, DBA, Diamond-Blackfan anemia, RPS19, S19 ribosomal protein |
| R-spondin-1 {Sp: Human} | hRspo1, Roof plate-specific spondin-1, R-spondin 1 |
| R-spondin-2 {Sp: Human} | hRspo2, Roof plate-specific spondin-2, R-spondin 2 |
| R-spondin-3 {Sp: Human} | hPWTSR, hRspo3, protein with TSP type-1 repeat, Roof plate-specific spondin-3, R-spondin 3, thrombospondin type-1 domain-containing protein 2 |
| R-spondin-4 {Sp: Human} | hRspo4, Roof plate-specific spondin-4, R-spondin 4 |
| R-spondin-1 {Sp: Mouse} | cristin-3, cysteine-rich and single thrombospondin domain-containing protein 3, mCristin-3, roof plate-specific spondin-1 |
| R-spondin-2 {Sp: Mouse} | cristin-2, cysteine-rich and single thrombospondin domain-containing protein 2, mCristin-2, roof plate-specific spondin-2 |

TABLE 1-continued

| | Exemplary Peptidic Ligands*<br>Name |
|---|---|
| R-spondin-3 {Sp: Mouse} | cabriolet, cristin-1, cysteine-rich and single thrombospondin domain-containing protein 1, nucleopondin, roof plate-specific spondin-3 |
| R-spondin-4 {Sp: Mouse} | cristin-4, cysteine-rich and single thrombospondin domain-containing protein 4, mCristin-4, roof plate-specific spondin-4 |
| S | |
| sclerostin {Sp: Human} | SOST |
| SDF-1α {Sp: Human} | CXCL12 α, stromal cell-derived factor-1α |
| SDF-1β {Sp: Human} | CXCL12 β, SDF-1, stromal cell-derived factor-1, stromal cell-derived factor-1β |
| secretin {Sp: Human} | |
| secretin {Sp: Mouse} | |
| secretin {Sp: Rat} | |
| serum amyloid A {Sp: Human} | rhSAA, SAA |
| sFRP-1 {Sp: Human} | FRP-1, SARP-2, secreted apoptosis-related protein 2, Secreted Frizzled-Related Protein 1 |
| sFRP-2 {Sp: Human} | FRP-2, SARP-1, secreted apoptosis-related protein 1, Secreted Frizzled-Related Protein 2 |
| sFRP-3 {Sp: Human} | Frezzled, Fritz, Frizzled-related protein 1, FrzB-1, Secreted Frizzled-Related Protein 3 |
| sFRP-4 {Sp: Human} | frizzled protein, human endometrium, FrpHE, Secreted Frizzled-Related Protein 4 |
| sFRP-5 {Sp: Human} | Frizzled-related protein 1b, FRP-1b, SARP-3, Secreted apoptosis-related protein 3, Secreted Frizzled-Related Protein 5 |
| SRIF-14 {Sp: Human, Mouse, Rat} | somatostatin-14, SS14, SST-14 |
| SRIF-28 {Sp: Human, Mouse, Rat} | somatostatin 1-28, somatostatin-28, SST-28 |
| stem cell factor {Sp: Human} | SCF, c-Kit ligand, KITLG, mast cell growth factor, MGF, stern cell factor |
| substance P {Sp: Human, Mouse, Rat} | SP |
| T | |
| TGFα {Sp: Human} | EGF-like TGF, ETGF, TGF type 1, transforming growth factor-α |
| TGFβ1 {Sp: Human} | TGF-beta-1, transforming growth factor beta-1 |
| TGFβ2 {Sp: Human} | BSC-1 cell growth inhibitor, cetermin, glioblastoma-derived T-cell suppressor factor, G-TSF, polyergin, TGF-beta-2, transforming growth factor beta-2 |
| TGFβ3 {Sp: Human} | TGF-beta-3, transforming growth factor beta-3 |
| thrombin {Sp: Human} | |
| thrombin {Sp: Mouse} | |
| thrombin {Sp: Rat} | |
| thrombin heavy chain {Sp: Human} | thrombin B chain |
| thrombin heavy chain {Sp: Mouse} | thrombin B chain (mouse) |
| thrombin heavy chain {Sp: Rat} | thrombin B chain (rat) |
| thrombin light chain {Sp: Human} | thrombin A chain |
| thrombin light chain {Sp: Mouse} | thrombin A chain (mouse) |
| thrombin light chain {Sp: Rat} | thrombin A chain (rat) |
| thrombopoietin {Sp: Human} | C-mpl ligand, megakaryocyte colony-stimulating factor, megakaryocyte growth and development factor, MGDF, myeloproliferative leukemia virus oncogene ligand, TPO |
| thymic stromal lymphopoietin {Sp: Human} | TSLP |
| TIMP1 {Sp: Human} | collagenase inhibitor, EPA, erythroid-potentiating activity, fibroblast collagenase inhibitor, metalloproteinase inhibitor 1, tissue inhibitor of metalloproteinases 1 |
| TIMP2 {Sp: Human} | CSC-21K, TIMP-2, tissue inhibitor of metalloproteinases 2 |
| TIMP3 {Sp: Human} | metalloproteinase inhibitor 3 precursor, MIG-5, tissue inhibitor of metalloproteinases 3 |
| TIMP4 {Sp: Human} | metalloproteinase inhibitor 4, TIMP-4, tissue inhibitor of metalloproteinases 4 |
| TIP39 {Sp: Human, Bovine} | human/bovine tuberoinfundibular peptide |
| TIP39 {Sp: Mouse, Rat} | tuberoinfundibular peptide |
| T-kinin {Sp: Human, Rat} | Ile-Ser-BK, [Ile,Ser]bradykinin |
| TL6 {Sp: Human} | activation-inducible TNF-related ligand, glucocorticoid-induced TNF-related ligand, TNFSF18 |
| TL1A {Sp: Human} | TL1, TNF ligand-related molecule 1, TNFSF15, Tumor necrosis factor ligand superfamily member 15, membrane form, vascular endothelial cell growth inhibitor, VEGI |
| TRAIL {Sp: Human} | Apo-2 ligand (Apo-2L), CD253, TL2, TNFSF10 |
| TRH {Sp: Human, Mouse, Rat} | thyroliberin, thyrotropin-releasing hormone |
| TSH {Sp: Human} | thyroid-stimulating hormone, thyrotropin |
| TSH {Sp: Mouse} | thyroid-stimulating hormone, thyrotropin |
| TSH {Sp: Rat} | thyroid-stimulating hormone, thyrotropin |
| TSH β subunit {Sp: Human} | thyroid stimulating hormone beta, thyroid-stimulating hormone subunit beta, thyrotropin beta chain, thyrotropin subunit beta, TSHB, TSH-B, TSH-beta, TSH beta subunit |
| TSH β subunit {Sp: Mouse} | thyroid-stimulating hormone subunit beta, thyrotropin beta chain, thyrotropin subunit beta, TSHB, TSH-B, TSH-beta, TSH beta subunit |
| TSH β subunit {Sp: Rat} | thyroid-stimulating hormone subunit beta, thyrotropin beta chain, thyrotropin subunit beta, TSHB, TSH-B, TSH-beta, TSH beta subunit |

TABLE 1-continued

| | Exemplary Peptidic Ligands* Name |
|---|---|
| tumour necrosis factor membrane form {Sp: Human} | TNF membrane form, cachectin, cytotoxin, DIF, necrosin, TNF, TNFα, TNFSF2, tumour necrosis factor |
| tumour necrosis factor shed form {Sp: Human} | TNF shed form, cachectin, cytotoxin, DIF, necrosin, TNF, TNFα, TNF alpha soluble form, TNFSF2 shed form, tumor necrosis facot soluble form, tumour necrosis factor |
| TWEAK {Sp: Human} | Apo3L, Apo-3 ligand, CD255, TNF-related weak inducer of apoptosis, TNFSF12, Tumor necrosis factor ligand superfamily member 12, membrane form |
| U | |
| urocortin 1 {Sp: Human} | UCN |
| urocortin 2 {Sp: Human} | urocortin II |
| urocortin 3 {Sp: Human} | |
| urocortin 2 {Sp: Mouse} | |
| urocortin 1 {Sp: Mouse, Rat} | |
| urocortin 3 {Sp: Mouse, Rat} | |
| urocortin 2 {Sp: Rat} | |
| uroguanylin {Sp: Human} | |
| urotensin-II {Sp: Human} | U-II |
| urotensin-II {Sp: Mouse} | U-II |
| urotensin-II {Sp: Rat} | U-II |
| urotensin-related peptide {Sp: Human, Mouse, Rat} | URP, urotensin-II-related peptide |
| V | |
| vasopressin {Sp: Human, Mouse, Rat} | AVP, ADH, antidiuretic hormone, arginine vasopressin, argipressin |
| VCAM-1 {Sp: Human} | CD_antigen = CD106, INCAM-100, vascular cell adhesion protein 1, V-CAM 1 |
| VEGFA {Sp: Human} | vascular endothelial growth factor A, vascular permeability factor, VEGF-A, VPF |
| VEGFB {Sp: Human} | vascular nedothelial growth factor B, VEGF-B, VEGF-related factor, VRF |
| VEGFC {Sp: Human} | Flt4-L, Flt4 ligand, vascular endothelial growth factor C, vascular endothelial growth factor-related protein, VEGF-C, VRP |
| VEGFD {Sp: Human} | c-fos induced growth factor, FIGF |
| VEGFE {Sp: Human} | fallotein, PDGFC, PDGF-C, platelet-derived growth factor C, SCDGF, spinal cord-derived growth factor, VEGF-E |
| VIP {Sp: Human, Mouse, Rat} | vasoactive intestinal peptide, vasoactive intestinal polypeptide |
| vitronectin {Sp: Human} | serum-spreading factor, S-protein, V75, VN |
| vitronectin V10 subunit {Sp: Human} | |
| vitronectin V65 subunit {Sp: Human} | |
| von Willebrand factor {Sp: Human} | vWF |
| W | |
| Wnt-1 {Sp: Human} | proto-oncogene protein Wnt-1, WNT1 |
| Wnt-11 {Sp: Human} | protein Wnt-11, WNT11 |
| Wnt-16 {Sp: Human} | protein Wnt-16, WNT16 |
| Wnt-2 {Sp: Human} | Int-1-like protein 1, Int-1-related protein, protein Wnt-2, WNT2 |
| Wnt-3 {Sp: Human} | proto-oncogene Int-4 homolog, proto-oncogene Wnt-3, WNT3 |
| Wnt-4 {Sp: Human} | protein Wnt-4, WNT4 |
| Wnt-6 {Sp: Human} | protein Wnt-6, WNT6 |
| Wnt-10a {Sp: Human} | protein Wnt-10a, WNT10A |
| Wnt-3a {Sp: Human} | protein Wnt-3a, WNT3A |
| Wnt-5a {Sp: Human} | protein Wnt-5a, WNT5A |
| Wnt-7a {Sp: Human} | protein Wnt-7a, WNT7A |
| Wnt-8a {Sp: Human} | protein Wnt-8a, protein Wnt-8d, WNT8A |
| Wnt-9a {Sp: Human} | protein Wnt-14, protein Wnt-9a, WNT-14, WNT9A |
| Wnt-10b {Sp: Human} | protein Wnt-10b, protein Wnt-12, WNT10B, WNT-12 |
| Wnt-2b {Sp: Human} | protein Wnt-13, protein Wnt-2b, WNT-13, WNT2B |
| Wnt-5b {Sp: Human} | protein Wnt-5b, WNT5B |
| Wnt-7b {Sp: Human} | protein Wnt-7b, WNT7B |
| Wnt-8b {Sp: Human} | protein Wnt-8b, WNT8B |
| Wnt-9b {Sp: Human} | WNT-14b, WNT-15, WNT9B |
| Wnt-inhibitory factor {Sp: Human} | WIF-1, wnt inhibitory factor 1 |
| X | |
| XCL1 {Sp: Human} | ATAC, c motif cytokine 1, cytokine SCM-1α, LPTN, lymphotactin α, SCM-1α |
| XCL2 {Sp: Human} | C motif cytokine 2, cytokine SCM-1β, lymphotactin β, SCM-1β |
| XCL1 {Sp: Mouse} | lymphotactin-α |
| XCL1 {Sp: Rat} | lymphotactin-α |
| xenin {Sp: Human, Mouse, Rat} | |

*= Additional peptides compatible with various embodiments may be found, inter alia, at www.phoenixpeptide.com/catalog and in Development trends for peptide therapeutics: A comprehensive quantitative analysis of peptide therapeutics in clinical development, Peptide Therapeutics Foundation, 2010.

The amino acid sequence of human chemerin is available as GenBank Accession No. NP_002880, and the corresponding nucleic acid sequence is available as GenBank Accession No. NM_002889.

```
GenBank Accession No. NP_002880
(SEQ ID NO.: 6):
MRRLLIPLAL WLGAVGVGVA ELTEAQRRGL QVALEEFHKH

PPVQWAFQET SVESAVDTPF PAGIFVRLEF KLQQTSCRKR

DWKKPECKVR PNGRKRKCLA CIKLGSEDKV LGRLVHCPIE

TQVLREAEEH QETQCLRVQR AGEDPHSFYF PGQFAFSKAL

PRS

GenBank Accession No. NM_002889
(SEQ ID NO.: 7):
GCCGCCCCGC GAGAAGAAGA GCGGGAAGAG GCGGACAGCG

AGGCCAAGAT TTCAGCTGCG GGACGGTCAG GGGAGACCTC

CAGGCGCAGG GAAGGACGGC CAGGGTGACA CGGAAGCATG

CGACGGCTGC TGATCCCTCT GGCCCTGTGG CTGGGTGCGG

TGGGCGTGGG CGTCGCCGAG CTCACGGAAG CCCAGCGCCG

GGGCCTGCAG GTGGCCCTGG AGGAATTTCA CAAGCACCCG

CCCGTGCAGT GGGCCTTCCA GGAGACCAGT GTGGAGAGCG

CCGTGGACAC GCCCTTCCCA GCTGGAATAT TTGTGAGGCT

GGAATTTAAG CTGCAGCAGA CAAGCTGCCG GAAGAGGGAC

TGGAAGAAAC CCGAGTGCAA AGTCAGGCCC AATGGGAGGA

AACGGAAATG CCTGGCCTGC ATCAAACTGG GCTCTGAGGA

CAAAGTTCTG GGCCGGTTGG TCCACTGCCC CATAGAGACC

CAAGTTCTGC GGGAGGCTGA GGAGCACCAG GAGACCCAGT

GCCTCAGGGT GCAGCGGGCT GGTGAGGACC CCCACAGCTT

CTACTTCCCT GGACAGTTCG CCTTCTCCAA GGCCCTGCCC

CGCAGCTAAG CCAGCACTGA GATGCGTGGT GCCTCCAGGA

CCGCTGCGGG TGGTAACCAG TGGAAGACCC CAGCCCCAG

GGAGAGGAAC CCGTTCTATC CCCAGCCATG ATAATAAAGC

TGCTCTCCCA GCTGCCTCTC AAAAAAAAAA AAAAAAAAA

AAAAAAA
```

The amino acid sequence of murine chemerin is available as GenBank Accession No. NP_082128, and the corresponding nucleic acid sequence is available as GenBank Accession No. NM_027852.

```
GenBank Accession No. NP_082128
(SEQ ID NO.: 15):
MKCLLISLAL WLGTVGTRGT EPELSETQRR SLQVALEEFH

KHPPVQLAFQ EIGVDRAEEV LFSAGTFVRL EFKLQQTNCP

KKDWKKPECT IKPNGRRRKC LACIKMDPKG KILGRIVHCP

ILKQGPQDPQ ELQCIKIAQA GEDPHGYFLP GQFAFSRALR

TK

GenBank Accession No. NM_027852
(SEQ ID NO.: 16):
AAGAGGAAGG TCAGGGAACT TTGGGAAACA GAAAACTCCA

AAACTCCGGA CTCTGGGAGA AGGGTCAGTG GGAAAAGGCG

GGGCTTTGGG GACCAAGAGA GAGGAGAAAA GGGAGATGAG

AGGGTGAGAG GGAACAACTG CCAGGGAGCT GTTCCAGGGA

CCACACAGAA AAAGGCCTCG CTAAAGCAAC AAACCTGATC

ATTTTCAAGA ACCATAGGAC TGAGGTGAAG CCATGAAGTG

CTTGCTGATC TCCCTAGCCC TATGGCTGGG CACAGTGGGC

ACACGTGGGA CAGAGCCCGA ACTCAGCGAG ACCCAGCGCA

GGAGCCTACA GGTGGCTCTG GAGGAGTTCC ACAAACACCC

ACCTGTGCAG TTGGCCTTCC AAGAGATCGG TGTGGACAGA

GCTGAAGAAG TGCTCTTCTC AGCTGGCACC TTTGTGAGGT

TGGAATTTAA GCTCCAGCAG ACCAACTGCC CCAAGAAGGA

CTGGAAAAAG CCGGAGTGCA CAATCAAACC AAACGGGAGA

AGGCGGAAAT GCCTGGCCTG CATTAAAATG GACCCCAAGG

GTAAAATTCT AGGCCGGATA GTCCACTGCC CAATTCTGAA

GCAAGGGCCT CAGGATCCTC AGGAGTTGCA ATGCATTAAG

ATAGCACAGG CTGGCGAAGA CCCCCACGGC TACTTCCTAC

CTGGACAGTT TGCCTTCTCC AGGGCCCTGA GAACCAAATA

AGCCCTAGAC AGGACTTCAC CTTACTCCCT GTACAGCTGT

GGCAGCACCC AGCAGGAGCA TATCGTCTCC CAGAGACTTT

CAACTCCAGG CTAATAAAAT TGCTGAGTCT GTTCCTTTCC

AA
```

Small Molecule Ligand Entities

In some embodiments, a ligand entity is or comprises a small molecule. In general, any small molecule that binds appropriately to a target of interest and is subject to lipidation as described herein may be utilized in accordance with the present invention.

In some embodiments, small molecule ligand entity may be or comprise any FDA-approved compound that acts on a membrane-associated target. In some embodiments, a ligand entity may be or comprise an alkaloid, glycoside, phenazine, phenol, polyketide, terpene, or pyrroles (e.g., tetrapyrroles). Additional exemplary small molecule ligand entities may be found, inter alia, at www.hit2lead.com/.

In some embodiments, suitable small molecule ligand entities may be or comprise antimicrobial agents. In some embodiments, antimicrobial agents are antibacterial, antifungal, antiviral, anti-inflammatory and/or pain management agents or have one or more antibacterial, antifungal, antiviral, anti-inflammatory and/or pain management properties.

Pain Management Agents

In some embodiments, a small molecule ligand entity is or comprises a pain management agent including, e.g., a nonopiod analgesic (acetaminophen, aspirin, choline magnesium trisalicylate, NSAIDs, tramadol (opioid & nonopioid)), an opioid analgesic (codeine, dihydrocodeine, hydrocodone, oxycodone, morphine, hydromorphone, fentanyl), or an analgesic adjuvant used to enhance the effect of an analgesic or counteract side effects of such (tricyclic antidepressants, benzodiazepines, caffeine, corticosteroids, anticonvulsants).

In some embodiments, a small molecule ligand entity or pharmaceutically acceptable salt thereof is or comprises an analgesic agent including, e.g., codeine, hydrocodone, hydromorphone, morphine, oxymorphone, oxycodone, meperidine, methadone, propoxyphene, tramadol, acetaminophen, pentazocine and fentanyl salicylates.

In some embodiments, a ligand entity is or comprises a small molecule selected from those listed in Table 2.

TABLE 2

Exemplary Small Molecule Ligand Entities*

| Name | |
|---|---|
| abarelix | Plenaxis, PPI 149, R 3827 |
| abatacept | BMS-188667 RG-2077, CTLA4-IgG4m, L04AA24, RG-1046 |
| abciximab | 7E3, 7E3 antibody, antiGPIIBIIIa, C7E3 |
| acarbose | BAY-G 5421, BAY-G-5421 |
| acetazolamide | , diamox, diluran, edemox, glaupax |
| acetic acid | acetate, C2, ethanoic acid |
| acetohexamide | |
| acetyldigitoxin | acetyldiginatin, alpha-acetyldigitoxin |
| ACTH {Sp: Human} | ACTH (1-39), adrenocorticotrophin, adrenocorticotropic hormone, adrenocorticotropic hormone (1-39), corticotropin |
| acyclovir | Aciclovir |
| adalimumab | HUMIRA |
| adapalene | |
| adenine | |
| adenosine | |
| (−)-adrenaline | Adrenalin, adrenaline, l-Adrenaline, L-epinephrine, Levoepinephrine |
| afatinib | BIBW 2992, gilotrif, giotrif, tomtovok, tovok |
| aflibercept | AVE0005, AVE 0005, VEGF Trap, VEGF Trap-Eye, VEGF Trap-regeneron, ziv-aflibercept |
| agomelatine | N-(2-[7-methoxy-1-naphthalenyl]ethyl)acetamide, N-[2-(7-methoxynaphthalen-1-yl)ethyl]acetamide, S20098 |
| alefacept | ASP 0485, BG 9273, BG-9273, BG 9712, BG-9712, human LFA 3IgG fusion protein, LFA 3CD2, Lfa3Tip, LFA 3TIP |
| alemtuzumab | campath 1H, campath-1H |
| alendronate | 4-amino-1-hydroxybutylidene-1,1-bisphosphonate, ABDP, BPH 1, MK-217 |
| aliskiren | CGP-060536B, SPP100 |
| allopurinol | allopurinol sodium, BW-56158, BW-56-158, lopurin, zyloprim |
| all-trans-retinoic acid | 4-(6-hydroxy-7-tricyclo[3.3.1.13,7]dec-1-yl-2-naphthalenyl)benzoic acid, all-trans retinoic acid, ATRA, tretinoin |
| alosetron | GR68755 |
| alprenolol | 1-(o-Allylphenoxy)-3-(isopropylamino)-2-propanol, 1-propan-2-ylamino-3-(2-prop-2-enylphenoxy)-propan-2-ol, Alfeprol, Alpheprol, Alprenololum |
| amantidine | |
| amiloride | |
| 6-aminocaproic acid | aminocaproic acid |
| aminohippuric acid | PAH, p-aminohippurate, p-aminohippuric acid |
| 5-aminolevulinic acid | 5-aminolevulinate, D-aminolevulinic acid |
| amiodarone | |
| amisulpride | 4-amino-N-[(1-ethylpyrrolidin-2-yl)methyl]-5-ethylsulfonyl-2-methoxybenzamide, Amitrex, (±)-amisulpride, Solian, Sulpitac, sultopride |
| amitriptyline | amitryptiline, amitryptyline, Damilen, Damitriptyline, Elavil, Flavyl, Lantron, Lentizol, Prophetadiene, Seroten, Triptanol |

TABLE 2-continued

Exemplary Small Molecule Ligand Entities*

| Name | |
|---|---|
| amoxapine | amoxepine, amoxipine |
| amphetamine | DL-amphetamine, (±)-amphetamine |
| anastrazole | arimidex |
| apixaban | BMS-562247, Eliquis |
| apomorphine | 5,6,6a,7-Tetrahydro-6-methyl-4H-dibenzo[de,g]quinolin-10,11-diol, (6aR)-6-Methyl-5,6,6a,7-tetrahydro-4H-dibenzo[de,g]quinoline-10,11-diol |
| aprepitant | 5-[[(2R,3S]-2-[(1R)-1-[3,5-bis(trifluoromethyl) phenyl]ethoxy]-3-(4-fluorphenyl)-4-morpholinyl]methyl]-1,2-dihydro-3H-1,2,4-triazol-3-one |
| aprotinin {Sp: Bovine} | basic protease inhibitor, BPI, BPTI, pancreatic trypsin inhibitor, Trasylol |
| argatroban | AC1L99H9 |
| aripiprazole | 7-(4(4-(2,3-dichlorophenyl)-1-piperazinyl(butyloxy)-3,4-dihydro-2(1H)-quinolinone, 7-[4-[4-(2,3-dichlorophenyl)piperazin-1-yl]butoxy]-3,4-dihydro-1H-quinolin-2-one, Abilify, Abilitat, OPC 14597, OPC-14597 |
| aspirin | acetylsalicylic acid |
| astemizole | |
| atenolol | 2-[4-[2-hydroxy-3-(propan-2-ylamino)-propoxy]phenyl]acetamide, Atehexal, Cuxanorm, Ibinolo, Myocord, Normiten, Prenormine, Selobloc, Tenoblock, Tenormin |
| atorvastatin | |
| atropine | [(1S,5R)-8-methyl-8-azabicyclo[3.2.1]oct-3-yl] 3-hydroxy-2-phenyl-propanoate, atropen, atropinol, eyesules, hyoscyamine |
| axitinib | AG013736, AG 013736, AG-013736, inlyta |
| azacitidine | 5-AZAC, 5-azacytidine, ladakamycin, U-18496 |
| azilsartan medoxomil | TAK 491 |

B

| | |
|---|---|
| baclofen | |
| (−)-baclofen | 4-amino-3-(4-chlorophenyl)-butanoic acid, Baclon, Kemstro, Lioresal, p-chlorophenyl GABA, (R)-(−)-baclofen |
| bambuterol | |
| basiliximab | CHI-621, L04AC02, SDZ-CHI-621 |
| belatacept | BMS-224818, LEA29Y |
| belimumab | L04AA26, lymphostat-B |
| benazepril | Lotensin |
| benazeprilat | |
| bepridil | |
| betaxolol | 1-[4-[2-(cyclopropylmethoxy)ethyl]phenoxy]-3-(propan-2-ylamino)-propan-2-ol, Betaxololum |
| bethanechol | 2-carbamoyloxpropyl-trimethyl-azanium, besacholine, mechotane, mechothane, mecothane, mictone, mictrol, myocholine, urecholine |
| bevacizumab | rhuMAb-VEGF |
| bexarotene | 4-(1-[3,5,5,8,8-pentamethyl-5,6,7,8-tetrahydro-2-naphthyl]ethenyl) benzoic acid, Bexarotene, LGD1069, Targretin |
| bezafibrate | |
| bicalutamide | |
| bimatoprost | AGN 192024, LS-181817, lumigan, (Z)-7-[(1R,2S,3R,5S)-3,5-dihydroxy-2-[(E,3S)-3-hydroxy-5-phenyl-pent-1-enyl]cyclopentyl]-N-ethyl-hept-5-enamide |
| biotin | |
| bivalirudin | Angiomax, Hirulog-1 |
| bortezomib | PS-341, Velcade |
| bosentan | RO 47-0203 |
| brentuximab vedotin | antibody-drug conjugate SGN-35, nti-CD30 ADC SGN-35, SGN 35, SGN-35 |

TABLE 2-continued

Exemplary Small Molecule Ligand Entities*

| Name | |
|---|---|
| brimonidine | 5-bromo-N-(4,5-dihydro-1H-imidazol-2-yl)quinoxalin-6-amine, UK14304, UK14,304 |
| brinzolamide | AL-4862 |
| bromocriptine | 2-Bromo-alpha-ergokryptin, 2-Bromoergocryptine, alpha-Bromoergocriptine, Bromergocryptine, Bromocriptin, bromocryptine, Bromoergocriptine, CB-154 |
| bumetanide | Edemex, Fontego, Fordiuran, Lixil, Lunetoron, PF 1593, Ro 10-6338 |
| bunolol | 3,4-Dihydro-5-(3-(tert-butylamino)-2-hydroxy)propoxy-1(2H)-naphthalenone, 5-(2-hydroxy-3-tert-butylamino-propoxy)tetralin-1-one, BRN 1887243, (−)-bunolol, Bunololo, Bunololum, l-Bunolol, Levobunolol, W-6421A |
| bupivacaine | 1-butyl-N-(2,6-dimethylphenyl)piperidine-2-carboxamide, Anekain, Bloqueina, Bupivacaina, Bupivacainum, cBupivacaine, DL-Bupivacaine, Marcaine , Sensorcaine, W-7 |
| bupranolol | 1-(2-chloro-5-methyl-phenoxy)-3-(tert-butylamino)-propan-2-ol, 3-(tert-Butylamino)-1-(6-chloro-m-tolyloxy)-2-propanol, BRN 2272923, Bupranol, Bupranololum, Ophtorenin, SK&F 16805-A |
| buprenorphine | (2S)-2-[(−)-(5R,6R,7R,14S)-9α-cyclopropylmethyl-4,5-epoxy-6,14-ethano-3-hydroxy-6-methoxmorphinan-7-yl]-3,3-dimethylbutan-2-ol |
| buserelin | etilamide, HOE 766, HOE 766A, ICI 123215, receptal, suprefact |
| buspirone | 8-[4-(4-pyrimidin-2-ylpiperazin-1-yl)butyl]-8-azaspiro[4.5]decane-7,9-dione, Ansial, Buspirona, Buspironum |

C

| | |
|---|---|
| cabazitaxel | taxoid XRP6258, TXD 258, XRP-6258 |
| cabergoline | |
| caffeine | 1,3,7-trimethylpurine-2,6-dione, Cafeina, Caffein, Cafipel, Coffeine, guaranine, Koffein, Mateina, Methyltheobromine, Thein |
| calcipotriol | 26,27-cyclo-22-ene-1α,24S-dihydroxyvitamin D3, MC903 |
| calcitonin (salmon) | CT (salmon), salmon calcitonin |
| camostat | ONO-3403 |
| canakinumab | ACZ885, ACZ 885 |
| candesartan | 2-ethoxy-1-{[2'-(1H-tetrazol-5-yl)biphenyl-4ethyl]-1H-benzimidazole-7-carboxylic acid, 2-ethoxy-1-[(2'-(1H-tetrazol-5-yl)biphenyl-4-yl)methyl]-1H-benzimidazoline-7-carboxylic acid, CV-11974 |
| capecitabine | Ro-091978000, Ro-09-1978-000 |
| capromab | 7E11-C5.3, capromab pendetide, CYT-351, CYT-356, cytogen 356, Indium In 111 capromab, oncoscint prostate, pendetide |
| capsaicin | Axsain , Capsaicin, Capsidol, Capzasin , (E)-N-[(4-hydroxy-3-methoxyphenyl)methyl]-8-methylnon-6-enamide, Qutenza, Styptysat, Transacin, Zostrix |
| captopril | SQ-14225 |
| carbachol | 2-carbamoyloxyethyl-trimethyl-azanium, carbacholin, carbacholine, carbacolina, carbamiotin, carbochol, carbocholin, carbocholine, carcholin |
| carbamazepine | calepsin |
| carbidopa | lodosyn |
| carmustine | BCNU, caxeta, xabine |
| carvedilol | 1-(9H-carbazol-4-yloxy)-3-[2-(2-methoxyphenoxy)ethylamino]-propan-2-ol, Carvedilolum, Coreg, DQ 2466, SKF 105517 |
| cefadroxil | |
| ceftriaxone | Rocephin |
| cephalexin | Cefalexin |
| cephradine | Cefradine |
| certolizumab pegol | CDP870, PHA 738144 |
| cetirizine | (±)-[2-[4-[(4-chlorophenyl)phenylmethyl]-1-piperazinyl]ethoxy]acetic acid, dihydrochloride |
| (R)-cetirizine | 2-[2-[4-[(4-chlorophenyl)-phenyl-methyl]piperazin-1-yl]ethoxy]acetic acid, Zirtec, Zyrtec |
| (S)-cetirizine | |
| cetrorelix | SB-075 |
| cetuximab | C225, IMC-225, IMC-C225, L01XC06 |
| chenodeoxycholic acid | (4R)-4-[(3R,5R,7R,8R,9R,10S,13R,14R,17S)-3,7-dihydroxy-10,13-dimethyl-2,3,4,5,6,7,8,9,11,12,14,15,16,17-tetradecahydro-1H-cyclopenta[a]phenanthren-17-yl]pentanoic acid, CDCA, chenodeoxycholate |
| chlordiazepoxide | |
| chloroquine | chloraquine, chlorochine |
| chlorothiazide | Diuril |
| (−)-chlorpheniramine | |
| (+)-chlorpheniramine | 3-(4-chlorophenyl)-N,N-dimethyl-3-pyridin-2-yl-propan-1-amine, chlorphenamine |
| chlorpromazine | 3-(2-chlorophenothiazin-10-yl)-N,N-dimethyl-propan-1-amine, Chlorderazin, Chloropromazine, Contomin, Cromedazine, Largactil, Megaphen, Plegomazin, Propaphenin, Thorazine |
| chlorpropamide | chlorpropamid, diabaril, diabenese, diabetoral, diabinese, dynalase, meldian |
| chlorzoxazone | |
| cilastatin | MK 0791 |
| cilazapril | Ro 31-2848006 |
| cilazaprilat | Ro 31-3113 |
| cimetidine | Cimetag, Cimetidina, Cimetidinum, Eureceptor, Gastrobitan, Tagamet |
| cinacalcet | |
| cisapride | 4-amino-5-chloro-N-[1-[3-(4-fluorophenoxy)propyl]-3-methoxy-4-piperidyl]-2-methoxy-benzamide, Acenalin, Acpulsif, Alimix, Alipride, Cisapron, Enteropride, Prepulsid, Propulsid, Propulsin |
| cisplatin | |
| 9-cis-retinoic acid | 9-cis-retinoic acid, alitretinoin |
| cladribine | |
| clemastine | HS-592 |
| clidinium | 3-Hydroxy-1-methylquinuclidinium bromide benzilate |
| clofarabine | CAFdA, CI-F-araA, clofarex |
| clofibrate | ethyl 2-(4-chlorophenoxy)-2-methylpropanoate |
| clomiphene | clomifene |
| clomipramine | 3-(3-chloro-10,11-dihydro-5H-dibenzo[b,f]azepin-5-yl)-N,N-dimethylpropan-1-amine, Anafranil |
| clonidine | Adesipress, Catapresan, Catapres-TTS, Catarpres, Catarpresan, |

TABLE 2-continued

Exemplary Small Molecule Ligand Entities*

| Name | |
|---|---|
| clotrimazole | Catarpres-TTS, Chlornidinum, Clonidin, Duraclon, N-(2,6-dichlorophenyl)-4,5-dihydro-1H-imidazol-2-amine |
| clozapine | Asaleptin, Clorazil, Clozapin, Clozaril, Fazaclo, Iprox, Leponex, Lepotex |
| cocaine | |
| codeine | codicept, methylmorphine |
| coenzyme A | Aluzime, CoA, Coalip, CoASH, Co-A-SH, co-enzyme-A, HS-CoA |
| colchicine | |
| conivaptan | 4'-[(2-methyl-1,4,5,6-tetrahydroimidazo[4,5-d][1]benzazepin-6-yl) carbonyl]-2-phenylbenzanilide monohydrochloride, vaprisol, YM087, YM 087 |
| corticosterone | (11β)-11,21-dihydroxypregn-4-ene-3,20-dione, 4-pregnen-11β,21-diol-3,20-dione |
| cortisol | (11β)-11,17,21-trihydroxpregn-4-ene-3,20-dione, 4-pregnen-11β,17,21-triol-3,20-dione, hydrocortisone |
| crizotinib | PF2341066, PF 2341066, PF-2341066, xalkori |
| cyclacillin | |
| cyclothiazide | |
| cyproheptadine | Anarexol, Cypoheptadine, Cyproheptadiene, cyproheptidine, Dronactin, Eiproheptadine, Periactin, Periactine, Periactinol, Peritol |
| cyproterone acetate | |
| cytarabine | |

D

| | |
|---|---|
| dabigatran etexilate | Pradaxa BIBR 1048 |
| dabrafenib | GSK2118436, GSK2118436A, tafinlar |
| daclizumab | L04AC01, Ro-247375, RO-24-7375 |
| dalteparin | dalteparin sodium |
| danaparoid | ORG-10172 |
| danazol | anatrol |
| dantrolene | |
| darifenacin | 2-[1-[2-(2,3-dihydrobenzofuran-5-yl)ethyl]pyrrolidin-3-yl]-2,2-diphenyl-acetamide |
| dasatinib | BMS 345825, BMS 354825, BMS 35482513, sprycel |
| decitabine | 5-Azadeoxycytidine, AzadC, DAC, dezocitidine |
| denosumab | AMG-162, M05BX04 |
| desipramine | 3-(10,11-dihydro-5H-dibenzo[b,f]azepin-5-yl)-N-methylpropan-1-amine, active metabolite of imipramine, Norpramin, Pertofrane |
| desirudin | |
| deslanoside | ceglunat, desace, desacetyl-lanatoside C, lekozid |
| dexamethasone | desametasone, fluormethylprednisolone |
| dexmedetomidine | 4-[1-(2,3-dimethylphenyl)ethyl]-3H-imidazole, MPV 1440 |
| dextroamphetamine | (+)-alpha-methylphenylethylamine, d-amphetamine, D-amphetamine, D-am-phetamine, Dextroamphetamine, S(+)amphetamine |
| diazepam | |
| diazoxide | 7-chloro-3-methyl-4H-benzo[e][1,2,4]thiadiazine 1,1-dioxide, Eudemine, Hyperstat, Hypertonalum, Proglicem, Proglycem |
| diclofenac | 2-[2-(2,6-dichloroanilino)phenyl]acetic acid, Dichlofenal, Diclofenac acid, Diclofenacum, Dicrofenac, Novapirina, Pennsaid |
| diclofenamide | dichlofenamide, dichlorphenamide, glauconide |
| dicumarol | bishydroxycoumarin, melitoxin |
| dicyclomine | 2-diethylaminoethyl 1-cyclohexylcyclohexane-1-carboxylate, dicycloverin, dicycloverine |

TABLE 2-continued

Exemplary Small Molecule Ligand Entities*

| Name | |
|---|---|
| didanosine | dideoxyinosine, Videx |
| diethylstilbestrol | |
| digitoxin | crystodigin, digitoxoside, unidigin |
| digoxin | |
| dihydroergotamine | Angionorm, Dergotamine, Dihydergot, Dirgotarl, Endophleban, Ergomimet, Ergotonin, Migranal, Orstanorm |
| dihydrotestosterone | (5α,17β)-17-hydroxyandrostan-3-one, 5α-dihydrotestosterone, DHT |
| 1,25-dihydroxy-vitamin D3 | 1,25-dihydroxycholecalciferol, (1α,25-dihydroxy-vitamin D3), 1α,25-(OH)2D3, calcitriol |
| diltiazem | (2S,3S)-(+)-cis-3-Acetoxy-5-(2-dimethylaminoethyl)-2,3-dihydro-2-(4-methoxyphenyl)-1,5-benzothiazepin-4(5H)-one, (+)-cis-diltiazem, CRD-401, D-(cis)-diltiazem |
| diphenhydramine | 2-benzhydryloxy-N,N-dimethyl-ethanamine, alledryl, benadryl, benzhydramine, dimehydrinate, diphenylhydramine |
| dipyridamole | persantine |
| dobutamine | 4-[2-[4-(4-hydroxyphenyl)butan-2-ylamino]ethyl]benzene-1,2-diol, Dobutamina, Dobutaminum, Dobutrex, Inotrex |
| docetaxel | docetaxel anhydrous, EmDOC |
| dofetilide | |
| domperidone | 6-chloro-3-[1-[3-(2-oxo-3H-benzimidazol-1-yl)propyl]piperidin-4-yl]-1H-benzimidazol-2-one |
| donepezil | Aricept, E-2020 |
| dopamine | 3-hydroxytyramine, intropin |
| dorzolamide | cosopt Pf, dorzolamide hydrochloride |
| doxepin | |
| doxycycline | BMY-28689, Periostat |
| dromostanolone propionate | drostanolone |
| drospirenone | 6β,7β,15β,16β-dimethylene-3-oxo-17α-pregn-4-ene-21,17 carbolactone, dihydrospirorenone, ZK30595 |
| drotrecogin alfa | drotrecogin alfa (activated), HSDB 7366 |
| duloxetine | LY248686 |
| dydrogesterone | |

E

| | |
|---|---|
| econazole | |
| eculizumab | h5G1.1, h5G1.1VHC h5G1.1VLC |
| efalizumab | anti alphaL integrin, antiCD11 alpha, hu1124, Raptiva |
| eflornithine | 2-(difluoromethyl)ornithine, α-difluoromethyl-L-ornithine, DFMO |
| eletriptan | 3-[(1-methylpyrrolidin-2-yl)methyl]-5-(2-phenylsulfonylethyl)-1H-indole, Relpax, UK 116044 |
| enalapril | |
| enoxaparin | enoxaparin sodium, normiflo, PK-10169, RP-54563 |
| entacapone | OR-611 |
| enzalutamide | MDV3100, MDV-3100 |
| ephedrine | 2-methylamino-1-phenyl-propan-1-ol, Biophedrin, Ephedremal, Ephedrital, Ephedrol, Ephedrosan, Fedrin, Mandrin, Sanedrine |
| eplerenone | |
| eprosartan | (E)-α{[2-butyl-1-[(4-carboxyphenyl)methyl]-1H-imidazole-5-yl]methylene}-2-thiophenepropionic acid |
| eptifibatide | Integrelin, Intrifiban |
| ergonovine | Ergobasine, Ergoklinine, Ergometrin, Ergometrine, Ergoestretine, Ergotocine, Margonovine, Neofemergen, Secacorin, Secometri |
| ergotamine | Cornutamin, Ergostat, Ergotamin, Ergotartrat, Ergotartrate, Femergin, Gynergen, Migretamine, Secupanovyqyqvo |

TABLE 2-continued

Exemplary Small Molecule Ligand Entities*

| Name | |
|---|---|
| eribulin | E7389, ER 086526, eribulin mesylate, NSC-707389 |
| erlotinib | N-(3-ethynylphenyl)-6,7-bis(2-methoxyethoxy)quinazolin-4-amine, NSC 718781, OSI 744, OSI774, R 1415, tarceva |
| erythromycin-A | EM-A, erythromycin |
| erythropoietin {Sp: Human} | EPO |
| esomeprazole | (S)-omeprazole |
| 17β-estradiol | (8S,9S,13S,14S,17S)-13-methyl-6,7,8,9,11,12,14,15,16,17-decahydrocyclopenta[a]phenanthrene-3,17-diol, E2, estrogen, oestrodiol, oestrogen |
| estriol | |
| estrone | oestrone |
| estrone-3-sulphate | estrone-3-sulfate, estrone hydrogen sulfate, estrone hydrogen sulphate |
| etanercept | Rhu Tnfr:Fc, TNFR-Fc, TNFR-Fc fusion protein, TNR 001 |
| ethanol | |
| ethoxzolamide | diuretic C, ethamide, ethoxazolamide, ethoxyzolamide |
| ethylestrenol | |
| etomidate | Amidate, D-Etomidate, Hypnomidate, Lipuro, Propiscin, R 16659, Radenarcon |
| etoposide | (−)-etoposide, trans-etoposide, VP-16, VP 16-213 |
| etoricoxib | Arcoxia, Etoricoxibe, MK 0663, MK-0663, Nucoxia, Tauxib |
| everolimus | 23,27-Epoxy-3H-pyrido[2,1-c][1,4]oxaazacyclohentriacontine, rapamycin deriv., afinitor, certican, RAD001, RAD-001, rapamycin, 42-O-(2-hydroxyethyl)-, votubia, zortress |
| ezetimibe | sch 58235, SCH-58235 |

F

| Name | |
|---|---|
| febuxostat | adenuric, MX-67, Tei 6720, Tei-6720, TMX 67 |
| felbamate | 1,3-Bis(carbamoyloxy)-2-phenylpropane, ADD 03055, Felbamyl, Felbatol, Taloxa, W554 |
| felodipine | Plendil, Renedil |
| fenfluramine | |
| fenoldopam | SKF 82526 |
| fenoprofen | Feprona |
| fentanyl | duragesic, durogesic, fentanest, fentanil, fentanila, fentanylum, phentanyl, sentonil |
| fexofenadine | |
| finasteride | MK-906 |
| flecainide | |
| floxuridine | 5-fluoro-2′-deoxyuridine, floxidine |
| fludarabine | |
| fludrocortisone | (11beta)-9-fluoro-11,17,21-trihydroxpregn-4-ene-3,20-dione, 4-pregnen-9α-fluoro-11β,17,21-triol-16α-methyl-3,20-dione, 9α-Flourocortisol |
| flumazenil | |
| flunitrazepam | |
| 5-fluorouracil | |
| fluoxetine | |
| fluoxymesterone | 9a-Fluoro-11b-hydroxy-17a-methyltestosterone, Halotestin |
| fluphenazine | 2-[4-[3-[2-(trifluoromethyl)phenothiazin-10-yl]propyl]piperazin-1-yl]ethanol |
| flurbiprofen | |
| fluspirilene | 8-[4,4-bis(4-fluorophenyl)butyl]-1-phenyl-1,3,8-triazaspiro[4.5]decan-4-one |
| flutamide | SCH-13521 |
| fluticasone | |
| fluvastatin | Lescol |
| folinic acid | Leucovorin |
| fondaparinux | SC-52458 |
| forasartan | SC-52458 |
| formoterol | eformoterol |
| foscarnet | Carboxphosphonic acid, PFA, Phosphonocarboxylic acid, phosphonoformic acid |
| fosinopril | SQ-28555 |
| FSH {Sp: Human} | follitropin, human follicle stimulating hormone |
| fulvestrant | 7-alpha-[9-(4,4,5,5,5-pentafluoropentylsulphinyl)nonyl]estra-1,3,5-(10)-triene-3,17-beta-diol, faslodex, ICI182780, ICI 182780, ICI 182,780, ZD 182780, ZD 9238, ZM 182780 |
| furosemide | dihydroflumethiazide, frusemid, frusemide, metflorylthiazidine, methforylthiazidine |

G

| Name | |
|---|---|
| gabapentin | 1-(Aminomethyl)cyclohexaneacetic acid, 2-[1-(Aminomethyl)cyclohexyl]acetic acid, Bexal, CI 945, Gabamox, Gabapen, Generis, Go 3450, GOE 2450, GOE 3450, Neurontin |
| gallamine | 2-[2,6-bis(2-triethylammonioethoxy)phenoxy]ethyl-triethyl-azanium |
| gefitinib | iressa, N-(3-chloro-4-fluoro-phenyl)-7-methoxy-6-(3-morpholin-4-ylpropoxy)quinazolin-4-amine, ZD1839, ZD 1839 |
| gemcitabine | |
| gemfibrozil | |
| gemtuzumab ozogamicin | CDP 771, CMA 676, WAY-CMA 676 |
| gentamicin | |
| glibenclamide | glyburide |
| glimepiride | glimepride, roname |
| glipizide | glucotrol, glupitel, glydiazinamide, melizide, zidia |
| glucagon {Sp: Human, Mouse, Rat} | |
| golimumab | CNTO148, CNTO-148 |
| goserelin | decapeptide I, ICI 118630, zoladex |
| granisetron | BRL 43694, BRL-43694, Kytril |
| growth hormone 1 {Sp: Human} | GH1, GHN, hGH-N, pituitary growth hormone, somatotropin |
| guanabenz | N-(2,6-Dichlorobenzylidene)-N′-amidinohydrazine, NSC 68982, Wy 8678 |
| guanfacine | Estulic, Guanfacina, Guanfacinum, N-[(2,6-Dichlorophenyl)acetyl]guanidin, N-(diaminomethylidene)-2-(2,6-dichlorophenyl)-acetamide, Tenex |
| guanidine | |

H

| Name | |
|---|---|
| haloperidol | 4-[4-(4-chlorophenyl)-4-hydroxy-1-piperidyl]-1-(4-fluorophenyl)-butan-1-one, Aloperidin, Aloperidol, Aloperidolo, Brotopon, Eukystol, Galoperidol, Haldol, Halopoidol, Serenelfi |
| halothane | |
| heparin | |
| hydrochlorothiazide | |
| γ-hydroxybutyric acid | γ-hydroxybutyrate, GHB |
| hydroxyurea | droxia, hydrea, hydroxycarbamide, SQ-1089 |
| 25-hydroxyvitamin D3 | calcidiol |

I

| Name | |
|---|---|
| ibandronic acid | |
| ibritumomab tiuxetan | IDEC-Y2B8-yttrium ibritumomab tiuxetan, NSC-715848 |
| ibrutinib | PCI-32765 |
| ibuprofen | |
| icatibant | HOE140, HOE 140, D-Arg-[Hyp3,Thi[5],D-Tic[7],Oic[8]]BK |

TABLE 2-continued

Exemplary Small Molecule Ligand Entities*

| Name | |
|---|---|
| IGF1 {Sp: Human} | insulin-like growth factor 1, mechano growth factor, MGF, somatomedin-C |
| IL-11 {Sp: Human} | adipogenesis inhibitory factor, AGIF, interleukin-11, oprelvekin |
| iloprost | (5E)-5-[(3aS,4S,5R,6aS)-5-hydroxy-4-[(E,3S)-3-hydroxy-4-methyl-oct-1-en-6-ynyl]-3,3a,4,5,6,6a-hexahydro-1H-pentalen-2-ylidene]pentanoic acid |
| imatinib | CGP 57148, Gleevec, Glivec, STI571 |
| imidapril | |
| imidaprilat | |
| imipramine | Antideprin, Berkomine, Dimipressin, imidobenzyle, Intalpram, Melipramin, Melipramine, Nelipramin |
| imiquimod | 1-(4-amino-imidazo[4,5-c]quinolin-1-yl)-2-methylpropane, R837 |
| indomethacin | 2-[1-(4-chlorobenzoyl)-5-methoxy-2-methyl-indol-3-yl]acetic acid |
| infliximab | |
| insulin {Sp: Human} | |
| ipilimumab | L01XC11, MDX-010, MDX-101, MDX-CTLA-4 |
| ipratropium | [(1R,5R)-8-methyl-8-propan-2-yl-8-azoniabicyclo[3.2.1]oct-3-yl]3-hydroxy-2-phenyl-propanoate |
| irbesartan | 2-butyl-3-[2'-(1H-terazol-5-yl)biphenyl-4-yl)methyl)]-1,3-diazospironon-1-en-4-one, 2-n-butyl-4-spirocyclopentane-1-[(2'-(1H-tetrazol-5-yl)biphenyl-4-yl)methyl]2-imidazolin-5-one, SR 47436 |
| irinotecan | biotecan, CPT-11, (+)-irinotecan, irinotecan hydrochloride |
| isoflurane | |
| isoprenaline | 4-(1-hydroxy-2-propan-2-ylamino-ethyl)benzene-1,2-diol, Aludrine, Asiprenol, Assiprenol, Bellasthman, Isoprenalin, Isopropydrin, isoproterenol, Norisodrine, Respifral |
| isradipine | (±)-isradipine |
| (+)-isradipine | (+−)-isradipine, (+)-O5-methyl O3-propan-2-yl 4-(2,1,3-benzoxadiazol-7-yl)-2,6-dimethyl-1,4-dihydropyridine-3,5-dicarboxylate, O5-methyl O3-propan-2-yl 4-(2,1,3-benzoxadiazol-7-yl)-2,6-dimethyl-1,4-dihydropyridine-3,5-dicarboxylate, (+)-PN 200-110, PN200-110 |
| ivermectin | ivermectin B$_{1a}$ |
| ixabepilone | azaepothilone B, BMS-247550, BMS-247550-01, BMS 247550-1 |
| K | |
| ketamine | |
| ketoconazole | 1-[4-[4-[[(2R,4S)-2-(2,4-dichlorophenyl)-2-(imidazol-1-ylmethyl)-1,3-dioxolan-4-yl]methoxy]phenyl]piperazin-1-yl]ethanone, Ketoconazol, Ketoisdin, Nizoral, Panfungol |
| ketoprofen | |
| ketorolac | ketoralac, macril |
| L | |
| L-alanine | L-Ala |
| lamotrigine | |
| (R)-lansoprazole | Dexilant, Dexlansoprazole, Dextrolansoprazole, (+)-Lansoprazol, (+)-Lansoprazole, (R)-2-[[[3-Methyl-4-(2,2,2-trifluoroethoxy)-2-pyridinyl]methyl]sulfinyl]-1H-benzimidazole, (R)-2-[[[3-Methyl-4-(2,2,2-trifluoroethoxy)-2-pyridyl]methyl]sulfinyl]-1H-benzimidazole, R-(+)-Lansoprazole, T 168390, TAK 390 |
| lapatinib | FMM, GW572016, GW 572016, tykerb, tyverb |
| L-ascorbic acid | vitamin C |
| L-carnitine | |
| L-cysteine | L-Cys |
| leflunomide | HWA 486, HWA-486, lefunamide, SU-101, sulol |
| lepirudin | 1-L-Leucine-2-L-threonine-63-desulfohirudin |
| letrozole | femara |
| leuprolide | leuprorelin, lupron |
| levetiracetam | ucb L059, UCB-L 059 |
| levocabastine | (3R,4R)-1-[4-cyano-4-(4-fluorophenyl)cyclohexyl]-3-methyl-4-phenyl-piperidine-4-carboxylic acid, levocabastina, levocabastinum, Levocobastine |
| levodopa | 3,4-dihydroxy-L-phenylalanine, L-DOPA |
| levonorgestrel | 13β-Ethyl-17α-ethynyl-17β-hydroxygon-4-en-3-one, l-norgestrel |
| L-glutamic acid | L-Glu, L-glutamate, poly-L-glutamate |
| L-glutamine | |
| LH {Sp: Human} | human luteinising hormone, human luteinizing hormone |
| Li3+ | lithium ion |
| lidocaine | Anestacon, Esracaine, Gravocain, Leostesin, Lignocaine, Maricaine, Xylestesin, Xylocaine |
| linagliptin | BI-1356 |
| lipoic acid | α-lipoic acid, lipoate |
| liraglutide | N26-(Hexadecanoyl-gamma-glutamyle)-(34-arginine)GLP-1-(7-37)-peptide, NN2211, NN-2211, victoza |
| lisinopril | |
| lisuride | Lisurida, (+)-lisuride, Lisuridum, Lysuride |
| L-leucine | L-Leu |
| L-lysine | L-Lys |
| L-methionine | L-Met |
| L-α-methyldopa | aldomet, aldoril, dopamet, dopegyt, L-α-Methyl-3,4-dihydroxphenylalanine |
| lorazepam | 2H-1,4-Benzodiazepin-2-one, 7-chloro-5-(2-chlorophenyl)-1,3-dihydro-3-hydroxy-, ativan, lormetazepam, lorsilan, pro dorm, securit |
| losartan | 2-n-butyl-4-chloro-5-hydroxymethyl-1-[(2'-(1H-tetrazol-5-yl)biphenyl-4-yl)methyl]imidazole, DuP 753, MK-954 2-n-butyl-4-chloro-5-hydroxymethyl-1-[(2'-(1H-tetrazol-5-yl)biphenyl-4-yl)methyl]imidazole |
| lovastatin | 6α-methylcompactin, mevinolin, (+)-mevinolin |
| loxapine | cloxazepine, dibenzoazepine |
| L-proline | L-Pro |
| L-threonine | L-Thr |
| L-tyrosine | L-Tyr |
| lubiprostone | SPI-0211 |
| lumiracoxib | |
| L-valine | L-Val |
| M | |
| maprotiline | |
| maraviroc | 4,4-difluoro-N-[(1S)-3-[exo-3-(3-isopropyl-5-methyl-4H-1,2,4-triazol-4-yl)-8-azabicyclo[3.2.1]oct-8-yl]-1-phenylpropyl]cyclohexanecarboxamide, UK 427857, UK-427,857 |
| mazindol | Terenac |
| mecamylamine | |
| meclizine | 1-(p-Chloro-alpha-phenylbenzyl)-4-(m-methylbenzyl)piperazine, 1-(p-Chloro-a-phenylbenzyl)-4-(m-methylbenzyl)piperazine |
| medroxyprogesterone | Hydroxymethylprogesterone, MAP |
| mefenamic acid | 2-(2,3-dimethylanilino)benzoic acid, parkemed, ponstel |
| mefloquine | |
| memantine | |
| (−)-menthol | (1R,2S,5R)-5-methyl-2-propan-2-ylcyclohexan-1-ol, 5-methyl-2-propan-2-ylcyclohexan-1-ol, Levomenthol, l-Menthol |

TABLE 2-continued

Exemplary Small Molecule Ligand Entities*

| Name | |
|---|---|
| mequinol | 4-hydroxyanisole, 4-methoxyphenol, BMS-181158, hydroxyquinone methyl ether, leucobasal, leucodine B, menthyl anthranilate, p-hydroxyanisole |
| mesalazine | 5-aminosalicylic acid, 5-ASA, Mesalamine |
| metformin | |
| methadone | 6-Dimethylamino-4,4-diphenyl-3-heptanone, Algovetin, Amidone, Diaminon, dl-Methadone, Dolophin, Eptadone, Heptadone, Heptanon, Metasedin, Phenadone, Physeptone, (±)-Methadone, Racemic methadone, (RS)-Methadone, Sedo-Rapide |
| (−)-methadone | (6R)-6-dimethylamino-4,4-diphenyl-heptan-3-one, Levadone, Levomethadone, Levothyl, l-Methadone, L-Polamidon, l-Polamivet, Polamivet, (R)-Methadone |
| methamphetamine | |
| methazolamide | |
| methimazole | |
| methocarbamol | delaxin, methocal, miolaxin, neuraxin, parabaxin, robaxin, robaxin-750 |
| methotrexate | |
| methoxamine | 2,5-Dimethoxynorephedrine, Methoxamedrine, Methoxamin, Methoxaminum, Metossamina, Metoxamina, Pseudomethoxamine |
| methylergonovine | Basofortina, Methergen, Methergin, Methergine, Methylergobasin, Methylergobasine, Methylergonovin, Norforms, Partergin |
| α-methylnoradrenaline | Nordefrin |
| methysergide | 1-Methylmethylergonovine, Deseril, Desernil, Deseryl, Methysergid, Methysergidum, Metisergide |
| metoclopramide | 4-amino-5-chloro-N-(2-diethylaminoethyl)-2-methoxybenzamide, Maxolon, Metacloprominde, Methochlopramide, Metochlopramide, Metoclol, Moriperan, Primperan, Reliveran |
| metolazone | |
| metoprolol | 1-[4-(2-methoxyethyl)phenoxy]-3-(propan-2-ylamino)-propan-2-ol, Beatrolol, Lopresoretic, Preblok, Presolol, Seloken, Spesicor |
| metyrapone | mepyrapone |
| mexiletine | Mexiletene, Mexiletina, Mexiletine HCL, Mexiletinum, Mexitil, Mexityl |
| mianserin | (+−)-Athymil, Mianserina, Mianserine, Mianserinum, Mianseryna, (+−)-Norval |
| miconazole | 1-[2-(2,4-dichlorophenyl)-2-[(2,4-dichlorophenyl)methoxy]ethyl]imidazole, Brentan, Dactarin, Daktarin IV, Florid(nitrate), Miconazolo, Miconazolum, Minostate, Monistat |
| midazolam | Dormicum, Hypnovel, Midazolam, Versed |
| mifepristone | RU-486, RU486 |
| miglitol | N-hydroxylethyl-1-deoxynojirimycin |
| miglustat | miglustatum, NB-DNJ, N-butyl-1-deoxynojirimycin |
| milrinone | primicor |
| minoxidil | |
| misoprostol (methyl ester) | arthrotec, BRN 4155643, CCRIS 6859, cytotec, HSDB 3573, methyl-7-[(1R,2S,3R)-3-hydroxy-2-[(E)-4-hydroxy-4-methyl-oct-1-enyl]-5-oxo-cyclopentypeptanoate, misoprostolum, SC 29333 |
| moexipril | RS-10085, Univasc |
| mogamulizumab | KW-0761 |
| molindone | 3-ethyl-2-methyl-5-(morpholin-4-ylmethyl)-1,5,6,7-tetrahydroindol-4-one, Moban, Molindona, (+−)-Molindone, Molindonum |

TABLE 2-continued

Exemplary Small Molecule Ligand Entities*

| Name | |
|---|---|
| monobenzone | p-benzyloxyphenol |
| montelukast | |
| morphine | duromorph, meconium, morphia, morphina, morphinism, morphinum, morphium, moscontin, ospalivina |
| muromonab-CD3 | L04AA02, OKT-3 |
| mycophenolate mofetil | RS-61443, RS-61443-190 |
| mycophenolic acid | ERL-080 |

N

| Name | |
|---|---|
| nadolol | 5-[2-hydroxy-3-(tert-butylamino)-propoxy]tetralin-2,3-diol, Anabet, Corgard, Corzide, Nadololum, Solgol |
| nafamostat | FUT-175 |
| nafarelin | |
| NaHCO3— | sodium bicarbonate |
| nalbuphine | nalbufina |
| naloxone | l-Naloxone, n-Allylnoroxymorphone, N-Allyl-noroxymorphone, Nalone, nalossone, (−)-naloxone, (−)-Naloxone, Narcan, Narcon |
| naltrexone | 17-(cyclopropylmethyl)-4,5-epoxy-3,14-dihydroxy-(5α)-morphinan-6-one |
| nandrolone | 19-norandrostenolone |
| naphazoline | 2-Naphthalen-1-ylmethyl-4,5-dihydro-1H-imidazole, Nafazair, Naphazoline hydrochloride, Naphazoline Nitrate |
| naproxen | (S)-naproxen |
| naratriptan | N-methyl-2-[3-(1-methyl-4-piperidyl)-1H-indol-5-yl]-ethanesulfonamide |
| natalizumab | Anti-alpha4 integrin, Anti-VLA4 |
| nateglinide | starsis, trazec |
| neomycin | |
| nicardipine | (R,S)-nicardipine |
| nicotine | |
| nifedipine | Adalat, Cordipin, dimethyl 2,6-dimethyl-4-(2-nitrophenyl)-1,4-dihydropyridine-3,5-dicarboxylate, Nifediac, Nifedical, Procardia |
| niflumic acid | 2-[3-(trifluoromethyl)anilino]pyridine-3-carboxylic acid |
| nilotinib | AMN107, AMN 107, tasigna |
| nilutamide | |
| nimodipine | Nimotop, O5-(2-methoxyethyl) O3-propan-2-yl2,6-dimethyl-4-(3-nitrophenyl)-1,4-dihydropyridine-3,5-dicarboxylate |
| nisoldipine | O5-methyl O3-(2-methylpropyl) 2,6-dimethyl-4-(2-nitrophenyl)-1,4-dihydropyridine-3,5-dicarboxylate |
| nitisinone | |
| nitrendipine | O3-ethyl O5-methyl 2,6-dimethyl-4-(3-nitrophenyl)-1,4-dihydropyridine-3,5-dicarboxylate |
| N-methyl scopolamine | 3-oxa-9-azoniatricyclo[3.3.1.02,4]nonane, 7-(3-hydroxy-1-oxo-2-phenylpropoxy)-9,9-dimethyl-7-[(3-hydroxy-2-phenylpropanoyl)oxy]-9,9-dimethyl-3-oxa-9-azoniatricyclo[3.3.1.02,4]nonane, methylscopolamine, N-methylscopolamine, NMS |
| NO | nitric oxide, nitrogen monoxide |
| nomifensine | Alival |
| (−)-noradrenaline | noradrenaline |
| nordihydroguiaretic acid | NDGA |
| norethisterone | 17-Hydroxy-19-nor-17alpha-pregn-4-en-20-yn-3-one, norethindrone |
| nortriptyline | |

O

| Name | |
|---|---|
| obinutuzumab | GA101, gazyva |
| ofatumumab | GSK1841157, GSK 1841157, humax-CD20 |
| olanzapine | Olansek, Symbyax, Zyprexa |
| olmesartan | 4-(hydroxy-1-methylethyl)-2-propyl-1- |

TABLE 2-continued

Exemplary Small Molecule Ligand Entities*

| Name | |
|---|---|
| | {[2'-(1H-tetrazol-5-yl)-1,1'-biphenyl-4-yl]methyl}-1H-imidazole-5-carboxylic acid, Benicar, , Olmetec |
| omalizumab | IGE25, olizumab, RO3DX05, RG-3648, rhumab-E25 |
| omeprazole | |
| ondansetron | Zofran |
| orlistat | tetrahydrolipstatin, THL |
| ouabain | |
| oxiglutatione | glutathione disulfide |
| oxybutynin | 4-diethylaminobut-2-ynyl 2-cyclohexyl-2-hydroxy-2-phenyl-acetate |
| oxymetazoline | Hazol, Iliadin, Nafrine, Navisin, Nezeril, Oxylazine, Oxymethazoline, Rhinofrenol, Sinerol |
| oxytocin {Sp: Human, Mouse, Rat} | OT, pitocin, syntocinon |

P

| Name | |
|---|---|
| paclitaxel | 7-epipaclitaxel, 7-epi-paclitaxel, 7-epitaxol, 7-epi-taxol, taxol |
| pamoic acid | embonic acid |
| pancuronium | |
| panitumumab | ABX-EGF, ABX-EGF Mab |
| paracetamol | acetaminophen |
| paricalcitol | 19-nor-1α,25(OH)2D2 , 1α,25-dihydroxy-19-norvitamin D2, (7E,22E)-19-Nor-9,10-secoergosta-5,7,22-triene-1a,3b,25-triol, Zemplar |
| paroxetine | |
| pasireotide | SOM 230, SOM-230, SOM 320 |
| pazopanib | GW 786034, votrient |
| PDGF BB {Sp: Human} | becaplermin, platelet-derived growth factor BB homodimer |
| pepaptanib | EYEOO1, NX183 |
| pemetrexed | LY-231514, pemetrexed disodium |
| penicillin G | benzylpenicillin |
| pentagastrin | Peptavlon |
| (−)-pentazocine | pentazocine |
| pentobarbitone | Ethaminal, Mebubarbital, Nembutal, Neodorm, NSC 28708, Pentabarbitone, Pentobarbital, Pentobarbituric acid, Phetobarbitone, (±)-Pentobarbital, (±)-Pentobarbitone, Rivadorm, (RS)-Pentobarbital |
| pentostatin | 2'-deoxycoformycin, deoxycoformycin |
| perpolide | LY-127809, Pergolide mesylate |
| perindopril | S-9490 |
| perindoprilat | S-9780 |
| perphenazine | 2-[4-[3-(2-chlorophenothiazin-10-yl)propyl]piperazin-1-yl]ethanol, etaperazin, etaperazine, ethaperazine, perfenazine, trilafon |
| pertuzumab | 2C4, omnitarg |
| PGE1 | 7-[(1R,2S,3R)-3-hydroxy-2-[(E,3S)-3-hydroxyoct-1-enyl]-5-oxo-cyclopentypeptanoic acid, alprostadil, MR-256, PGE1, prostaglandin E₁ |
| PGE2 | 7-[3-hydroxy-2-(3-hydroxyoct-1-enyl)-5-oxo-cyclopentyl]hept-5-enoic acid, dinoprostone, minprositin E2, minprostin E2, prepidil, prostaglandin E2, prostarmon E, prostin E2 |
| PGI2 | epoprostenol, PGI2, prostacyclin, prostacyclin I2, prostaglandin I2, prostaglandin X, vasocyclin |
| phenindione | phenylindanedione |
| phenobarbital | Fenobarbital , Phenobarbitol , Phenobarbituric Acid, Phenylethylbarbiturate, Phenylethylbarbituric Acid |
| phenprocoumon | phenprocoumarol, phenprocumone |
| phentolamine | Dibasin, Fentolamin, Phenotolamine, Phentalamine, Regitin, Regitine, Regitipe, Rogitine |

Exemplary Small Molecule Ligand Entities*

| Name | |
|---|---|
| phenylephrine | Mesaton, Metaoxedrinum, Metasynephrine, Mezaton, m-Oxedrine, m-Sympatol, Neosynephrine, Visadron |
| phenytoin | |
| physostigmine | |
| picrotoxin | |
| pilocarpine | (3S,4R)-3-ethyl-4-[(3-methylimidazol-4-yl)methyl]oxolan-2-one, almocarpine, isoptocarpine [MeSH: Pilocarpine], pilocarpin, pilocarpol, pilokarpin, pilokarpol, syncarpine |
| pimecrolimus | SDZ ASM 981, SDZ-ASM 981 |
| pimozide | Haldol decanoate, Halomonth, Neoperidole, Opiran, Orap |
| pindolol | 1-(1H-indol-4-yloxy)-3-(propan-2-ylamino)-propan-2-ol, Betapindol, Calvisken, Carvisken, Decreten, Durapindol, Pectobloc, Pinbetol, Prinodolol, Visken |
| (−)-pindolol | |
| pioglitazone | |
| pirenperone | |
| pirenzepine | |
| plerixafor | Amd 3100, AMD3100, bicyclam JM-2987, JM 3100, SID791 |
| practolol | Dalzic, Eraldin, N-[4-[2-hydroxy-3-(propan-2-ylamino)-propoxy]phenyl]acetamide, Practalol, Practololo, Practololum, Praktololu, Teranol |
| pralatrexate | 10-propargyl-10-deazaaminopterin, PDX |
| pramipexole | Mirapex, Mirapexin, Sifrol |
| pranlukast | ONO RS-411 |
| pravastatin | |
| prazosin | Furazosin, Minipress, Prazosina, Prazosine, Prazosinum, Vasoflex |
| prednisolone | (11b)-11,17,21-Trihydroxypregna-1,4-diene-3,20-dione, (11beta)-11,17,21-Trihydroxypregna-1,4-diene-3,20-dione, DELTA.1-Cortisol |
| pregabalin | (2S)-3-(Aminomethyl)-5-methylhexanoic acid, (3S)-3-(Aminomethyl)-5-methylhexanoic acid, CI 1008, Gabanext 75, Lyrica, Mahagaba-75, Maxgalin 75, Neugaba 75, PD 144723, Pregalin 75, (S)-(+)-3-(Aminomethyl)-5-methylhexanoic acid, (S)-3-(Aminomethyl)-5-methylhexanoic acid, (S)-3-(Ammoniomethyl)-5-methylhexanoate, (S)-Pregabalin |
| primidone | |
| prinaberel | ERB 041, ERB-041 |
| probenecid | Benemid, Benuryl, Probalan |
| procainamide | |
| procaine | novocaine |
| procaterol | |
| progesterone | |
| propafenone | 1-[2-(2-hydroxy-3-(propylamino)propoxy]phenyl]-3-phenylpropan-1-one, Rythmol |
| propantheline | methyl-dipropan-2-yl-[2-(9H-xanthene-9-carbonyloxy)ethyl]azanium, propanthelinium, propanthelinum |
| propofol | 2,6-Diisopropylphenol, Ampofol, Anepol, Aquafol, Diprifusor, Diprivan, Diprofol, Disoprivan, Fresofol, ICI 35868, Propovan, Rapinovet, Recofol, Vetofol |
| propranolol | |
| (−)-propranolol | 1-naphthalen-1-yloxy-3-(propan-2-ylamino)-propan-2-ol, Avlocardyl, |

TABLE 2-continued

Exemplary Small Molecule Ligand Entities*

| Name | |
|---|---|
| propylthiouracil | Dociton, Euprovasin, Inderal, Propanolol, Proprasylyt |
| pyrimethamine | darachlor |
| pyruvic acid | pyruvate |

Q

| | |
|---|---|
| quetiapine | Seroquel |
| quinapril | Accupril, CI-906 |
| quinidine | |
| quinine | (1-butyl-4-piperidyl)methyl 2,3-dihydro-1,4-benzodioxine-8-carboxylate, (1-butylpiperidin-4-yl)methyl 2,3-dihydro-1,4-benzodioxine-8-carboxylate, 2,3-dihydro-benzo[1,4]dioxine-5-carboxylic acid 1-butyl-piperidin-4-ylmethyl ester |
| guinoprilat | CL-928 |

R

| | |
|---|---|
| raloxifene | Evista |
| ramelteon | rozerem, (S)-N-[2(1,6,7,8-tetrahydro-2H-indeno[5,4-b]furan-8-yl)ethyl]propionamide, (S)-N-(2-(1,6,7,8-tetrahydro-2H-indeno-(5,4)furan-8-yl)ethyl)propionamide, TAK375, TAK-375 |
| ramipril | HOE-498 |
| ranibizumab | rhuFab V2 |
| ranitidine | N-[2-[[5-(dimethylaminomethyl)-2-furyl]methylsulfanyl]ethyl]-N'-methyl-2-nitro-ethene-1,1-diamine, Zantac, Zinetac |
| rasagiline | Azilect |
| reboxetine | |
| regorafenib | 2-Pyridinecarboxamide, 4-[4-[[[[4-chloro-3-(trifluoromethyl)phenyl]amino]carbonyl]amino]-3-fluorophenoxy]-N-methyl-, BAY 73-4506, stivarga |
| repaglinide | AGEE-623ZW, novonorm, (−)-repaglinide |
| reserpine | |
| ribavirin | ribapak, ribofluranosyl carboxamide, tribavirin, viramid, virazole |
| rifampicin | rifampin |
| rilonacept | IL-1 Trap, interleukin-1 Trap |
| riluzole | 6-(trifluoromethoxy)benzothiazol-2-amine, Rilutek |
| risedronate | |
| risperidone | Risperdal, Risperidonum, Risperin, Rispolept, Rispolin, Sequinan |
| rituximab | HSDB 7455 |
| rivaroxaban | BAY 59-7939, Xarelto |
| rivastigmine | Ena 713 Free Base, Exelon |
| rizatriptan | N,N-dimethyl-2-[5-(1,2,4-triazol-1-ylmethyl)-1H-indol-3-yl]-ethanamine |
| rocuronium | Esmeron, Zemuron |
| rofecoxib | Ceoxx, Vioxx |
| rosiglitazone | 5-[[4-[2-(methyl-pyridin-2-ylamino)ethoxy]phenyl]methyl]-1,3-thiazolidine-2,4-dione, rosiglizole |
| rosuvastatin | ZD4522 |
| rotigotine | N-0437, Neupro |
| roxithromycin | erythromycin 9-(-O-[2-methoxyethoxy]methyloxime) |
| ruxolitinib | INC424, INCB 18424, jakafi, jakavi |

S

| | |
|---|---|
| S-adenosyl methionine | ademetionine, AdoMet, S-adenosyl-L-methionine, S-adenosylmethionine, SAMe, SAM-e |
| salbutamol | 2-(hydroxymethyl)-4-[1-hydroxy-2-(tert-butylamino)-ethyl]-phenol, Aerolin, albuterol, Broncovaleas, Novosalmol, Proventil, Salbuhexal, Sultanol, Ventolin |
| salicylic acid | salicylate |
| salmeterol | 2-(hydroxymethyl)-4-[1-hydroxy-2-[6-(4-phenylbutoxy)hexylamino]ethyl]-phenol, Aeromax, Astmerole, GR 33343X, Salmeterolum |
| saguinavir | |
| saxagliptin | BMS-477118 |
| scopolamine | beldavrin, euscopol, hyoscine, hyosol, isoscopil, kwells, scopamin, tranaxine, triptone |
| secretin {Sp: Human} | |
| selegiline | Deprenyl, L-Deprenalin, L-deprenyl, Selegiline |
| sertindole | 1-[2-[4-[5-chloro-1-(4-fluorophenyl)-indol-3-yl]-1-piperidyl]ethyl]imidazolidin-2-one, SerLect, Sertindol, Sertindolum |
| sertraline | |
| sibutramine | 1-[1-(4-chlorophenyl)cyclobutyl]-N,N,3-trimethylbutan-1-amine, medaria, meridia , reductil , sibutramina |
| sildenafil | sildenafil citrate, viagra |
| simvastatin | |
| sitagliptin | Januvia, MK-0431 |
| sitaxsentan | TBC11251, TBC-11251 |
| sivelestat | LY544349, ONO-5046 |
| (−)-SKF-82526 | |
| (+)-SKF-82526 | 6-chloro-1-(4-hydroxphenyl)-2,3,4,5-tetrahydro-1H-3-benzazepine-7,8-diol, corlopam, fenoldopam |
| sorafenib | BAY 43-9006, nexavar |
| spirapril | Renormax, SCH-33844 |
| spironolactone | 17-hydroxy-7α-mercapto-3-oxo-17α-pregn-4-ene-21-carboxylic acid γ-lactone acetate, Aldactazide, Aldactone, Berlactone, Novo-Spiroton, Spiractin, Spirotone, Verospiron |
| succinylcholine | |
| sufentanil | |
| sufinpyrazone | G 28315, NSC 75925, suphinpyrazone |
| sulfasalazine | azulfidine |
| sulindac | |
| sulpiride | Abilit, Aiglonyl, Coolspan, dl-Sulpiride, Dobren, Dogmatil, Dogmatyl, Dolmatil, Eglonyl, Guastil, Meresa, Miradol, Mirbanil, Misulvan, N-(1-Ethyl-2-pyrrolidinylmethyl)-2-methoxy-5-sulfamidobenzamide, N-[(1-Ethyl-2-pyrrolidinyl)methyl]-5-sulfamoyl-o-anisamide, Neogama, Omperan, (±)-Sulpiride, Pyrikappl, RD 1403, Sernevin; Splotin, Sulpirid, Sulpiride, Sulpitil, Sulpyrid, Sursumid, Synedil, Trilan |
| (−)-sulpiride | N-[(1-ethylpyrrolidin-2-yl)methyl]-2-methoxy-5-sulfamoylbenzamide, S-(−)-sulpiride |
| (+)-sulpiride | N-[[(2R)-1-ethylpyrrolidin-2-yl]methyl]-2-methoxy-5-sulfamoylbenzamide, R-(+)-sulpiride |
| sumatriptan | 1-[3-(2-dimethylaminoethyl)-1H-indol-5-yl]-N-methyl-methanesulfonamide, Imigran, Imitrex, Sumatran, Sumatriptanum, Sumax |
| sunitinib | SU11248, sutent |
| suramin | Antrypol, Belganyl, Farma, Fourneau, Germanin, MoranylNaganol, Naphuride, Suramine |

T

| | |
|---|---|
| T3 | 3,5,3'-triodo-L-thyronine, Liothyronine, T3, thyroid hormone, Triiodothyronine |
| T4 | (2S)-2-amino-3-[4-(4-hydroxy-3,5-diiodophenoxy)-3,5-diiodophenyl]propanoic acid, levothyroxine, L-thyroxine, T4, 1-4, thyroxine |

TABLE 2-continued

Exemplary Small Molecule Ligand Entities*

| Name | |
|---|---|
| tacrolimus | fujimycin, modigraf, protopy, tacrolimus anhydrous |
| tamibarotene | AM80 |
| tamoxifen | 2-[4-[(Z)-1,2-diphenylbut-1-enyl]phenoxy]-N,N-dimethyl-ethanamine |
| tamsulosin | 5-[2-[2-(2-ethoxyphenoxy)ethylamino]propyl]-2-methoxy-benzenesulfonamide, Flomax, Flomaxtra , KEGG: G07124, (−)-(R)-S-[2-[[2-(o-ethoxyphenoxy)ethyllamino]propyl]-2-methoxpenzenesulfonamide, Tamsulosin, Tamsulosina, Tamsulosine, Tamsulosin hydrochloride, Urimax, (−)-YM617 |
| telmisartan | 4'-[(1,4'-dimethyl-2'propyl[2,6'-bi-1H-benzimidazol]-1'-yl)methyl]-[1,1'-biphenyl]-2-carboxylic acid |
| teniposide | VM-26 |
| terbutaline | 5-[1-hydroxy-2-(tert-butylamino)-ethyl]benzene-1,3-diol, Brican, Bricanyl, Bricar, Bricaril, Bricyn, Terbutalin, Terbutalina |
| terfenadine | |
| teriflunomide | A77 1726, flucyamide, HMR-1726 |
| teriparatide | PTH-(1-34) (human) |
| testosterone | (17β)-17-hydroxyandrost-4-en-3-one |
| tetrabenazine | TBZ |
| tetrahydrobiopterin | BH$_4$, Kuvan, THB |
| Δ9-tetrahydrocannabinol | delta1-THC, delta9-THC, Deltanyne, Δ$^9$-Tetrahydrocannabinol, Δ$^9$-THC, Dronabinol, Marinol, tetrahydrocannabinol |
| theophylline | 1,3-dimethyl-7H-purine-2,6-dione, Doraphyllin, Elixophyllin, Elixophylline, Lanophyllin, Liquophylline, Maphylline, Medaphyllin, Parkophyllin |
| thioguanine | 2-amino-6-mercaptopurine, 2-amino-6-purinethiol, 6-mercaptoguanine, 6-thioguanine |
| thiopental | |
| thioridazine | 10-[2-(1-methyl-2-piperidyl)ethyl]-2-methylsulfanyl-phenothiazine, Mallorol, Malloryl, Melleril, Mellaril, Mellerets, Mellerette, Melleretten, Melleril, Thioridazin |
| thiothixene | N,N-dimethyl-9-[3-(4-methylpiperazin-1-yl)propylidene]thioxanthene-2-sulfon amide |
| tiagabine | |
| timolol | 1-[(4-morpholin-4-yl-1,2,5-thiadiazol-3-yl)oxy]-3-tert-butylamino-propan-2-ol, Blocadren, timolol maleate |
| tinzaparin | innohep |
| tiotropium | Spiriva |
| tirofiban | |
| tocilizumab | L04A007, MRA, R-1569, RG-1569, RHPM-1, roactemra |
| tofacitinib | CP 690550, CP-690550, tasocitinib, xeljanz |
| tolazamide | diabewas, tolazolamide |
| tolbutamide | dolipol, orabet, orinase, rastinon |
| tolcapone | Ro 40-7592 |
| tolterodine | 2-[3-(dipropan-2-ylamino)-1-phenyl-propyl]-4-methyl-phenol |
| topiramate | epitomax, MCN-4853, RWJ-17021 |
| toremifene | toremifine |
| tositumomab | |
| trabectedin | ecteinascidin 743, ET-743, yondelis |
| trametinib | GSK1120212, GSK1120212B, JTP 74057, mekinist |
| trandolapril | |
| trandolaprilat | |
| tranexamic acid | |
| trans flupenthixol | beta-Flupenthixol, (E)-Flupenthixol, Emergil, FLUPENTHIXOL, Flupentixol hydrochloride, Lopac-F-114, Metamin, trans(E)Flupenthixol, trans-(E)-Flupentixol, trans-Flupentixol |

TABLE 2-continued

Exemplary Small Molecule Ligand Entities*

| Name | |
|---|---|
| tranylcypromine | jatrosom, parnate |
| trastuzumab | herceptin |
| trastuzumab emtansine | ado-trastuzumab emtansine, PRO-132365, RG-3502, trastuzumab-Mcc-Dm1 |
| trazodone | 8-[3-[4-(3-chlorophenyl)piperazin-1-yl]propyl]-6,8,9-triazabicyclo[4.3.0]nona-2,4,9-trien-7-one, Beneficat, Bimaran, Desirel, Desyrel, Molipaxin, Trazalon, Trazodil, Trazodon, Trazonil |
| treprostinil | diolamine, remodulin, treprostinil sodium, tyvaso |
| triamcinolone | (11beta,16alpha)-9-Fluoro-11,16,17,21-tetrahydroxypregna-1,4-diene-3,20-dione, 16a-Hydroxy-9a-fluoroprednisolone, Fluoxiprednisolone |
| triamcinolone acetonide | |
| triamterene | Dyrenium |
| trifluoperazine | 10-[3-(4-methylpiperazin-1-yl)propyl]-2-(trifluoromethyl)phenothiazine |
| triflupromazine | Vesprin |
| trilostane | vetoryl, WIN 24,540, WIN-24540 |
| triprolidine | 2-[(E)-1-(4-methylphenyl)-3-pyrrolidin-1-yl-prop-1-enyl]pyridine |
| TSH {Sp: Human} | thyroid-stimulating hormone, thyrotropin |

U

| | |
|---|---|
| ustekinumab | CNTO-1275, L04A005, TT-20 |

V

| | |
|---|---|
| valacyclovir | |
| valganciclovir | |
| valsartan | |
| vandetanib | caprelsa, CH 331, zactima, ZD6474, ZD 6474, ZD-6474 |
| vapreotide | BMY 41606, CCRIS 6495, RC 160, RC-160 |
| varenicline | Champix, Chantix, CP 526555 |
| vasopressin {Sp: Human, Mouse, Rat} | AVP, ADH, antidiuretic hormone, arginine vasopressin, argipressin |
| vecuronium | |
| vemurafenib | 1-Propanesulfonamide, N-[3-[[5-(4-chlorophenyl)-1H-pyrrolo[2,3-b]pyridin-3-yl]carbonyl]-2,4-difluorophenyl]-, PLX4032, RG7204, zelboraf |
| verapamil | 2-(3,4-dimethoxyphenyl)-5-[2-(3,4-dimethoxyphenyl)ethyl-methylamino]-2-propan-2-ylpentanenitrile |
| vidarabine | |
| vigabatrin | CPP-109 |
| vildagliptin | |
| vinblastine | 29060-LE |
| vincristine | 22-oxovincaleukoblastine, kyocristine, leurocristine sulfate, NSC-67574 |
| vitamin D3 | (3S,5Z,7E,14xi)-9,10-secocholesta-5,7,10-trien-3-ol, 9,10-Secocholesta-5,7,10(19)-trien-3-beta-ol, Cholecalciferol |
| vorinostat | suberoylanilide hydroxamic acid |

W

| | |
|---|---|
| warfarin | jantoven, panwarfin, warfarin potassium, warfarin sodium |

X

| | |
|---|---|
| xylometazoline | Novorin , Otriven, Otrivin , Otrivine, Otrix, Xilometazolina, Xylometazolinum, Xylomethazoline |

Y

| | |
|---|---|
| yohimbine | aphrosol, corynine, quebrachin, quebrachine, yohimbin |

TABLE 2-continued

Exemplary Small Molecule Ligand Entities*

| Name | Z |
|---|---|
| zafirlukast | |
| zalcitabine | DDC, dideoxycytidine |
| zaleplon | |
| zidovudine | 3'-azido-3'-deoxythymidine, AZT |
| zileuton | ZYFLO |
| ziprasidone | 6-chloro-5-[2-[4-(7-thia-8-azabicyclo[4.3.0]nona-1,3,5,8-tetraen-9-yl)piperazin-1-yl]ethyl]-1,3-dihydroindol-2-one, Geodon, Zeldox |
| zofenopril | SQ-26900 |
| zofenoprilat | |
| zoledronic acid | zoledronate |
| zolmitriptan | 4-[[3-(2-dimethylaminoethyl)-1H-indol-5-yl]methyl]oxazolidin-2-one, AscoTop, (S)-4-({3-[2-(dimethylamino)ethyl]-1H-indol-5-yl}methyl)-1,3-oxazolidin-2-one, Zomig, Zomigon |
| zolpidem | |

* = Additional exemplary small molecule ligand entities may be found, inter alia, at www.hit2lead.com In some embodiments, a small molecule ligand entity is or comprises a small molecule approved by the U.S. Food and Drug Administration (FDA). Exemplary FDA-approved small molecules may be found at www.fda.gov/drugs/informationondrugs/approveddrugs/.

In some embodiments, a small molecule ligand entity is or comprises a small molecule that did not receive FDA approval due to off-target effects (e.g., a risk of undesired effects on the Central Nervous System).

In some embodiments, lipidation of a small molecule ligand entity may improve the binding constant of the small molecule.

According to various embodiments, it may be necessary to test a particular small molecule ligand entity for amenability to lipidation at a specific site. It is contemplated as within the scope of the present invention that the development of libraries of small molecule ligand entities, each lipidated at a different site, may be desired in order to determine which site(s) on the small molecule are amenable to lipidation without causing a loss of function or activity.

Lipid Entities

Any of a variety of lipid entities may be utilized in accordance with the present invention. According to various embodiments, a lipid entity is or comprises an entity capable of insertion into a lipid bilayer (e.g., a cell membrane). In some embodiments, a lipid entity is capable of incorporating into a lipid raft in a lipid bilayer (e.g., a cell membrane). In some embodiments, the lipid entity is selected from the group consisting of fatty acids, cholesterol, 1,2-bis(diphenylphosphino)ethane(DPPE), polyethers, pepducins, gangliosides, and derivatives thereof. Non-limiting examples of lipid entities include myristic, palmitic, stearic, palmitoleic, and oleic acids. In some embodiments, a lipid entity is palmitic acid. In some embodiments, a lipid entity is the ganglioside $GM_1$.

In some embodiments, lipidation may comprise N-myristoylation. As used herein, "N-myristoylation" refers to the attachment of a myristate to an N-terminal glycine.

In some embodiments, lipidation may comprise palmitoylation. As used herein "palmitoylation" refers to the creation of a thioester linkage of long-chain fatty acids on one or more cysteine residues present in a peptide or protein.

In some embodiments, lipidation comprises GPI-anchor addition. As used herein "GPI-anchor addition" refers to the linkage of glycosyl-phosphatidylinositol (GPI) to the C-terminus of a protein.

In some embodiments, lipidation comprises prenylation. As used herein "prenylation" refers to the creation of a thioether linkage of an isoprenoid lipid (e.g., farnesyl (C-15) or geranylgeranyl (C-20)) to a cysteine present in a peptide or protein. In some embodiments, lipidation comprises geranylation. In some embodiments, lipidation includes geranylgeranylation. In some embodiments, lipidation comprises the association of a ligand entity with any compound that is soluble in a cellular membrane (e.g., 10:1 in equilibrium constant $K_{assoc} \geq 10$).

In some embodiments, lipidation may comprise one or more of the following: attachment of diacylglycerol to the side chain of an N-terminal cysteine of a peptide or protein via the sulfur atom; attachment O-octanoyl to a serine or threonine of a peptide or protein; and attachment of S-archaeol to a cysteine of a peptide or protein. In some embodiments, wherein a peptidic ligand entity comprises natural amino acids, lipidation may occur, for example, at any lysine, glutamic acid, aspartic acid, serine, threonine, cysteine, and/or tyrosine. In some embodiments wherein a peptidic ligand entity is or comprises one or more synthetic amino acids, lipidation may occur at any ornithine.

In some embodiments, lipidation may include fluorination. In some embodiments fluorination includes the addition of one or more $C_6F_{13}$ chains. Without wishing to be held to a particular theory, it is thought that the presence of one or more $C_6F_{13}$ chains may allow a lipid entity to segregate from hydrocarbon lipid membrane components (see J. Am. Chem. Soc. 2007, 129, 9037-9043; J. Phsy. Chem. B, 2008, 112, 8250-8256; J. Am. Chem. Soc., 2009, 131, 12091-12093).

In some embodiments, the presence of at least one alkene in the structure of a lipid entity provides increased fluidity in a membrane (i.e., greater ability to move within the membrane) as compared to similar lipid entities lacking at least one alkene. In some embodiments, a lipid entity with greater fluidity is able to provide enhanced activity towards targets (e.g., receptors, ion channels, or enzymes) with a low density in a membrane. Without wishing to be held to a particular theory, it is possible that lipid entities with increased ability to move within a membrane are able to encounter a low density target faster than a lipid entity with less mobility within a membrane.

In some embodiments, a lipid entity is or comprises a lipid listed in Table 3:

TABLE 3

| Exemplary Lipid Entities* | |
|---|---|
| Name | Sequence/Structure |
| Myristic acid | [structure: HO-C(=O)-(CH2 chain)-(CH2)$_n$] |
| Palmitic acid | [structure: HO-C(=O)-(CH2 chain)-(CH2)$_n$] |
| Stearic acid | [structure: HO-C(=O)-(CH2 chain)-(CH2)$_n$] |
| Palmitoleic acid | [structure: HO-C(=O)-chain with cis double bond-(CH2)$_{n=3}$] |
| Oleic acid | [structure: HO-C(=O)-chain with cis double bond-(CH2)$_{n=3}$] |
| Cholesterol | [structure: glycine-conjugated cholesterol] |
| DPPE and derivatives | [structure: DPPE derivative with R$^1$ groups]<br>for example, where R$^1$ = C$_6$H$_{13}$ or C$_6$F$_{13}$ |
| GM1 | [structure: GM1 ganglioside with R$^2$HN and R$^1$, $n = 1, 2$] |
| GM2 | [structure: GM2 ganglioside with R$^2$HN and R$^1$, $n = 1, 2$] |

TABLE 3-continued

Exemplary Lipid Entities*

| Name | Sequence/Structure |
|---|---|
| GM3 | 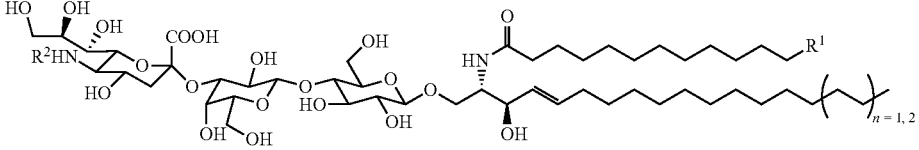 |
| 1,2-bis(diphenyl-phosphino)ethane (DPPE) | |
| α-Linolenic acid | 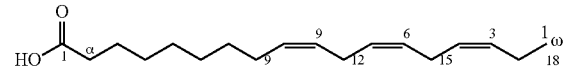 |
| Eicosapentaenoic acid (EPA) |  |
| Docosahexaenoic acid (DHA) | 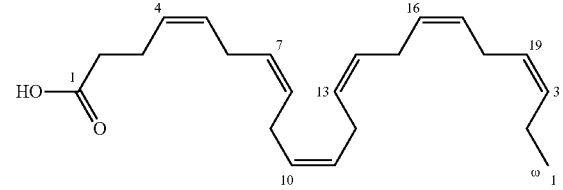 |
| DPPC | 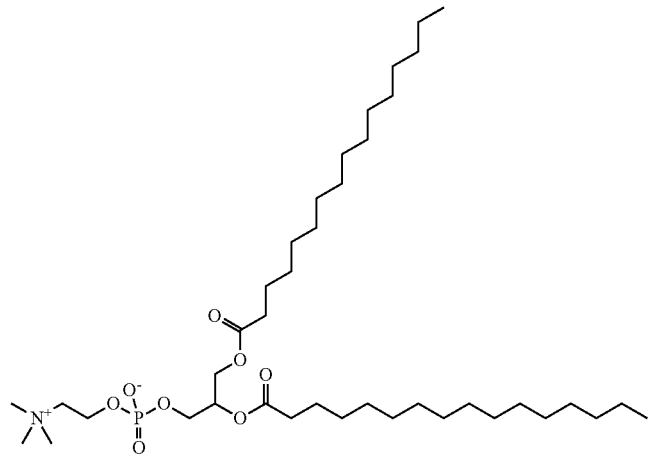 [SMILES: CCCCCCCCCCCCCCCC(=O)OCC(COP(=O)([O-])OCC[N+](C)(C)C)OC(=O)CCCCCCCCCCCCCCC] |
| DOPS | |
| DOPC | |
| Glycosphingo-lipids | |
| Sphingolipids | |
| PIP2 | |
| Ceramides | |
| Sterols | |
| Fluorinated-GM1 | |
| Fluorinated-GM2 | |
| Fluorinated-GM3 | |

*Additional exemplary lipid entities may be found, inter alia, at www.avantilipids.com Linkers In some embodiments, provided lipidated ligand agents comprise a linker entity. In some embodiments, association of the ligand entity and lipid entity with a linker does not alter the three dimensional conformation of either the ligand entity or the lipid entity as compared to the ligand entity and lipid entity alone. In some embodiments, association with a linker results in an alteration of the three dimensional structure of at least one of the ligand entity and lipid entity.

According to various embodiments, a linker may be selected based, at least in part, on application-specific factors. Non-limiting examples of such factors include the specific chemistries of a particular ligand entity/lipid entity combination, the efficacy of a particular linker in in vitro or in vivo models, the desired degree of solubility, and distance required for a ligand entity to reach a target. In some embodiments, a linker, for example, a non-peptidic linker, has a length of between about 2 Å and 175 Å, inclusive. In some embodiments, a linker is between 30 Å and 150 Å, inclusive.

In some embodiments, the linker entity is or comprises a peptide. According to various embodiments, peptide linkers may be designed such that one or more α-helices are formed between a ligand entity and a lipid entity before, during, or after association with the linker. In some embodiments, a peptidic linker may comprise a plurality of α-helices. In some embodiments, the plurality of α-helices are consecutive. In some embodiments, a plurality of α-helices is 2, 3, 4, 5, 6, 7, 8, 9, 10, 15, 20, or more α-helices. In some embodiments, a peptide linker is between 2 and 18 amino acid residues in length. In some embodiments, a peptide linker is between 5 and 10 amino acid residues in length.

In some embodiments, a peptidic linker may comprise repeating units, for example a plurality of repeating glycine-asparagine (GN) units. In some embodiments, a peptidic linker may comprise an epitope tag (e.g., a c-Myc tag) or other marker to allow for identification and/or characterization of provided agents and their fate in vitro and/or in vivo.

In some embodiments, the linker is or comprises a non-peptidic linker. In some embodiments, non-peptide linkers may be a synthetic polymer. According to various embodiments, the synthetic polymer may be any of a variety of lengths. In some embodiments, a linker comprising a synthetic polymer comprises a monomeric unit of the polymer. In some embodiments, a linker comprising a synthetic polymer comprises two or more monomeric units of a synthetic polymer (e.g., 2, 3, 4, 5, 6, 7, 8, 9, 10, 20, 30, 40, 50, 100 or more monomeric units).

In some embodiments, a linker is or comprises at least one molecule of polyethylene glycol (PEG). Specific, non-limiting examples of suitable polymeric linkers include linkers with one or more monomeric units according to one of the following formulas:

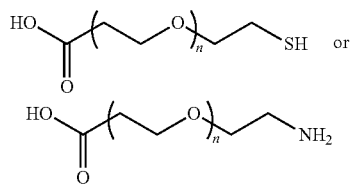

where n represents an integer greater than or equal to 1. In some embodiments, n is an integer between 2 and 50, 4 and 24, and/or 8 and 24, inclusive.

In some embodiments, a linker is or comprises 1-Ethyl-3-(3-Dimethylaminopropyl)carbodiimide (EDAC), Benzophenone-4-Isothiocyanate, Bis-((N-Iodoacetyl)Piperazinyl) Sulfonerhodamine, Succinimidyl 2-(2-Pyridyldithio) Propionate (SPDP), 4-Azido-2,3,5,6-Tetrafluorobenzoic acid (ATFB), (N-((2-Pyridyldthio)ethyl)-4-Azidosalicylamide), Succinimidyl trans-4-(maleimidylmethyl)cyclohexane-1-carboxylate (SMCC), and/or N-(t-BOC)-aminooxyacetic acid. Additional linkers may be found at: www.interchim.eu/catalogue/431/crosslinker-modifiers.html and www.piercenet.com/cat/crosslinking-reagents. Those of skill in the art will be able to identify additional candidate linkers, inter alia, according to known methods.

In some embodiments, a linker is formed, at least in part, as a result of a click reaction as further described below. In some embodiments, the click reaction is an azide-alkyne Huisgen cycloaddition reaction Production of Soluble Lipidated Ligand Agents In some embodiments, the present invention provides systems for production soluble lipidated ligand agents including providing at least one ligand entity, providing at least one lipid entity, and associating the at least one ligand entity and the at least one lipid entity to form a soluble lipidated ligand agent.

Associating Ligand and Lipid Entities

According to various embodiments, a ligand entity is associated with a lipid entity in any of a variety of ways. In some embodiments, association may be via covalent bonding, non-covalent bonding, or any other application-appropriate mechanism.

In some embodiments, a ligand entity is covalently bound to a lipid entity. In some embodiments, the ligand entity and lipid entity are directly covalently bound to one another, while, in other embodiments, the ligand entity and the lipid entity are indirectly covalently bound. As a specific, non-limiting example, in some embodiments, a ligand entity is covalently bound to a linker, and the linker is covalently bound to the lipid entity.

In some embodiments, a ligand entity is associated with a lipid entity such that the N-terminus of the ligand entity is free (i.e., not bound to the lipid entity or a linker). In some embodiments, a ligand entity is associated with a lipid entity such that the C-Terminus of the ligand entity is free. In some embodiments, a ligand entity is associated with a lipid entity such that both the N-terminus and C-terminus of the ligand entity are free.

In some embodiments, association between a ligand entity and a lipid entity (optionally with a linker) will result in an increase in one or more of the potency, activity, or half-life of a ligand entity as compared to the ligand entity alone. In some embodiments, association between a ligand entity and a lipid entity (optionally with a linker) will result in a decrease in one or more of the potency, activity, or half-life of a ligand entity as compared to the ligand entity alone. In some embodiments, an improvement in one or more of potency, activity, and/or half-life is defined as a statistically significant improvement in one or more desired characteristics or attributes in a tethered or lipidated ligand entity as compared to the ligand entity alone in an in vitro and/or in vivo assay. In some embodiments, association between a ligand entity and a lipid entity (optionally with a linker) decreases one or more side effects associated with administration of the ligand entity alone.

In some embodiments, a ligand entity and lipid entity may each be considered a reactable entity. In some embodiments, a ligand entity and/or lipid entity may be considered a reactable entity when it comprises the ligand or lipid entity and a moiety that facilitates association between the ligand entity and the lipid entity (e.g., a click chemistry reactive moiety). In some embodiments, the present invention provides sets of reactable entities. In some embodiments, the set comprises a plurality of different ligand entities with the same first reactive moiety. In some embodiments, the set comprises a plurality of different ligand entities that do not all have the same reactive moiety. In some embodiments, the set comprises a plurality of different lipid entities with the same reactive moiety. In some embodiments, the set comprises a plurality of different lipid entities that do not all have the same reactive moiety.

Click Chemistry

In some embodiments, a ligand entity and a lipid entity may be associated by or through one or more click reactions. Generally, click reactions provide a versatile chemical platform for molecular tailoring and have become a popular method of bioconjugation due to the high reactivity and selectivity of such reactions, even in biological media. See Kolb, H. C.; Finn, M. G.; Sharpless, K. B. *Angew. Chem. Int. Ed.* 2001, 40, 2004-2021; and Wang, Q.; Chan, T. R.; Hilgraf, R.; Fokin, V. V.; Sharpless, K. B.; Finn, M. G. *J. Am. Chem. Soc.* 2003, 125, 3192-3193; Thirumurugan et al., Click Chemistry for Drug Development and Diverse Chemical-Biology Applications, *Am. Chem. Soc.,* 2013, 113:4905-4979. The phrase "click chemistry" is applied to a collection of supremely reliable and self-directed organic reactions (Kolbi H. C; Finn, M. G.; Sharpless, K. B. *Angew. Chem. Int. Ed.* 2001, 40, 2004-2021) that tend to involve high-energy ("spring-loaded") reagents with well-defined reaction coordinates, and that give rise to selective bond-forming events of wide scope. Exemplary such reactions include, but are not limited to, cycloaddition reactions such as Diels-Alder cycloadditions, inverse demand Diels-Alder cycloadditions, Huisgen cycloadditions, Copper (I)-catalyzed Azide-Alkyne Cycloadditions (CuAAC), other such 1,3-dipolar cycloadditions, certain types of [4+1] cycloadditions between isonitriles and tetrazines, certain types of nucleophilic substitution reactions to small strained rings such as epoxy and aziridine compounds, certain types of carbonyl-chemistry-like formation of ureas, certain types of addition reactions to carbon-carbon double bonds, and certain types of reactions of mercaptans with double or triple bonds ("thiol" click reactions).

As used herein, the phrase "click chemistry reactive moiety" refers to any moiety capable of reacting with another moiety to effect a click reaction. For example, in some embodiments, a click chemistry reactive moiety is an azide-containing group. In some embodiments, a click chemistry reactive moiety is an alkyne-containing group. In some embodiments, a click chemistry reactive moiety is a terminal alkyne moiety. In some embodiments, a click chemistry reactive moiety is an aldehyde-containing group. In some embodiments, a click chemistry reactive moiety is a terminal hydrazine moiety. In some embodiments, a click chemistry reactive moiety is a terminal oxyamine moiety. In some embodiments, a click chemistry reactive moiety is an epoxide-containing group. In some embodiments, a click chemistry reactive moiety has a terminal maleimide moiety. One of skill in the relevant chemical and synthetic arts would appreciate that various other such click chemistry reactive moieties are known in the art and are contemplated for use in conjunction with methods of the present invention.

One such highly versatile click reaction, mentioned above, is the Huisgen cycloaddition (Huisgen, R. et al., 1960). As depicted below in Scheme X, the Huisgen cycloaddition involves the reaction of a dipolarophile with a 1,3-dipolar compound to afford a 5-membered (hetero) cycle.

Scheme X

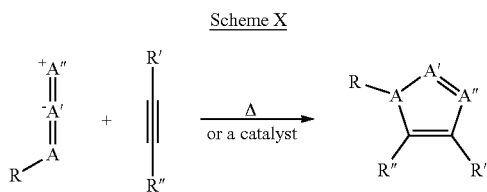

In some embodiments, such cycloadditions are catalyzed by Cu(I) salts, and are referred to as Copper(I)-catalyzed Azide-Alkyne Cycloaddition (CuAAC)) (Toraoe, C. W. et al., 2002; Rostovtsev, V. V. et al., 2002; Lewis, W. G. et al, 2002; Lewis, W. G. et al, 2002; Kolb, H. C. et al, 2001; and Iha, R. K. et al, 2009). Such copper-catalyzed azide-alkyne cycloadditions are exceptionally broad in scope (Rostovtsev, V. V.; et al. *Angew. Chem. Int. Ed.* 2002, 41, 2596-2599; Tornøe, C. W.; et al. *J. Org. Chem.* 2002, 67, 3057-3062). The use of Cu(I) catalysts accelerate the reaction by factors up to $10^7$ while preserving the inertness of both azides and alkynes toward the vast majority of functional groups and conditions (Rostovtsev, V. V.; et al. *Angew. Chem. Int. Ed.* 2002, 41, 2596-2599; Wang, Q.; et al. *J. Am. Chem. Soc.* 2003, 125, 3192-3193).

Copper-containing complexes which catalyze such reactions include, but are not limited to, copper bromide (CuBr), copper chloride (CuCl), copper sulfate ($CuSO_4$), copper iodide (CuI), $[Cu(MeCN)_4](OTf)$, and $[Cu(MeCN)_4](PF_6)$. Organic and inorganic metal-binding ligands can be used in conjunction with metal catalysts and include, but are not limited to, sodium ascorbate, tris(triazolyl)amine ligands, tris(carboxyethyl)phosphine (TCEP), and sulfonated bathophenanthroline ligands. Other such catalysts, for instance other copper catalysts or ruthenium- or silver-based catalysts, are known in the art, as are various methodologies for making and using the same.

In certain instances where click chemistry is particularly useful (e.g., in bioconjugation reactions), the presence of a metal catalyst (e.g., copper) can be detrimental. Accordingly, methods of performing certain cycloaddition reactions were developed without the use of metal catalysis. Such "metal free" click reactions utilize click chemistry reactive moieties which are activated in order to facilitate cycloaddition.

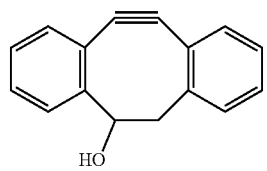 [SMILES: OC1Cc2ccccc2C#Cc2ccccc21]

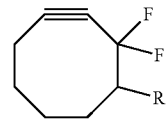

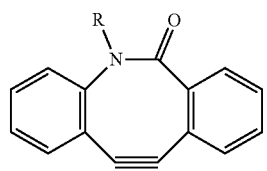

Exemplary such reactions are depicted in Scheme Y, below.

Scheme Y

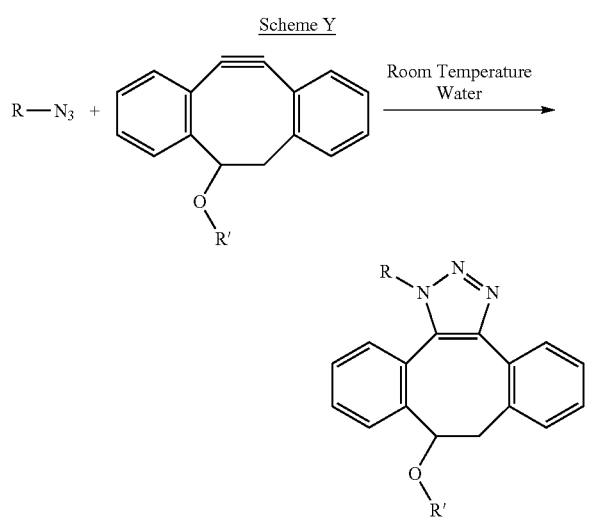

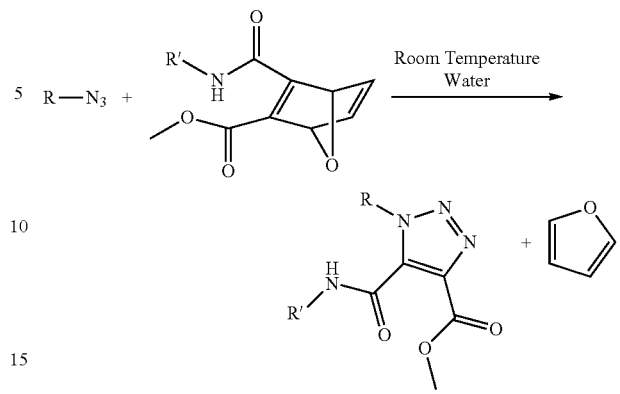

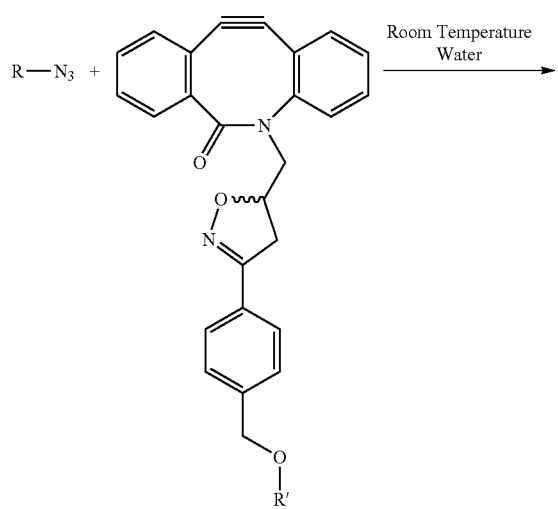

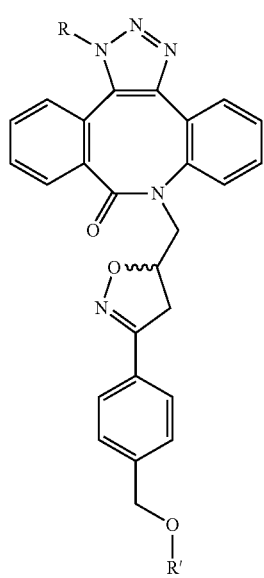

In some embodiments, association between a ligand entity and lipid entity occurs, at least in part, via one or more of the following: Diels-Alder chemistry (e.g., cyclopentadiene-dienophile reactions), Staudinger ligation, oxime/hydrazone formation, Quadricyclane ligation, tetrazine ligation, and/or isonitrile based click ligation. Additional methods of associating a ligand entity with a lipid entity may be found, inter alia, in Sletten and Bertozzi, Bioorthoganal Chemistry: Fishing for Selectivity in a Sea of Functionality, 2009, Angewandte Chemie International Edition, 48(38): 6974-6998.

A non-limiting exemplary association between a ligand entity and a lipid entity is depicted in FIG. 14.

As depicted in FIG. 14, the lipid entity (shown as a membrane anchor) and linker are attached via a covalent bond, shown as a dark circle. As shown in FIG. 14, "X" and "Y" may be bioorthogonal reaction partners that can react in water without interference by other partners, or may be standard amide, ester, thioester, thioether, disulfide, oxime or hydrazone bonds. In some embodiments, "X" and "Y" are click chemistry moieties. In some embodiments, the reaction may be catalyzed, for example, by an enzyme (e.g., N-terminal modification, *Angew. Chem. Int. Ed.* 2006, 45, 5307-5311; sortase mediated tagging: Popp, M. W.; Antos, J. M.; Grotenbreg, G. M.; Spooner, E.; Ploegh, H. L. *Nat. Chem. Biol.* 2007, 3, 707-708; phosphopantetheine transferase mediated tagging: Meier, J. L.; Mercer, A. C.; Rivera, H.; Burkart, M. D. *J. Am. Chem. Soc.* 2006, 128, 12174-12184; Biotin ligase: Chen, I.; Howarth, M.; Lin, W. Y.; Ting, A. Y. Nat. Meth. 2005, 2, 99-104. "SNAP-tag" and CLIP-tag" approaches: Gautier, A.; Juillrat, A.; Heinis, C.; Correa, I. R.; Kindermann, M.; Beaufils, F.; and Johnsson, K. Chem. Biol. 2008, 15, 128-136; Halotag approach: Los, G. V; Encell, L. P.; McDougall, M. G.; Hartzell, D. D.; Karassina, N.; Simprich, C.; Wood, M. G.; Learish. R.; Ohana, R. F.; Urh, M.; Simpson, D.; Mendez, J.; Zimmerman, K.; Otto, P.; Vidugiris, G.; Zhu, J.; Darzins, A.; Klaubert, D. H.; Bulleit, R. F.; Wood, K. V., *ACS Chem. Biol.* 2008, 3, 373-382).

Exemplary Agents

The following agents are provided to illustrate specific embodiments of the present invention and are not intended to be limiting:

1-Chem 149-157
s-Chem 149-157 (commercial source)
H₂N-Y-F-P-G-Q-F-A-F-S-COOH (SEQ ID NO.: 8)
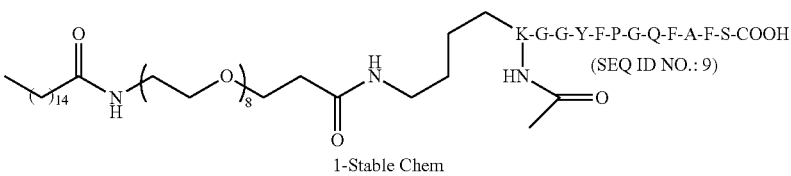
1-Stable Chem
s-Stable Chem
H₂N-Y-F-L-P-S-Q-F-A-Tic-S-COOH (SEQ ID NO.: 10)
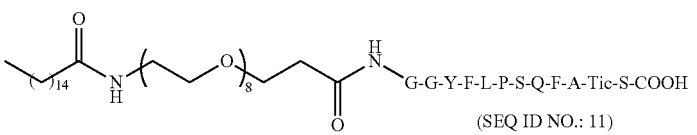
Ac₂-KGG-Chem9
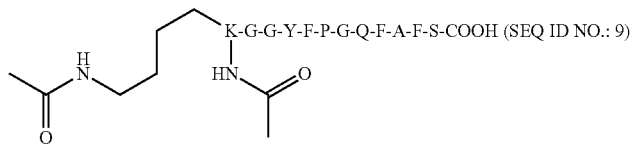
PA-PEG8-K(Ac)GG-Chem9
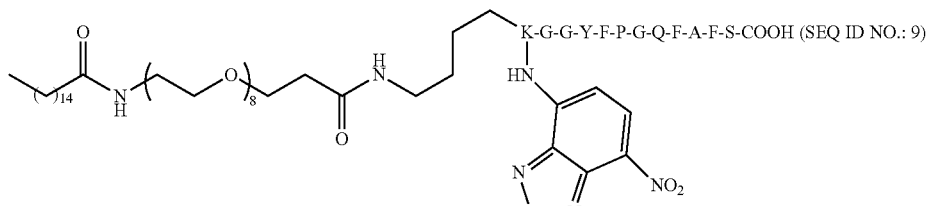
PA-PEG12-K(NBD)GG-Chem9
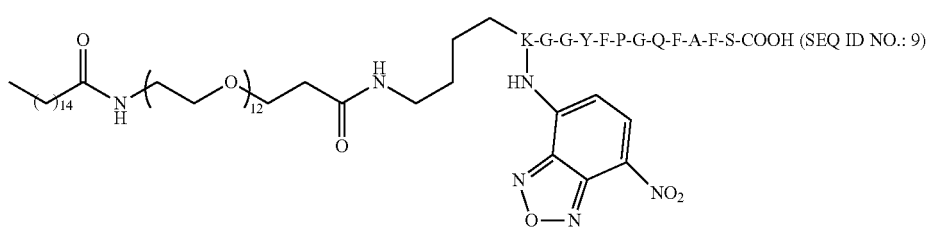
PEG8-stable-Chem9
Stearic Acid-PEG8-Chem9
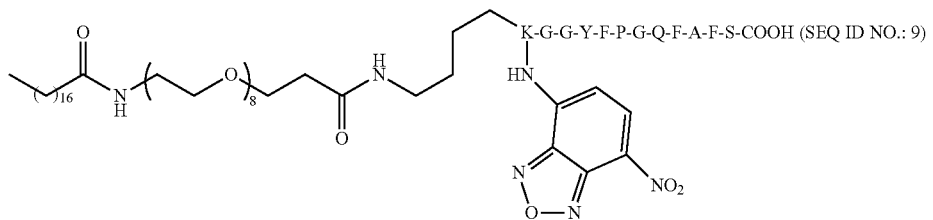
F6PA-PEG8-Chem9
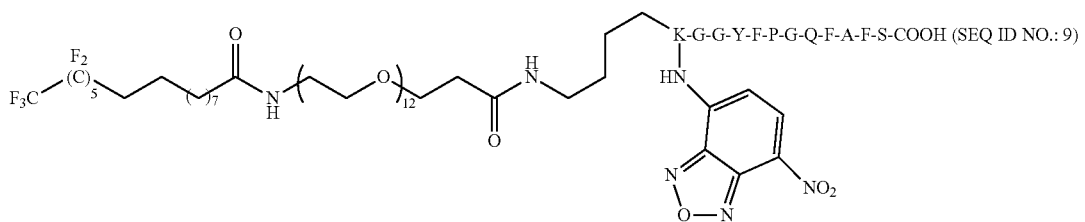

Oleic Acid-PEG8-Chem9

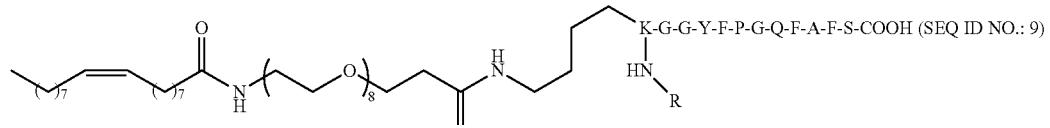

Eladic Acid-PEG8-Chem9

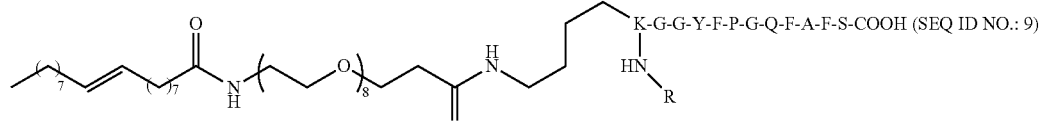

Cholesterol-PEG8-Chem9

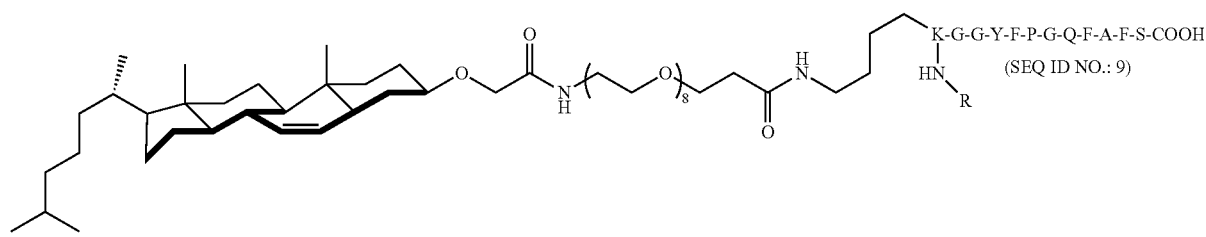

Identification and/or Characterization of Ligand Entity Activities

In some embodiments, the present invention provides methods of identifying and/or characterizing ligand entities with one or more previously unknown activities. In some embodiments, a previously unknown activity may be: a new target, a new binding site on a known target, and/or a new biological effect.

In some embodiments, provided methods allow for the identification and/or characterization of one or more previously unknown properties of one or more precursor polypeptides. In some embodiments, provided methods allow for characterization of precursor polypeptides and the biological function a precursor polypeptide may be capable of exerting on a target. In some embodiments, provided methods allow for the characterization of a previously unknown property of a precursor polypeptide, such as a new binding affinity or even new binding site.

In some embodiments, provided methods allow for the identification of ligands for a specific target that previously had no known ligands. In some embodiments, a library of candidate ligand entities may be generated and tested in a membrane tethered form as described herein.

According to various embodiments, any of a variety of target specific assays may be used to identify and/or characterize a ligand entity, including luciferase based assays as described in Fortin et al., Discovery of Dual-Action Membrane-Anchored Modulators of Incretin Receptors, PLoS One 2011, 6; Harwood et al., Membrane Tethered Bursicon Constructs as Heterodimeric Modulators of the Drosophila G Protein-Coupled Receptor Rickets, Mol. Pharm., 2013, 83:814-821; and Fortin et al., Membrane-Tethered Ligands are Effective Probes for Exploring Class B1 G Protein-Coupled Receptor Function, Proc. Natl. Acad Sci., 2009, 106: 8049-8054, the disclosures of which are hereby incorporated by reference in their entirety. Candidate ligand entities that show one or more desired activities (e.g., agonist/antagonist activity, protease resistance), for example, as a portion of a membrane tethered ligand (MTL) may then be selected for development as soluble lipidated ligand agents as described herein.

Pharmaceutical Compositions

In some embodiments, the present invention provides pharmaceutical compositions comprising a provided soluble lipidated ligand agent together with one or more pharmaceutically acceptable excipients.

In some embodiments, provided pharmaceutical compositions may be prepared by any appropriate method, for example as known or hereafter developed in the art of pharmacology. In general, such preparatory methods include the step of bringing a provided soluble lipidated ligand agent into association with one or more pharmaceutically acceptable excipients, and then, if necessary and/or desirable, shaping and/or packaging the product into an appropriate form for administration, for example as or in a single- or multi-dose unit.

In some embodiments, compositions may be prepared, packaged, and/or sold in bulk, as a single unit dose, and/or as a plurality of single unit doses. As used herein, a "unit dose" is a discrete amount of the pharmaceutical composition comprising a predetermined amount of the provided soluble lipidated ligand agent. The amount of the provided soluble lipidated ligand agent is generally equal to the dosage of the soluble lipidated ligand agent alone which would be administered to a subject and/or a convenient fraction of such a dosage such as, for example, one-half or one-third of such a dosage.

In many embodiments, provided pharmaceutical compositions are specifically formulated for intravenous or subcutaneous delivery. In some embodiments, provided pharmaceutical compositions are specifically formulated for mucosal delivery (e.g., oral, nasal, rectal or sublingual delivery).

In some embodiments, appropriate excipients for use in provided pharmaceutical compositions may, for example, include one or more pharmaceutically acceptable solvents, dispersion media, granulating media, diluents, or other liquid vehicles, dispersion or suspension aids, surface active agents and/or emulsifiers, isotonic agents, thickening or emulsifying agents, preservatives, solid binders, lubricants, disintegrating agents, binding agents, preservatives, buffering agents and the like, as suited to the particular dosage form desired. Alternatively or additionally, pharmaceutically acceptable excipients such as cocoa butter and/or suppository waxes, coloring agents, coating agents, sweetening, flavoring, and/or perfuming agents can be utilized. Remington's *The Science and Practice of Pharmacy*, 21$^{st}$ Edition, A. R. Gennaro (Lippincott, Williams & Wilkins, Baltimore, Md., 2005; incorporated herein by reference) discloses various excipients used in formulating pharmaceutical compositions and known techniques for the preparation thereof.

In some embodiments, an appropriate excipient is at least 95%, at least 96%, at least 97%, at least 98%, at least 99%, or 100% pure. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or other International Pharmacopoeia.

In some embodiments, liquid dosage forms (e.g., for oral and/or parenteral administration) include, but are not limited to, emulsions, microemulsions, solutions, suspensions, syrups, and/or elixirs. In addition to provided soluble lipidated ligand agents, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such a CREMOPHOR®, alcohols, oils, modified oils, glycols, polysorbates, cyclodextrins, polymers, and/or combinations thereof.

In some embodiments, injectable preparations, for example, sterile aqueous or oleaginous suspensions, may be formulated according to known methods using suitable dispersing agents, wetting agents, and/or suspending agents. Sterile liquid preparations may be, for example, solutions, suspensions, and/or emulsions in nontoxic parenterally acceptable diluents and/or solvents, for example, as a solution in 1,3-butanediol. Among the acceptable vehicles and solvents that may be employed, for example, are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of liquid formulations.

Liquid formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In some embodiments, one or more strategies may be utilized prolong and/or delay the effect of a provided soluble lipidated ligand agent after delivery.

In some embodiments, provided pharmaceutical compositions may be formulated as suppositories, for example for rectal or vaginal delivery. In some embodiments, suppository formulations can be prepared by mixing utilizing suitable non-irritating excipients such as cocoa butter, polyethylene glycol or a suppository wax which are solid at ambient temperature but liquid at body temperature and therefore melt in the body (e.g., in the rectum or vaginal cavity) and release the provided soluble lipidated ligand agent(s).

In some embodiments, solid dosage forms (e.g., for oral administration) include capsules, tablets, pills, powders, and/or granules. In such solid dosage forms, the provided soluble lipidated ligand agent(s) may be mixed with at least one inert, pharmaceutically acceptable excipient such as sodium citrate or dicalcium phosphate and/or fillers or extenders (e.g., starches such as maize starch, wheat starch, rice starch, potato starch; sugars such as lactose, sucrose, glucose, mannitol, sorbitol, and silicic acid), binders (e.g., carboxymethylcellulose, alginates, gelatin, polyvinylpyrrolidinone, sucrose, and acacia), humectants (e.g., glycerol), disintegrating agents (e.g., agar, Explotab, sodium starch glycolate, Amberlite, sodium carboxymethylcellulose, ultramylopectin, orange peel, natural sponge, bentonite, calcium carbonate, potato starch, tapioca starch, alginic acid, certain silicates, one or more insoluble cationic exchange resins, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

In some embodiments, solid compositions of a similar type may be employed as fillers in soft and/or hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

Exemplary enteric coatings include, but are not limited to, one or more of the following: cellulose acetate phthalate; methyl acrylate-methacrylic acid copolymers; cellulose acetate succinate; hydroxy propyl methyl cellulose phthalate; hydroxy propyl methyl cellulose acetate succinate (hypromellose acetate succinate); HP55; polyvinyl acetate phthalate (PVAP); Eudragit L30D; Eudragit L; Eudragit S; Aquateric; methyl methacrylate-methacrylic acid copolymers; methacrylic acid copolymers, cellulose acetate (and its succinate and phthalate version); styrol maleic acid copolymers; polymethacrylic acid/acrylic acid copolymer; hydroxyethyl ethyl cellulose phthalate; hydroxypropyl methyl cellulose acetate succinate; cellulose acetate tetrahydrophtalate; acrylic resin; shellac, and combinations thereof. In some embodiments, an enteric coating is substantially impermeable to at least pH 5.0.

In some embodiments, solid dosage forms may optionally comprise opacifying agents and can be of a composition that they release the provided soluble lipidated ligand agent(s) only, or preferentially, in a certain part of the intestinal tract (e.g., the duodenum, the jejunum, or the ileum), optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

In some embodiments, the present invention provides compositions for topical and/or transdermal delivery, e.g., as a cream, liniment, ointment, oil, foam, spray, lotion, liquid, powder, thickening lotion, or gel. Particular exemplary such formulations may be prepared, for example, as products such as skin softeners, nutritional lotion type emulsions, cleansing lotions, cleansing creams, skin milks, emollient lotions, massage creams, emollient creams, make-up bases, lipsticks, facial packs or facial gels, cleaner formulations such as shampoos, rinses, body cleansers, hair-tonics, or soaps, or dermatological compositions such as lotions, ointments, gels, creams, liniments, patches, deodorants, or sprays.

In some embodiments, an adjuvant is provided in the same formulation with provided soluble lipidated ligand agent(s) so that adjuvant and provided soluble lipidated ligand agent(s) are delivered substantially simultaneously to the individual. In some embodiments, an adjuvant is provided in a separate formulation. Separate adjuvant may be administered prior to, simultaneously with, or subsequent to provided soluble lipidated ligand agent administration.

In some embodiments, provided compositions are stable for extended periods of time, such as 1 week, 2 weeks, 1 month, 2 months, 6 months, 1 year, 2 years, 3 years, or more. In some embodiments, provided compositions are easily transportable and may even be sent via traditional courier or other package delivery service. Accordingly, some embodiments may be useful in situations of disease outbreak, such as epidemics, or attacks with biological agents (e.g. anthrax, smallpox, viral hemorrhagic fevers, plague, and others) at least in part due to their ability to be stored for long periods of time and transported quickly, easily, and safely. Such attributes may allow for rapid distribution of provided compositions to those in need.

In some embodiments, it may be advantageous to release encapsulated agent and/or composition comprising such agent(s), for example, an antigen, at various locations along a subject's gastrointestinal (GI) tract. In some embodiments, it may be advantageous to release encapsulated agent, for example, an antigen, in a subject's mouth as well as one or more locations along the subject's GI tract. Accordingly, in some embodiments, a plurality of provided compositions (e.g., two or more) may be administered to a single subject to facilitate release of encapsulated agent at multiple locations. In some embodiments, each of the plurality of compositions has a different release profile, such as provided by various enteric coatings, for example. In some embodiments, each of the plurality of compositions has a similar release profile.

In some embodiments, colorants and flavoring agents may all be included. For example, provided agents and/or compositions comprising such agents may be formulated (such as by liposome or microsphere encapsulation) and then further contained within an edible product, such as a refrigerated beverage containing colorants and flavoring agents.

In some embodiments, one may dilute or increase the volume of a therapeutic with an inert material. Such diluents could include carbohydrates, especially mannitol, α-lactose, anhydrous lactose, cellulose, sucrose, modified dextrans and starch. Certain inorganic salts maybe also be used as fillers including calcium triphosphate, magnesium carbonate and sodium chloride. Some commercially available diluents are Fast-Flo, Emdex, STA-Rx 1500, Emcompress and Avicell.

An anti-frictional agent maybe included in a formulation to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of a drug during formulation and to aid rearrangement during compression might be added. Such glidants may include starch, talc, pyrogenic silica and hydrated silico aluminate.

To aid dissolution of a therapeutic into an aqueous environment, a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. Push-fit capsules can contain active ingredients in admixture with filler such as lactose, binders such as starches, and/or lubricants such as talc or magnesium stearate and, optionally, stabilizers. In soft capsules, provided agents and/or compositions comprising such agents maybe dissolved or suspended in suitable liquids, such as fatty oils, liquid paraffin, or liquid polyethylene glycols. In addition, stabilizers maybe added. Microspheres formulated for oral administration may also be used. Such microspheres have been well defined in the art. All formulations for oral administration should be in dosages suitable for such administration.

For buccal administration, compositions may take the form of tablets or lozenges formulated in conventional manner.

For administration by inhalation, provided agents and/or compositions comprising such agents maybe conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit maybe determined by providing a valve to deliver a metered amount. Capsules and cartridges of e.g., gelatin for use in an inhaler or insufflator maybe formulated containing a powder mix of the compound and a suitable powder base such as lactose or starch.

Also contemplated herein is pulmonary delivery of provided agents and/or compositions comprising such agents. Such agents are delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med*3:206-212 (1989)(1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of an agent and/or composition comprising such agent(s). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified agents may also be prepared in different formulations depending on the type of chemical modification or the type of device employed.

Formulations suitable for use with a nebulizer, either jet or ultrasonic, will typically comprise a provided agent dissolved in water at a concentration of about 0.1 to 25 mg of biologically active compound of the invention per mL of solution. The formulation may also include a buffer and a simple sugar (e.g., for compound of the invention stabilization and regulation of osmotic pressure). Such a nebulizer formulation may also contain a surfactant, to reduce or prevent surface induced aggregation of provided agent(s) and/or compositions comprising such agents caused by atomization of the solution in forming the aerosol.

Formulations for use with a metered-dose inhaler device will generally comprise a finely divided powder containing the compound of the invention suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device in some embodiments will comprise a finely divided dry powder containing one or more provided agents or compositions comprising such agents and may also include a bulking agent, such as lactose, sorbitol, sucrose, or mannitol in amounts which facilitate dispersal of the powder from the device, e.g., 50 to 90% by weight of the formulation. The agent and/or composition may advantageously be prepared in particulate form with an average particle size of less than 10 micrometers (µm), most preferably 0.5 to 5 µm, for most effective delivery to the deep lung.

Nasal delivery of a pharmaceutical composition comprising one or more provided agents is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device may be a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

In some embodiments, when it is desirable to deliver provided agents and/or compositions comprising such agents systemically, they may be formulated for parenteral administration by injection, e.g., by bolus injection or continuous infusion. Formulations for injection maybe presented in unit dosage form, e.g., in ampoules or in multi-dose containers, with an added preservative. Such compositions may take such forms as suspensions, solutions or emulsions in oily or aqueous vehicles, and may contain formulatory agents such as suspending, stabilizing and/or dispersing agents.

Pharmaceutical formulations for parenteral administration may be or include aqueous solutions of provided agents for example, those as exemplified in Examples below, in water-soluble form. Alternatively or additionally, suspensions of such agents maybe prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, such a suspension may also contain suitable stabilizers or other additives which increase the solubility of the agents to allow for the preparation of highly concentrated solutions.

Alternatively or additionally, provided agents may be in powder form for constitution with a suitable vehicle, e.g., sterile pyrogen-free water, before use.

In addition or as an alternative to the formulations described above, provided agents and/or compositions comprising such agents maybe formulated as a depot preparation. Such long acting formulations maybe formulated with suitable polymeric or hydrophobic materials (for example as an emulsion in an acceptable oil) or ion exchange resins, or as sparingly soluble derivatives, for example, as a sparingly soluble salt.

Pharmaceutical compositions of provided agents and/or compositions comprising such agents also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms of provided agents and/or compositions comprising such agents are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

Provided agents and/or compositions comprising such agents and optionally other therapeutics maybe administered per se(neat) or in the form of a pharmaceutically acceptable composition, and furthermore may be utilized, in some embodiments, in the form of a salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

In some embodiments, provided agents and/or compositions comprising such agents maybe provided in particles. Particles as used in this context means nanoparticles or microparticles (or in some instances larger particles) which can consist in whole or in part of provided agent(s) and/or other therapeutic agent(s) as described herein. Such particles may contain the agent(s) and/or compositions in a core surrounded by a coating, including, but not limited to, an enteric coating. The agent(s) and/or compositions also maybe dispersed throughout the particles. The agent(s) and/or compositions also maybe adsorbed into the particles. The particles maybe of any order release kinetics, including zero-order release, first-order release, second-order release, delayed release, sustained release, immediate release, and any combination thereof, etc. The particle may include, in addition to the agent(s) and/or compositions, any of those materials routinely used in the art of pharmacy and medicine, including, but not limited to, erodible, nonerodible, biodegradable, or nonbiodegradable material or combinations thereof. The particles maybe microcapsules which comprise one or more provided agents in a solution or in a semi-solid state. The particles may be of virtually any shape.

According to various embodiments, both non-biodegradable and biodegradable polymeric materials can be used in the manufacture of particles for delivering provided agent(s) and/or compositions. Such polymers maybe natural or synthetic polymers. In many embodiments, a polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methylacrylate), poly(isopropylacrylate), poly(isobutylacrylate), and poly(octadecylacrylate).

In some embodiments, provided agents and/or compositions comprising such agents maybe contained in controlled release systems. The term "controlled release" in this context is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in this context in its conventional sense to refer to a drug formulation that provides for gradual release of a drug over an extended period of time, and that preferably, although not necessarily, results in substantially constant blood levels of a drug over an extended time period. The term "delayed release" is used in this context its conventional sense to refer to a drug formulation in which there is a time delay between administration of the formulation and the release of the drug there from. "Delayed release" may or may not involve gradual release of drug over an extended period of time, and thus may or may not be "sustained release."

In some embodiments, use of a long-term sustained release implant maybe particularly suitable for treatment of chronic conditions with one or more provided agents. "Long-term" release, as used in this context, means that an implant is constructed and arranged to deliver therapeutic levels of the active ingredient for at least 7 days, and preferably 30-60 days. Long-term sustained release implants are well-known to those of ordinary skill in the art and include some of the release systems described elsewhere herein.

Routes of Administration

In some embodiments, provided soluble lipidated ligand agents may be formulated for any appropriate route of delivery. In some embodiments, provided soluble lipidated ligand agents may be formulated for a route of delivery, including, but not limited to, intramuscular (IM), intravenous (IV), intraperitoneal (IP), subcutaneous (SQ), bronchial instillation, and/or inhalation; buccal, enteral, interdermal, intra-arterial (IA), intragastric (IG), intramedullary, intranasal, intrathecal, intratracheal instillation (by), intraventricular, intra-articular, mucosal, nasal spray, and/or aerosol, oral (PO), as an oral spray, rectal (PR), sublingual; topical and/or transdermal (e.g., by lotions, creams, liniments, ointments, powders, gels, drops, etc.), transdermal, vaginal, vitreal, and/or through a portal vein catheter; and/or combinations thereof. In some embodiments, the present invention provides methods of administration of provided soluble lipidated ligand agents via direct injection (e.g., into a tumor or specific tissue). In some embodiments, the present invention provides methods of administration of provided soluble lipidated ligand agents via intravenous administration. In some embodiments, the present invention provides methods of administration of provided soluble lipidated ligand agents via oral administration. In some embodiments, the present invention provides methods of administration of provided soluble lipidated ligand agents via subcutaneous administration.

In some embodiments, provided agents and compositions may be administered in a tissue specific manner (e.g., direct administration to a target tissue or organ). In some embodiments, a linker and/or ligand entity may comprise a localization sequence targeting an intracellular organelle (e.g., sequences targeting one or more of the peroxisome, nucleus, endoplasmic reticulum, golgi, and/or mitochondria). Exemplary localization sequences, and methods of their discovery and/or characterization, may be found, inter alia, in Pap et al., Peptide-based targeting of fluorophores to organelles in living cells, 2001, *Exp. Cell Res.*, 265: 288-293; and Chamberlain et al., Targeted delivery of Doxorubicin to mitochondria, 2013, *ACS Chem. Biol.*, 8: 1389-1395, the disclosures of which are hereby incorporated by reference in their entirety.

Dosing

Any of a variety of doses are contemplated as compatible with various embodiments. It is contemplated that a proper dose in a particular application will be determined in accordance with sound medical judgment. By choosing among various ligand entities and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat a particular subject. The effective amount for any particular application can vary depending on such factors as the disease or condition being treated, the particular compound of the invention being administered, the size of the subject, and/or the severity of the disease or condition.

In some embodiments, it is preferred that a maximum dose be used, that is, the highest safe dose according to sound medical judgment. Multiple doses per day are contemplated as useful in some embodiments to achieve appropriate systemic levels of a provided agent. Appropriate systemic levels may be determined by, for example, measurement of a subject's peak or sustained plasma level of the agent.

In some embodiments, daily oral doses of active compounds will be, for human subjects, from about 0.01 mg/kg per day to 1,000 mg/kg per day. Specific doses may be adjusted appropriately to achieve desired drug levels, local or systemic, depending upon the mode of administration. In some embodiments, multiple doses per day are contemplated to achieve appropriate systemic levels of agents. Provided agents may be formulated into a controlled and/or sustained release form.

In some embodiments, a ligand entity is or comprises is a drug approved by the FDA. In some embodiments, an FDA-approved ligand entity is used to form a soluble lipidated ligand agent. In some embodiments, such soluble lipidated ligand agents are administered according to the FDA-approved dosing regimen for the ligand entity. In some embodiments, such soluble lipidated ligand agents are administered according a dosing regimen that is different from the FDA-approved dosing regimen for the ligand entity. In some embodiments, such soluble lipidated ligand agents are administered at one or more of a lower dose, less frequent dosing schedule, and/or fewer total doses as compared to administration of the FDA-approved ligand entity alone.

Combination Therapy

In some embodiments, provided soluble lipidated ligand agents may be administered to a subject in combination with one or more other therapeutic agents or modalities, for example, useful in the treatment of one or more diseases, disorders, or conditions treated by the relevant provided pharmaceutical composition, so the subject is simultaneously exposed to both. In some embodiments, provided soluble lipidated ligand agent(s) are utilized in a pharmaceutical formulation that is separate from and distinct from the pharmaceutical formulation containing the other therapeutic agent. In some embodiments, provided soluble lipidated ligand agent(s) are admixed with the composition comprising the other therapeutic agent. In other words, in some embodiments, provided soluble lipidated ligand agent(s) are produced individually, and the provided soluble lipidated ligand agent is simply mixed with another composition comprising another therapeutic agent.

The particular combination of therapies (substances and/or procedures) to employ in a combination regimen will take into account compatibility of the desired substances and/or procedures and the desired therapeutic effect to be achieved. In some embodiments, provided soluble lipidated ligand agents can be administered concurrently with, prior to, or subsequent to, one or more other therapeutic agents.

It will be appreciated that the therapies employed may achieve a desired effect for the same disorder, or they may achieve different effects (e.g., each therapy treats a different symptom or aspect of the disorder). In some embodiments, provided soluble lipidated ligand agents are administered with a second therapeutic agent that is approved by the U.S. Food and Drug Administration (FDA).

As used herein, the terms "in combination with" and "in conjunction with" means that the provided soluble lipidated ligand agent can be administered concurrently with, prior to, or subsequent to, one or more other desired therapeutics. In general, each substance will be administered at a dose and/or on a time schedule determined for that agent.

Methods of Use

In some embodiments, provided soluble lipidated ligand agents may be used to treat one or more diseases, disorders, and/or conditions. In some embodiments, the present invention provides methods of treating a disease, disorder or condition including administering to a subject in need thereof a soluble lipidated ligand agent as described herein and/or a composition comprising such agents. In some embodiments, the agent(s) or composition(s) are administered at a dose and administration interval such that at least one symptom or feature of a disease, disorder, or condition is reduced in intensity, severity, duration, or frequency or has delayed onset.

Identifying and/or Characterizing Ligand, Linker, and/or Lipid Entities

In some embodiments, the present invention provides systems for identifying and/or characterizing potential components of soluble lipidated ligand agents as described herein.

In some particular embodiments, ligand entities of interest are identified and/or characterized in a membrane-anchored form. Indeed, as described herein, the present invention encompasses the surprising finding that a membrane-anchored format can reveal attributes of interest for the practice of the present invention. The present invention further surprisingly teaches, as demonstrated herein, that such attributes can be maintained when a relevant ligand entity is linked to a lipid entity.

According to some embodiments, the present invention provides systems that comprise and/or utilize an anchored ligand agents including a ligand entity that binds to a target, linked to an anchor entity (e.g., a membrane-spanning entity) that anchors the anchored ligand agent in the membrane. According to the present invention, such systems can be utilized to identify and/or characterize various features of interest attributable to the relevant ligand entity. In some embodiments, one or more features or characteristics of the anchored ligand agent is compared with that observed for the ligand entity in un-anchored format. In many such embodiments, the one or more features or characteristics are or include one or more features (e.g., affinity, avidity, residence time, etc) of binding to the relevant target.

In some embodiments, the present invention provides methods of selecting a ligand entity as a candidate ligand entity of interest for association with a lipid entity to form a soluble lipidated ligand entity if the anchored ligand entity's shows a relevant binding characteristic that is significantly different from that of the ligand entity alone. In some embodiments, a significantly different binding affinity, potency, and/or efficacy and/or half-life is or comprises a significantly increased binding affinity, potency, and/or efficacy and/or half-life as compared to that of the ligand entity. In some embodiments, a significantly different binding affinity potency, and/or efficacy and/or half-life is significantly decreased binding affinity, potency, and/or efficacy and/or half-life as compared to that of the ligand entity alone. In some embodiments, a ligand entity may be selected as a candidate ligand entity of interest if one or more of the binding affinity, potency, and/or efficacy and/or half-life is greater than the ligand entity alone by 10%, 20%, 30%, 40%, 50% or more. In some embodiments, a ligand entity may be selected as a candidate ligand entity of interest if one or more of the binding affinity, potency, and/or efficacy and/or half-life is less than the ligand entity alone by 10%, 20%, 30%, 40%, 50% or more. In some embodiments, the present invention provides methods of selecting a ligand entity as a candidate ligand entity of interest for association with a lipid entity to form a soluble lipidated ligand entity if the anchored ligand entity shows any significant level of activity.

In some embodiments, an anchored ligand agent may be or comprise a membrane-tethered ligand (MTL). The use of membrane tethered ligands (MTLs) has been described as useful in characterizing a particular ligand's interaction with a receptor (see Fortin et al., Membrane-tethered ligands are effective probes for exploring class B1 G protein-coupled receptor function, 2009, PNAS 106(19): 8049-8054). In some embodiments, anchored ligand agents may comprise a ligand entity, an anchor entity and, optionally, a linker and/or tag (e.g., an epitope tag). In some embodiments, one or more of the components of a particular anchored ligand agent comprise cDNA that is introduced into an in vitro or in vivo system for translation and characterization (see Fortin et al., entire reference).

In some embodiments, anchored ligand agents enable characterization of tissue-specific activation or blockade of selected receptors while minimizing or avoiding confounding off-target effects. It is contemplated that, in some embodiments, altering construct efficacy and/or the degree of membrane adherence, long term physiological consequences of receptor activation or blockade at titrated levels can be investigated (low level vs. high level stimulation).

Further, in some embodiments, the introduction of point mutations may convert tethered ligands between those that are agonist and antagonist, and capable of inducing or not inducing receptor internalization. In some embodiments, membrane-tethered peptides hold promise as biased ligands—that is, triggering one pathway (e.g., G protein mediated signaling) without activating another (e.g., ERK phosphorylation).

In accordance with various embodiments, anchored ligand agents (e.g., MTLs) offer an expedited approach for generating and assaying variant ligand entities (e.g., peptides), thus enabling identification of functionally optimized constructs. In some embodiments, these constructs may serve as the basis for efficient construction of their soluble counterparts, soluble lipidated ligand agents.

According to various embodiments, any ligand entity as described herein may be used with an anchor entity to characterize the ligand entity. Ligand entities (e.g., peptides) included in anchored ligand agents can be deliberately and specifically oriented, truncated, extended, mutated, and chemically modified and then readily characterized in terms of their activity with respect to their target receptor or receptors. For example, peptidic ligand entities maybe oriented so that it is linked to the anchor entity via its amino (N) terminal end; alternatively or additionally, a peptidic ligand entity can be oriented so that it is linked to the anchor entity via its carboxy (C) terminal end. In some embodiments, a peptidic ligand entity can be truncated by one or more amino acid residues at either end or both ends. In some embodiments, a peptidic ligand entity can be extended by one or more amino acid residues at either end, or both ends. Moreover, in some embodiments, a peptidic ligand entity can be truncated by one or more amino acid residues at one end and extended by one or more amino acid residues at the other end. Alternatively or additionally, one or more amino acid residues can be replaced by one or more different amino acid residues, at any position along the peptide. Substituted amino acid residues can include naturally occurring amino acid residues, non-naturally occurring amino acid residues, or amino acid residue analogs. Furthermore, amino acid residues can be chemically modified, for example, by covalently linking a chemical substituent, such as a sugar, to the amino acid residue. Generally, each of these types of variations can be accomplished using methods and techniques well established in the fields of molecular biology and nucleic acid and peptide chemistry.

Thus, in some embodiments, generation and characterization of anchored ligand agents may be used to generate functionally diverse membrane-tethered ligand entities including partial agonists and antagonists. In some embodiments, this first step encompasses generating a cDNA encoding a functionally active anchored ligand agent (see Fortin et al., entire reference). Variables to be considered for optimization of anchored ligand agents include orientation of the ligand entity (e.g., free amino or carboxy terminus for peptidic ligand entities), nature of the anchor entity, linker length and composition if a linker is present, and the presence of an epitope tag, if desired, and the position thereof. In some embodiments, luciferase-based reporter gene assays may be used to enable rapid screening to find functionally diverse anchored ligand entities (e.g., partial agonists, antagonists).

One important limitation of anchored ligand agents is that they are generally recombinant proteins which require expression of the corresponding cDNA. To enable direct administration of anchored peptides in vivo, a soluble lipidated ligand agent is typically generated for a corresponding optimized anchored ligand agent. However, the generation of anchored ligand entities provides an expedited approach for generating and assaying variant ligand entities, thus facilitating identification of functionally optimized ligand entities and/or constructs. These functionally optimized anchored ligand agents may then serve as the basis for efficient construction of soluble lipidated ligand agents as herein described.

Those of skill in the art will recognize a variety of assays and other measures that are useful in testing and/or characterizing particular embodiments. In order to provide some specific examples that illustrate the principles of the present invention, several non-limiting exemplary assays are described below.

In some embodiments, particularly where a ligand entity targets a membrane-associated ion channel, one or more of the following assays may be used to test and/or characterize a membrane tethered or soluble lipidated form of the ligand entity: fluorescence-based assays such as assays incorporating voltage sensitive dyes (e.g., N-[6-Chloro-7-hydroxycoumarin-3-carbonyl)-dimyristoylphosphatidylethanolamine], or bis-[1,3-dithiobarbituric acid] trimethine oxonol); ion flux-based assays (including those that measure the flux of physiological ions such as calcium, sodium, etc and those that measure the flux of surrogate ions such as thallium, cobalt, and iodide); and automated electrophysiology assays.

In some embodiments, particularly where a ligand entity targets a membrane-associated enzyme and/or enzyme-linked receptor, one or more of the following assays may be used to test and/or characterize a membrane tethered or soluble lipidated form of the ligand entity: initial rate assays (e.g., wherein an enzyme ligand entity is mixed with a large excess of substrate and the reaction rate is measured over a short period of time); progress curve assays, transient kinetics assays, relaxation assays (e.g., wherein an equilibrium mixture of ligand entity, substrate, and product is perturbed, for example, by a temperature, pressure, or pH jump and the return to equilibrium is measured); spectrophotometric assays (including certain colorimetric assays, as well as both direct and coupled assays); calorimetric assays; chemiluminescent assays; light scattering assays; microscale thermophoretic assays; radiometric assays; and chromatographic assays.

In some embodiments, particularly where a ligand entity targets one of more GPCRs, one or more of the following assays may be used to test and/or characterize a membrane tethered or soluble lipidated form of the ligand entity: resonance energy transfer-based assays including bioluminescence resonance energy transfer (BRET)-based assays. Radioligand binding assays, second messenger assays (e.g., such as a Gα, GTPγS, cAMP, and/or calcium assay); receptor de-sensitization assays (e.g., β-arrestin assays); and/or internalization assays. Exemplary specific assays may be found, inter alia, in Zimmerman et al., Differential b-Arrestin-Dependent Conformational Signaling and Cellular Responses Revealed by Angiotensin Analogs, 2012, *Sci Signal*, 5(221):ra33; Stallaert et al, Impedance Responses Reveal b2-Adrenergic Receptor Signaling Pluridimensionality and Allow Classification of Ligands with Distinct Signaling Profiles, 2012, *PLoS One*, 7(1):e29420.

Additional assays that may be desirable in testing and/or characterizing a tethered or soluble lipidated ligand entity may be found in, inter alia, Roth, B L, Assay Protocol Book, University of North Carolina at Chapel Hill National Institute of Mental Health Psychoactive Drug Screening Program, National Institute of Mental Health Psychoactive Drug Screening Program, 2009, S1.1-S1.135, available at pdsp.med.unc.edu/UNC-CH%20Protocol%20Book.pdf.

Activating Ligand Entities

In some embodiments, the present invention provides systems for activating a ligand entity including providing at least one ligand entity and associating at least one lipid entity with the at least one ligand entity, wherein associating the at least one ligand entity with the at least one lipid entity activates the at least one ligand entity.

It is contemplated that activation of a ligand entity can take any of several forms, depending upon the specific application for which a particular ligand entity is to be used. In general, one of skill in the art will recognize what activation of a ligand entity means a particular context. In some embodiments, activating the at least one ligand entity is characterized in that the potency of the at least one activated ligand entity is increased or decreased relative to the potency of the ligand entity alone. In some embodiments, activating the at least one ligand entity is characterized in that the at least one activated ligand entity has increased or decreased protease resistance relative to the ligand entity alone. In some embodiments, activating the at least one ligand entity is characterized in that the at least one activated ligand entity has increased or decreased binding affinity relative to the ligand entity alone. In some embodiments, activating the at least one ligand entity is characterized in that the at least one activated ligand entity has increased or decreased efficacy relative to the ligand entity alone. In some embodiments, activating the at least one ligand entity is characterized in that the diffusion of the activated ligand entity is less than the diffusion of the ligand entity alone. In some embodiments, activating the at least one ligand entity is characterized in that the at least one activated ligand entity has an increased effect on the basal activity of a target relative to the ligand entity alone. In some embodiments, activating the at least one ligand entity is characterized in that the at least one activated ligand entity has increased wash resistance relative to the ligand entity alone. In some embodiments, activating the at least one ligand entity is characterized in that the at least one activated ligand entity has increased half-life relative to the ligand entity alone. In some embodiments, activating the at least one ligand entity is characterized in that the at least one activated ligand entity has decreased half-life relative to the ligand entity alone. In some embodiments, activation of a ligand entity is characterized in that activation of a ligand entity results in two or more of: increased potency, increased protease resistance, increased effect on the basal activity of a target, wash resistance, increased or decreased half-life, and decreased diffusion of the activated ligand entity as compared to the ligand entity alone.

Unless otherwise stated, all publications, patents, and patent applications mentioned herein are hereby incorporated by reference in their entirety as if each individual publication, patent, or patent application was specifically and individually indicated to be incorporated by reference. In case of a conflict, the present application, including any definitions herein, will control.

EXAMPLES

Experimental Procedures for Examples 1-6

Unless otherwise specified, methods and reagents used in Examples 1-6, which specifically exemplify production and/or characterization of certain inventive soluble lipidated ligand agents are presented below. The particular soluble lipidated ligand agents addressed in Examples 1-6 target G-protein coupled receptors (GPCRs), and specifically the chemerin receptor (CMKLR1).

Recombinant GPCR and Tethered Ligand Constructs

Plasmids encoding either the human (University of Missouri cDNA Resource Center) or the mouse (Origene) chemerin receptor cDNA were purchased and subcloned into pcDNA1.1. Full length human chemerin cDNA (encoding pre-prochemerin corresponding to amino acids 1-163) was purchased from Sino Biological. The chemerin coding region was PCR amplified and subcloned into a type II membrane-tethered ligand (MTL) backbone as previously described. The corresponding MTL cDNA encodes a TNFα transmembrane domain, a 'GN' repeat linker containing a c-Myc tag (to monitor MTL expression levels), and the chemerin peptide at the C-terminus. The TNF-α transmembrane domain, by virtue of it being a type II transmembrane domain (TMD), positions the MTL such that the C-terminus of the construct projects into the extracellular space. This orientation is optimal for the study of chemerin since the C-terminal end of the peptide has been shown to be important for activity at CMKLR1. MTLs encoding pre-prochemerin (amino acids 1-163), full length chemerin (amino acids 21-157), and the C-terminal 9 amino acids of chemerin (149-157) were generated in addition to a negative control MTL (including the amino acid sequence of human galanin). To assess variant chemerin sequences, degenerate oligonucleotides ('NNKNNK') were used to introduce variability at positions corresponding to the 2 carboxy terminal residues of chemerin 149-157 (amino acids 156 and 157). The nucleotide sequences of all receptor and tether constructs were confirmed using automated DNA sequencing followed by analysis with VectorNTI (Invitrogen).

Peptide Synthesis and Lipidation

All commercial reagents were used without further purification. N-tert-butoxycarbonyl (N-Boc) protected D- and L-amino acids, and 4-hydroxymethylphenylacetamidomethyl (PAM) resin modified with N-Boc-L-Ser (Boc-L-Ser-PAM) were purchased from Chemimpex. HBTU (2-(1H-benzotriazol-1-yl)-1,1,3,3-tetramethyluronium hexafluorophosphate) was procured from Novabiochem. Monodisperse, hetero-bifunctional polyethylene glycol (PEG), N-Fmoc-PEG8-propionic acid and the unnatural amino acid Boc-(3S)-1,2,3,4-Tetrahydroisoquinoline-3-carboxylic acid (N-Boc-L-Tic-OH) were from AAPPTec. Palmitic acid was purchased from Sigma Aldrich. Hydrogen fluoride was from Matheson Tri-Gas. Solvents for reversed-phase high performance liquid chromatography (RP-HPLC) had the following composition: Solvent A, $H_2O/CH_3CN/$ Trifluoroacetic acid (TFA) (99/1/0.1); Solvent B, $CH_3CN/ H_2O/TFA$ (90/10/0.07).

Peptides were manually assembled using the in-situ neutralization protocol for t-Boc chemistry (see Schnolzer M et al. (1992) Int J Peptide Protein Res 40(3-4):180-93) on PAM resin on a 0.5 mmol scale. Amino acids, both L and D were used with the following side chain protecting groups: Gln (Xan), Lys (Fmoc), Ser(Bzl) and Tyr(2-Br-Z). Peptide coupling reactions were carried out with a 4-fold excess (2.0 mmol) of activated amino acid for at least 15 min. The t-Boc protecting group on the N-terminus was removed using TFA. Both of the resins were split into two equal portions. One portion was used for synthesizing the non-lipidated peptides. The chemerin 9 peptide (s-Chem 149-157) on resin was acetylated at the N-terminus before cleavage; the stable chemerin peptide (s-Stable Chem) was left unmodified at the N-terminus. These peptides served as positive controls for the lipidated peptides. The free N-terminus was first pegylated with N-Fmoc-PEG8-propionic acid using standard HBTU coupling conditions. The N-Fmoc protecting group was removed by treatment with 10% piperidine in DMF (N,N-Dimethylformamide) for 5 m. Palmitic acid was subsequently coupled with the N-terminal free amine of the pegylated peptide. Peptides were cleaved from the resin by using high HF conditions (see Pennington, M. W., HF cleavage and deprotection procedures for peptides synthesized using a Boc/Bzl strategy, 1994, Methods in Mol. Biol., 35: 319-326) (90% anhydrous HF/10% anisole at 0° C. for 1.5 h) and precipitated with cold $Et_2O$. Unmodified peptides were extracted using 10% AcOH in water and the lipidated peptides were extracted using 10% AcOH in water followed by 10% AcOH in 50% $EtOH/H_2O$. Crude peptides were purified by RP-HPLC [Vydac C18, 10 μm, 22 mm×250 mm]. The purities of the peptides were assessed by analytical RP-HPLC [Vydac C18, 5 μm, 4 mm×250 mm]. The molar mass of peptides was determined by MALDI-TOF MS. Peptide concentrations were determined using tyrosine absorbance ($\varepsilon=1400$ $M_{-1} \cdot cm_{-1}$ at 278 nm) (see Gill, S C and Von Hippel, Calculation of protein extinction coefficients from amino acid sequence data, 1989, Analytical Biochem, 182: 319-326). The soluble control peptide for chemerin 9 (s-Chem 149-157) included a KGG spacer coupled to the N-terminus to allow attachment of the corresponding PEG8-palmitic acid and to provide a handle for further modification with fluorophores. In comparison, the soluble stable chemerin analog (s-Stable Chem) did not contain the GG spacer used for subsequent anchoring.

Cell Culture

Human embryonic kidney (HEK) 293 cells were cultured in Dulbecco's modified Eagle's medium (Life Technologies) with 10% fetal bovine serum (Atlanta Biologicals), 100 U/mL penicillin, and 100 μg/mL streptomycin. Cells were maintained at 37° C. in a humidified environment with 5% $CO_2$.

Luciferase Reporter Gene Assays

Receptor-mediated signaling was assessed as previously described. Briefly, HEK293 cells were plated at a density of 6,000 cells/well into 96-well clear-bottom plates and grown to ~80% confluence. Cells were transiently transfected with PEI (0.1 μL/well of a 1 mg/mL solution) in serum-free media with cDNAs encoding a) human or mouse chemerin receptor (or pcDNA1.1 as an empty expression vector), b) a tethered ligand (where applicable), c) an SRE-luciferase reporter gene with a PEST degradation sequence ($SRE_{5x}$-Luc-PEST), d) $G_{q5i66V}$, a chimeric $G\alpha_q$ protein containing the five carboxy-terminal amino acids corresponding to $G\alpha_i$ and valine substitution at amino acid position 66, and e) β-galactosidase (control for transfection efficiency). Expression of $G_{q5i66V}$ directs signaling of the $G\alpha_i$-coupled chemerin receptor to stimulation of a $G\alpha_q$-dependent $SRE_{5x}$-Luc-PEST reporter gene. For experiments investigating the agonist function of soluble and lipidated peptides, tethered ligand cDNA was not included in the transfection mixture. Twenty four hours after transfection, cells were stimulated with or without peptide agonist for 4 hours in serum-free medium. Ligands were synthesized as described above: recombinant human chemerin (corresponding to amino acids 21-157) was purchased from R+D systems and chemerin 145-157 was purchased from Phoenix Pharmaceuticals. Following ligand stimulation, the media was aspirated and luciferase activity measured using SteadyLite reagent and quantified using a TopCount NTX. A β-galactosidase assay was then performed following assessment of luminescence. Cleavage of 2-nitrophenyl β-D-galactopyranoside substrate was quantified after incubation of cell lysates at 37° C. for 30 to 60 minutes by measuring the optical density at 420 nm on a SpectraMax microplate reader. Luciferase reporter gene activities were normalized to corresponding β-galactosidase activity controls.

Washout Experiments

Agonist activity was compared with and without serial washings shortly after addition of ligand. Briefly, HEK293 cells were plated and transfected as described above with the addition of a poly-L-lysine plate pretreatment step to enhance cell adhesion. Twenty-four hours after transfection, cells were stimulated with increasing concentrations of agonist for 15 minutes at 37° C. Selected wells were washed three times with serum-free media. Plates were then incubated for an additional 4 hours. Receptor mediated signaling was assessed using a luciferase based assay as described above.

Ovalbumin Sensitization and In Vivo Chemerin Administration

Male FVB mice age 5-7 weeks (Charles River Laboratories) were housed under viral antibody-free conditions. Ovalbumin (OVA) sensitization and drug administration were performed as previously described with slight modifications. Briefly, mice were sensitized with intraperitoneal injection of 10 μg OVA (Grade III: Sigma) on days 0 and 7. On days 14, 15, 16, and 17, mice received a 25 minute aerosol challenge of 6% (wt/vol) OVA each day. On each of these days, 30 min prior to OVA challenge, mice were given 20 μL of lipidated stable chemerin (21 mM stock in DMSO diluted 1:100 in saline for a final concentration of 210 μM) by the intranasal route. Corresponding controls received DMSO diluted 1:100 in saline. On day 18 or 22, bronchoalveolar lavage fluid (BALF) was collected; animals were sacrificed for histological assessment. Mouse lungs were fixed in 10% (vol/vol) formalin and embedded in paraffin; tissue was stained with hematoxylin and eosin or periodic acid-Schiff reagent (Sigma). In another set of experiments, mice were treated with l-Stable Chem of DMSO control as described above. On day 18, lungs were fixed and stained with hematoxylin and eosin (H+E, Sigma). In a separate cohort of mice, bronchoalveolar lavage was performed with two 1 ml aliquots of phosphate-buffered saline (PBS) with 0.6 mM EDTA. Cells in BALF were resuspended in PBS and counted with a hemocytometer; cytospins were done via cytocentrifugation (265 g; StatSpin). Cells from the cytospin were stained with Wright-Giemsa stain (Sigma) for quantification of leukocyte subsets. At least 200 cells were counted per slide. Samples of cell-free BALF (centrifuged for 10 min at 2,000 g) were sent to Aushon Biosystems for cytokine measurements using bead arrays. For non-OVA control experiments, mice received l-Stable Chem (21 mM stock in DMSO diluted 1:100 in saline for a final concentration of 210 μM) or DMSO for 4 consecutive days (corresponding to days 14, 15, 16 and 17 of the OVA studies). On the 5$^{th}$ day (corresponding to day 18), mice were sacrificed and BALF collected and analyzed as described above.

Neuropathic Pain Model and Behavioral Analysis

Adult CD1 mice (male, 25-35 g) were used for behavioral studies. Mice were group-housed and kept under a 12-hour light/dark cycle. For the neuropathic pain model, chronic construction injury was induced by ligation of the sciatic nerve under isoflurane anesthesia (see Bennett and Xie, A peripheral mononeuropathy in rat that produces disorders of pain sensation like those seen in man, 1988, *Pain*, 33: 87-107). For intrathecal injection, spinal cord puncture was made with a 30 G needle between the L5 and L6 level to deliver reagents (10 μl) to the cerebral spinal fluid. L-Stable Chem was synthesized as described above. RvE1 was kindly provided by Resolvyx Pharmaceuticals Inc.

Nerve injury-induced mechanical allodynia and hypersensitivity were assessed by von Frey hairs as previously described (see Xu et al., Resolvin E1 inhibits neuropathic pain and spinal cord microglial activation following peripheral nerve injury, 2013, *J. Neuroimmune Pharmacol*, 8: 37-41). For testing mechanical sensitivity, the plantar surface of a hindpaw was stimulated with a series of von Frey hairs (0.02-2.56 grams, Stoelting). The 50% paw withdrawal threshold (PWT) was determined using Dixon's up-down method. For paw withdrawal frequency (PWF), the same von Frey hair (0.16 g) was applied 10 times and the number of positive responses to the stimulations counted. A positive response was scored if the mouse sharply withdrew the paw or flinched upon removal of the stimulus. Cold allodynia was tested by the acetone method as previously reported (see Flatters and Bennett, Ethosuximide reverses paclitaxel- and vincristine-induced painful peripheral neuropathy, 2004, *Pain*, 109:150-161). In brief, a drop of acetone was placed against the plantar paw of the mouse and the mouse's response monitored for the next 20 seconds. If there was no response then a score of 0 was assigned. If there was a response, this response was monitored 40 seconds in total and behavior was assigned as follows: 1, quick withdrawal or stamp of the foot; 2, prolonged withdrawal and repeated flicking of the paw; 3, repeated flicking of the paw with licking directed at the ventral side of the paw.

Data Analysis $EC_{50}$ values were determined by nonlinear curve fitting using Graph Pad Prism 6.0 software. Statistical comparisons were made using either t-test or one-way ANOVA with Tukey's posthoc test. Data were considered to be statistically significant with $p<0.05$.

Example 1: Soluble Full Length and C-Terminal Human Chemerin Peptides Activate Human and Mouse CMKLR1

MTLs can be generated with either an extracellular free amino or carboxy terminal end depending on the ligand activity determinants. Given the importance of the C-terminal end of chemerin, a type II transmembrane domain (TMD) anchor was incorporated into the chemerin MTL. This TMD configuration positions the C-terminal end of chemerin into the extracellular space, thus enabling interaction with its cognate GPCR, CMKLR1.

Figure 1:
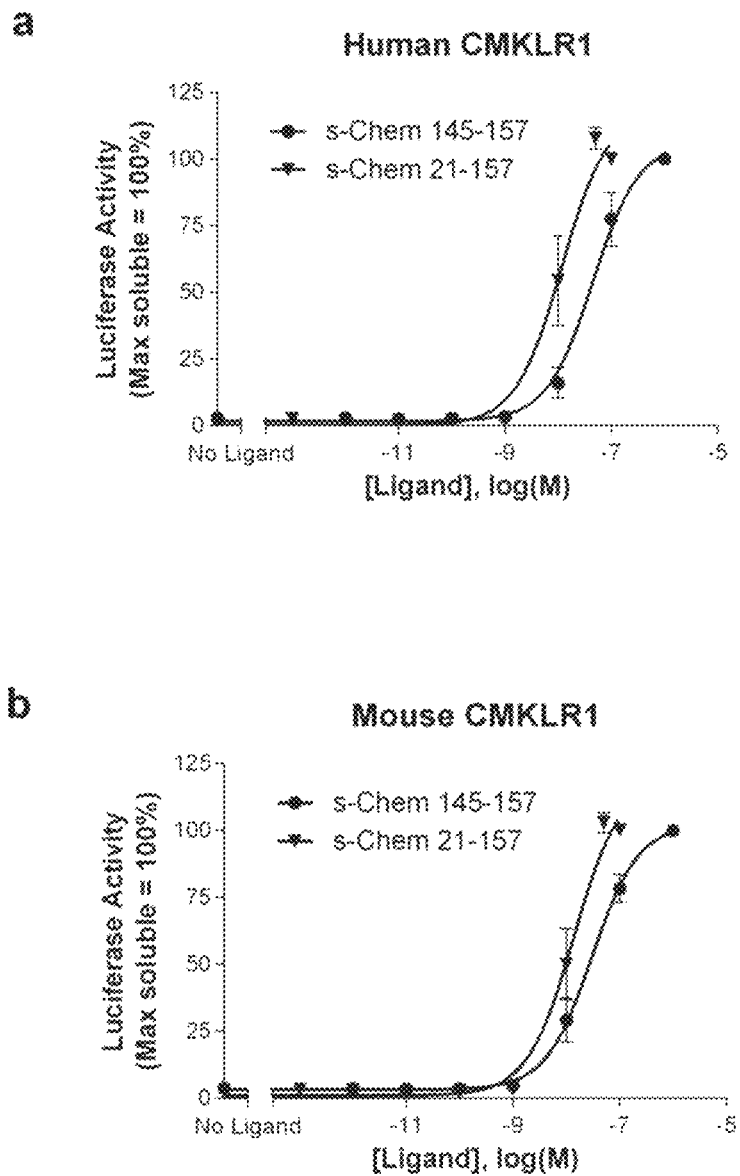
FIG. 1 shows exemplary graphs depicting the effects of soluble full length chemerin (s-Chem 21-157) and soluble chemerin 149-157 on both (A) human and (B) mouse CMKLR1. Data points represent the mean±S.E.M. from at least three independent experiments, each performed in triplicate.

In this Example, the activation of human and mouse CMKLR1 with full length (amino acids 21-157) and C-terminal (amino acids 149-157) chemerin peptides was first compared. HEK293 cells were transiently transfected with cDNAs encoding i) human or mouse CMKLR1, ii) a $SRE_{5x}$-Luc reporter gene, iii) a $G\alpha_{q5i66V}$ chimera, and iv) a β-galactosidase control. Twenty-four hours after transfection, cells were stimulated with ligand for 4 hours and luciferase activity determined as described in Experimental Procedures. Luciferase activity was normalized relative to the maximal value observed using saturating concentrations of the corresponding soluble ligand (=100%). Representative results are shown in FIG. 1. As illustrated in FIG. 1A, full length chemerin (s-Chem 21-157) activates human CMKLR1 with higher potency than the C-terminal 9 amino acid fragment (s-Chem 149-157). These two human peptides also activate mouse CMKLR1, again with s-Chem 21-157 potency exceeding that of s-Chem 149-157.

Figure 2:
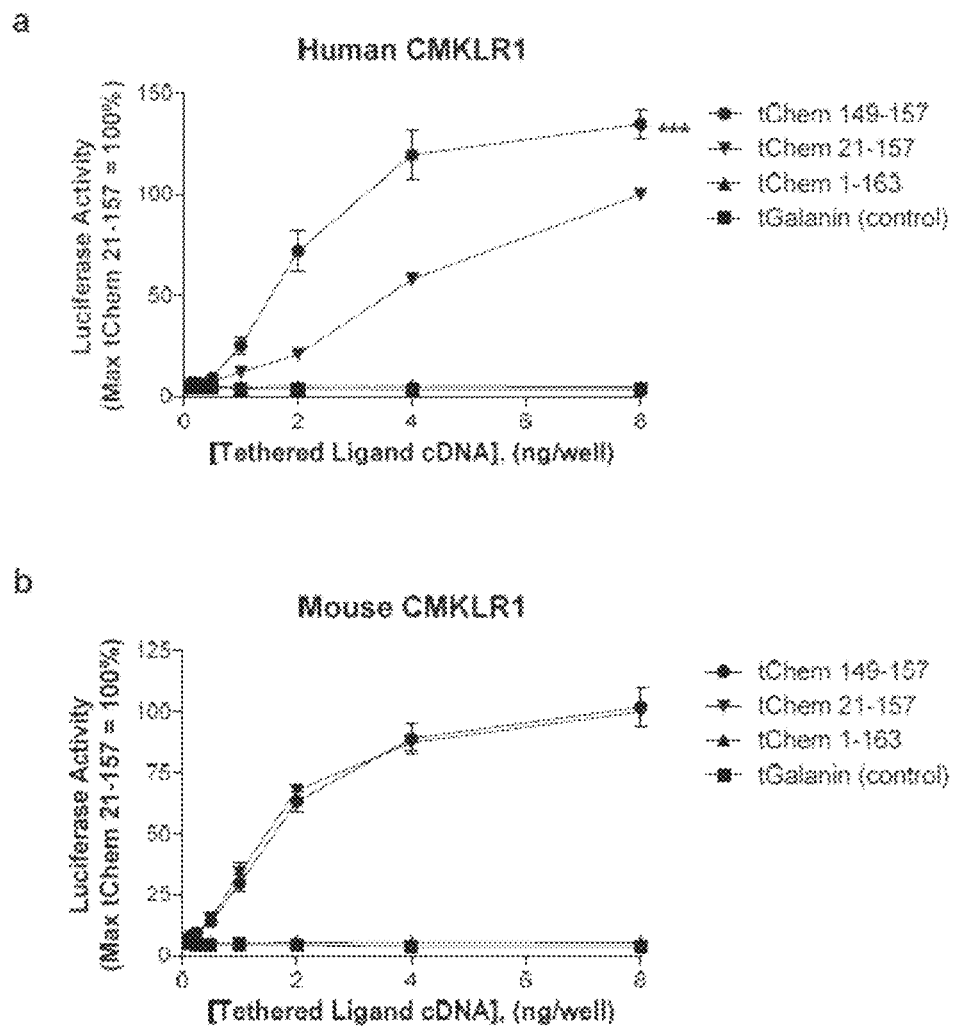
FIG. 2 shows a pair of exemplary graphs depicting the effects of tethered chemerin 9 (tChem 149-157) and full length chemerin (tChem 21-157) at the (A) human, and (B) mouse CMKLR1 receptors. Data points represent the mean±S.E.M. from at least three independent experiments, each performed in triplicate. Comparison of tChem 21-157 to tChem 149-157: ***$p<0.001$.

Example 2: Tethered Full Length and C-Terminal Human Chemerin Peptides Activate Both Human and Mouse Receptors As a next step, the effect of membrane anchoring on chemerin activity was examined. To pursue these studies, MTL constructs were made encoding the sequence of pre-prochemerin (amino acids 1-163), full length chemerin (amino acids 21-157), and C-terminal chemerin peptide (amino acids 149-157) and activity at both the human and mouse receptors was assessed. Pre-prochemerin (tChem 1-163) and the control (tGalanin) lack activity at both the human and mouse receptors. HEK293 cells were transiently transfected with cDNAs encoding i) various tethered ligands, ii) human or mouse CMKLR1, iii) a SRE5x-Luc reporter gene, iv) aGαq5i66V chimera, and v) a β-galactosidase control. Twenty-four hours after transfection, luciferase activity was determined as described in Experimental Procedures. Luciferase activity was normalized relative to the maximal value observed using tChem 21-157 cDNA (=100%). Representative results are shown in FIG. 2.

As with the corresponding soluble ligands, tethered full length chemerin (tChem 21-157) and the tethered C-terminal peptide (tChem 149-157) each activated both human (FIG. 2A) and mouse (FIG. 2B) CMKLR1. In contrast, tethered pre-prochemerin (tChem 1-163) did not activate either receptor, indicating that C-terminal processing is necessary for the activity of chemerin, as previously reported. In addition, a negative control tether encoding the sequence for human galanin did not activate either receptor, further illustrating specificity and selectivity of the tethered ligands.

Additional controls were performed to determine if the increased activity of tChem 149-157 could be explained by either differential expression of tethered constructs or a variable tendency of MTLs to trigger CMKLR1 internalization. Expression of both tethered constructs and the cognate receptors were assessed using an enzyme-linked immunosorbent assay (ELISA). The enhanced activity of tChem 149-157 was not an artifact of increased expression of tChem149-157 or the result of enhanced internalization of CMKLR1 (data not shown).

Figure 3:
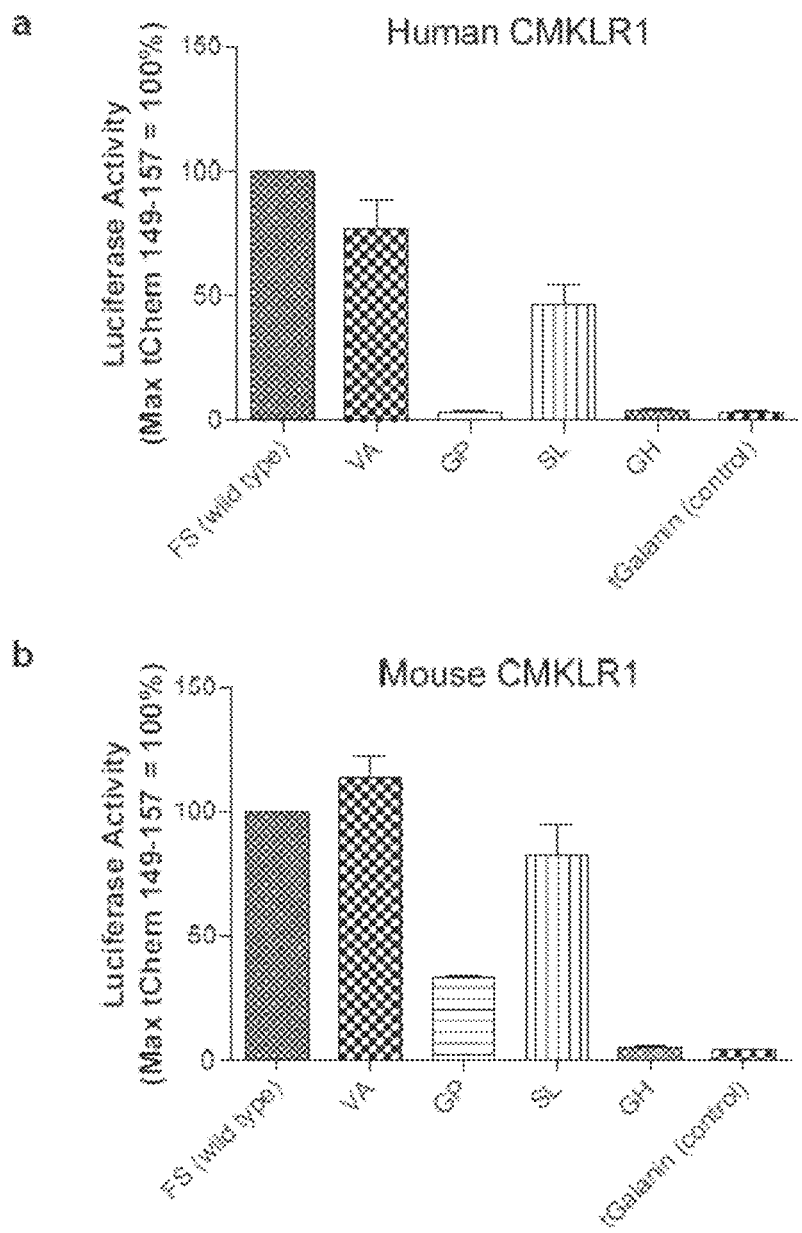
FIG. 3 shows a pair of exemplary graphs depicting the effects of modifying the two C-terminal amino acids of tChem 149-157 on the degree of activity on (A) human and (B) mouse CMKR1. Data points represent the mean±S.E.M. from at least three independent experiments, each performed in triplicate.

Example 3: The MTL Platform can be Used to Generate a Series of Chemerin Ligands with Varying Activities In light of the enhanced activity of tChem 149-157 at the human receptor, we next explored whether modification of the endogenous chemerin sequence could further potentiate ligand mediated signaling. To explain this possibility, 40 pools of 5-10 constructs encoding tChem 149-157 with variability at positions 156 and 157 were screened. Amino acids 156 and 157 were chosen since they are established CMKLR1 activity determinants. HEK293 cells were transiently transfected with cDNAs encoding i) 8 ng of various tethered ligands, ii) human or mouse CMKLR1, iii) a $SRE_{5x}$-Luc reporter gene, iv) a $G\alpha_{q5i66V}$ chimera, and v) a β-galactosidase control. Twenty-four hours after transfection, luciferase activity was determined as described in Experimental Procedures. Luciferase activity was normalized relative to the maximal value observed with tChem 149-157 cDNA (=100%). The most active pool was identified and used in follow-up experiments. Representative results are shown in FIG. 3.

As shown in FIG. 3A, the endogenous sequence (ending with phenylalanine-serine, 'FS') had comparable activity to 'VA' (sequence ending with valine-alanine) at human CMKLR1, while 'SL' (sequence ending with serine-leucine) showed partial agonist activity, and 'GP'/'GH' (sequences ending with glycine-proline and glycine histidine, respectively) exhibited no effect. In comparison, 'FS' and 'VA' both activated mouse CMKLR1 with both 'SL'/'GP' showing partial agonist activity and 'GH' showing no effect. Again, negative control tethered galanin did not activate either receptor. Since the endogenous Chem 149-157 sequence showed the highest activity as a tether, we chose to utilize this sequence in follow-up experiments.

Example 4: Lipidation of Chem 149-157 Confers Enhanced Potency and Wash-Resistant Activity Based on the results with tethered versus soluble chemerin 149-157, we hypothesized that the enhanced activity on human CMKLR1 was due to membrane anchoring. We thus postulated that a soluble lipidated ligand agent would also show increased activity and have the additional advantage that it could be directly delivered for in vivo testing. Accordingly, a lipidated counterpart of Chem 149-157 was synthesized. HEK293 cells were transiently transfected with cDNAs encoding i) human or mouse CMKLR1, ii) a $SRE_{5x}$-Luc reporter gene, iii) a $G\alpha_{q5i66V}$ chimera, and iv) a β-galactosidase control. Twenty-four hours after transfection, cells were stimulated with increasing concentrations of various ligands for 15 minutes. Selected wells were then washed three times with serum-free media and plates were further incubated for 4 hours. Luciferase activity, determined as described in Experimental Procedures, was normalized relative to the maximal value observed using saturating concentrations of s-Chem 149-157 in cells that were unwashed (=100%). Representative results are shown in FIG. 4.

Figure 4:
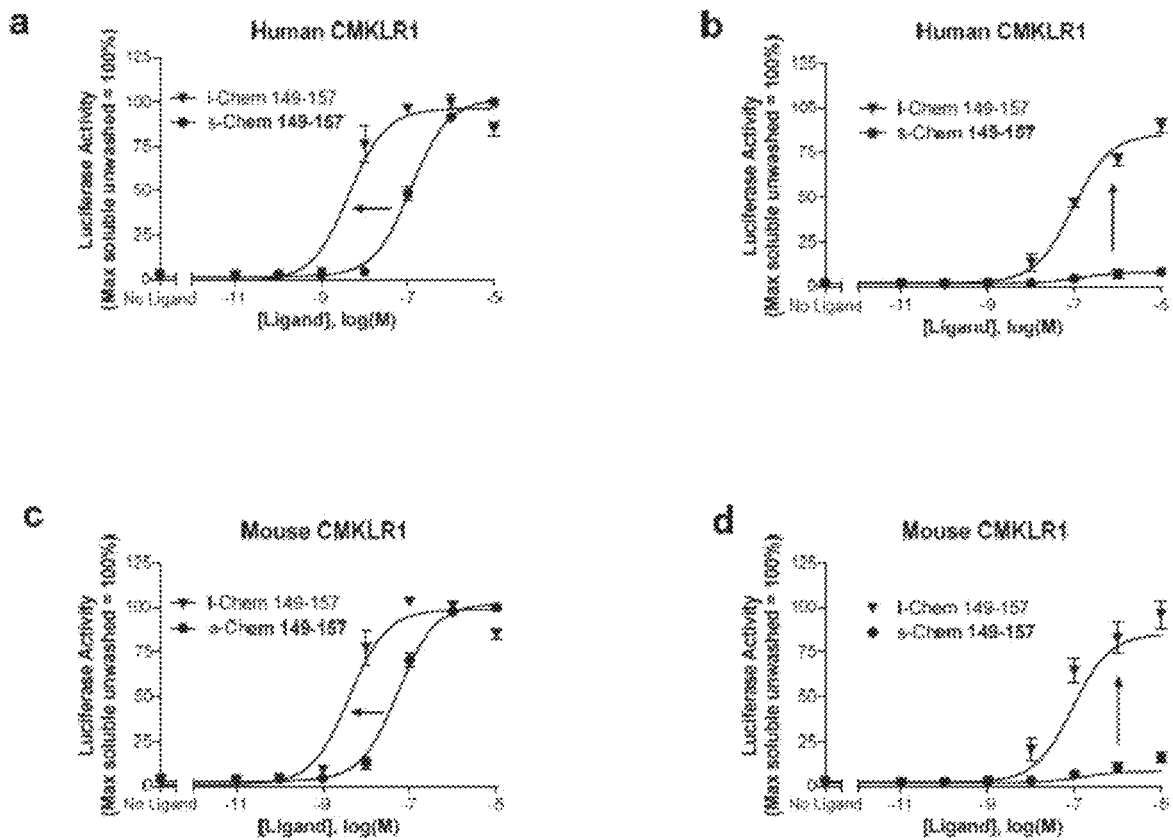
FIG. 4 shows a series of four exemplary graphs depicting the effect of lipidating chemerin 149-157 (l-Chem 149-157) on the potency of stimulation of (A) human and (C) mouse CMKLR1. Panels (B) and (D) show the effect of serial washing on the activity of the soluble peptide (s-Chem 149-157) as both ((B) human and (D) mouse CMKLR1.

As illustrated in FIG. 4, lipidation of the C-terminal 9 amino acids of chemerin (l-Chem 149-157) enhanced potency of the ligand at both the human (FIG. 4A) and mouse (FIG. 4C) CMKLR1 when compared to the soluble peptide (s-Chem 149-157). In addition to assessing potency, we were also interested in determining if the lipidated peptide would anchor in the cell membrane thus enhancing the duration of activity. To address this question we performed washout experiments on both human (FIG. 4B) and mouse (FIG. 4D) receptor. Despite serial washes after the addition of ligand, the activity of l-Chem 149-157 persisted, whereas only trace agonist-induced signaling was observed with the soluble ligand. Signaling by both s-Chem 149-157 and l-Chem 149-157 required expression of CMKLR1; no agonist activity was observed when cells were transfected with vector control (i.e., pcDNA1.1).

Example 5: A Lipidated, Stable Chemerin Analog Activates Human and Mouse CMKLR1 with High Potency and Wash Resistance It has been previously shown that chemerin is rapidly inactivated in vivo by proteases. To further enhance the activity and half-life of the lipidated chemerin analog, we substituted a proteolysis-resistant chemerin sequence into our construct. HEK293 cells were transiently transfected with cDNAs encoding i) human or mouse CMKLR1, ii) a $SRE_{5x}$-Luc reporter gene, iii) a $G\alpha_{q5i66V}$ chimera, and iv) a β-galactosidase control. Twenty-four hours after transfection, cells were stimulated with increasing concentrations of various ligands for 15 minutes. Selected wells were then washed three times with serum-free media and plates were further incubated for 4 hours. Luciferase activity, determined as described in Experimental Procedures, was normalized relative to the maximal value observed using saturating concentrations of s-Stable Chem in cells that were unwashed (=100%). Representative results are shown in FIG. 5.

Lipidation of this peptide led to enhanced potency at both the human (FIG. 5A) and mouse (FIG. 5C) receptors. Furthermore, the activity of the lipidated stable peptide persisted despite washing whereas the activity of the soluble counterpart rapidly decreased when assessed at both the human (FIG. 5B) and mouse (FIG. 5D) receptors. Signaling by both s-Stable Chem and l-Stable Chem required expression of CMKLR1; no agonist activity was observed when cells were transfected with vector control (i.e. pcDNA1.1).

Example 6: l-Stable Chemerin Exhibits In Vivo Activity and is Anti-Inflammatory in an Experimental Model of Asthma Given the high potency, stability, and wash resistance of the lipidated stable chemerin analog, the anti-inflammatory activity of this compound in vivo was examined. Without wishing to be held to a particular theory, given the protective role of CMKLR1 in animal models of asthma, we hypothesized that l-Stable Chem could be a deliverable therapeutic that would potentially dampen the development of allergic airway inflammation. To test this hypothesis, we used an allergen sensitization and airway challenge model where mice were first sensitized with OVA followed by OVA aerosol challenge. In this model, l-Stable Chem was administered 30 min prior to each OVA aerosol challenge on days 14 and 17. Markers of inflammation were assessed at day 18 (time course: FIG. 6A).

As illustrated in FIG. 6, leukocyte numbers in bronchoalveolar lavage fluid were quantified. Notably, the number of eosinophils at Day 18 (FIG. 6D) was decreased in mice that had received l-Stable Chem, illustrating a protective effect of l-Stable Chem in this animal model of asthma. As shown in FIG. 6B, significant changes in airway epithelial mucus (versus DMSO control) were apparent in all treatment groups as determined by PAS staining at low magnification. The most pronounced attenuation of mucus metaplasia was seen in mice treated with l-Stable Chem. To further assess the effects of l-Stable Chem, the inflammatory response in the lung using H+E staining and BALF analysis of leukocytes was performed. Less leukocyte infiltration and fewer reactive bronchial epithelial cells in comparison to DMSO controls may be observed in FIG. 6C. In addition to showing that the lipidated peptide is active in vivo, these data also provide evidence of the anti-inflammatory potential of L-Stable Chem. The $EC_{50}$ of each tested lipidated chemerin analog is shown in Table 4 below:

TABLE 4

Half-maximal effective concentration ($EC_{50}$) for each CMKLR1 ligand with corresponding $pEC_{50}$.

| Ligand | Human CMKLR1 | | Mouse CMKLR1 | |
|---|---|---|---|---|
| | EC50 (nM) | pEC50 | EC50 (nM) | pEC50 |
| s-Chem 21-157 | 11.7 | 8.02 ± 0.19 | 13.7 | 8.01 ± 0.20 |
| s-Chem 149-157 | 139.3 | 6.85 ± 0.08 | 59.3 | 7.22 ± 0.07 |
| l-Chem 149-157 | 4.3 | 8.35 ± 0.10 | 4.0 | 8.38 ± 0.10 |
| s-Chem 149-157 + wash | N.D. | N.D. | N.D. | N.D. |
| l-Chem 149-157 + wash | 90.2 | 7.07 ± 0.13 | 42.9 | 7.39 ± 0.09 |

TABLE 4-continued

Half-maximal effective concentration ($EC_{50}$) for each CMKLR1 ligand with corresponding $pEC_{50}$.

| Ligand | Human CMKLR1 | | Mouse CMKLR1 | |
|---|---|---|---|---|
| | EC50 (nM) | pEC50 | EC50 (nM) | pEC50 |
| s-Stable Chem | 60.6 | 7.21 ± 0.08 | 11.9 | 7.92 ± 0.06 |
| l-Stable Chem | 2.6 | 8.59 ± 0.09 | 2.0 | 8.70 ± 0.09 |
| s-Stable Chem + wash | N.D. | N.D. | N.D. | N.D. |
| l-Stable Chem + wash | 27.1 | 7.60 ± 0.18 | 10.4 | 7.96 ± 0.16 | l-Stable Chemerin Decreases Mechanical and Cold Hypersensitivity in an Experimental Model of Neuropathic Pain: Comparison to Resolving E1 (RvE1)

It was also assessed whether treatment with l-Stable Chem would reduce nerve injury-induced neuropathic pain. These results were compared to RvE1 to determine if l-Stable Chem would provide a more protracted attenuation of pain responses. Chronic construction injury of the sciatic nerve produced robust mechanical allodynia as indicated by a reduction in paw withdrawal threshold in response to a series of von Frey hairs (FIGS. 7A+B) and an increase in paw withdrawal frequency in response to a specific low-threshold von Frey hair (0.16 g, FIG. 7C+D). CCI-induced neuropathic pain is also characterized by cold allodynia, a nociceptive response to acetone stimulation (FIG. 7E+F). These are cardinal features of neuropathic pain, elicited by normally innocuous stimuli. Notably, treatment with l-Stable Chem via spinal intrathecal route (100 pmol), 1 week following nerve injury when neuropathic pain is fully developed, significantly reduced established mechanical and cold allodynia for greater than 24 hours (FIGS. 7A, C, E). In comparison, the effects of RvE1 were only transient, with a significant decrease in pain scores observed only at the 1 hour time point (FIG. 7B,D,F).

All values represent the mean S.E.M. from at least three independent experiments, each performed in triplicate. Abbreviations: s-Chem 21-157 (soluble recombinant human chemerin corresponding to amino acids 21-157); s-Chem 149-157 (soluble C-terminal 9 amino acids of human chemerin); l-Chem 149-157 (lipidated C-terminal 9 amino acids of human chemerin); s-Stable Chem (soluble stable chemerin peptide; l-Stable Chem (lipidated stable chemerin peptide).

Example 7: Enhancement of Low Affinity Peptides to High Potency Anchored Ligands While anchored ligand entities, such as MTLs provide powerful in vitro and in vivo probes of receptor mediated activity, one limitation of MTLs is that they typically rely on delivery and expression of cDNA. The ability to optimize a construct using an MTL system and then deliver a corresponding lipidated version directly to target tissue as a soluble lipidated ligand agent would open a new range of possibilities for in vivo use.

As prototype ligands, this Example is focused on two peptides, Substance P (SubP) and Cholecystokinin 4 (CCK4), both well characterized neuroendocrine hormones that activate selected cognate receptor subtypes. SubP is an eleven amino acid peptide that activates 3 neurokinin receptor subtypes: NK1, NK2, and NK3. CCK4 is a tetrapeptide fragment of cholecystokinin that preferentially activates the cholecystokinin receptor subtype 2 (CCK2R) versus receptor subtype 1 (CCK1R). The processing of CCK and SubP are similar with each existing as a C terminal glycine extended pro-hormone. Following cleavage of the glycine residue, peptidylglycine α-amidating monooxygenase catalyzes the addition of a C-terminal amide group, thought to be important as both an affinity and efficacy determinant. During the course of initial pilot studies with these two peptides, it was observed that non-amidated SubP and glycine extended CCK4 both demonstrated significant agonist activity as MTLs (FIGS. 10 and 12). These reagents provided tools to systematically examine how the pharmacological features of low potency soluble peptides are altered with membrane anchoring. Therefore we compared recombinant MTLs with corresponding soluble lipidated ligand agents. Pharmacological features that were explored included receptor mediated activity, subtype specificity, and the susceptibility to inhibition by known antagonists of corresponding free peptides.

In this Example, non-amidated versions of SubP and CCK4 were examined in terms of their pharmacological properties as freely soluble peptides as compared to their anchored/lipidated counterparts. Unless otherwise described, the reagents and methods for this Example were as follows:

Cell Culture and Transfections

Human embryonic kidney cells (HEK293) were maintained at 37° C. in a humidified 5% $CO_2$ atmosphere and cultured with Dulbecco's modified eagle medium containing 10% fetal bovine serum, 100 U/mL penicillin, and 100 m/mL streptomycin. Cells were seeded into 96-well plates and grown to ~80% confluence. Cells were transfected for 24 hours using polyethylenimine in serum-free medium (Doyle et al., 2012) with cDNAs encoding, a) tethered ligand (where noted), b) 3 ng of indicated receptor, c) 25 ng of pGL4.33 a luciferase reporter gene under the control of a serum response element (Promega), and d) 5 ng of β-galactosidase to control for transfection efficiency.

Plasmids

Neurokinin receptors were purchased from the Missouri S+T cDNA Resource center. The CCK2 receptor was cloned as previously reported (Lee et al., The human brain cholecystokinin-B/gastrin receptor. Cloning and characterization, 1993, *J Biol Chem* 268:8164-8169); the CCK-1R cDNA was PCR amplified based on a published sequence (Pisegna et al., Molecular cloning, functional expression, and chromosomal localization of the human cholecystokinin type A receptor, 1994, *Ann N Y Acad Sci*713:338-342). Each receptor cDNA was subcloned into pcDNA1.1. Tethered SubP and CCK4 constructs were generated using a MTL with a type II transmembrane domain as a template cDNA which results in a free extracellular C-terminus of the corresponding peptide (FIG. 8, see Harwood et al., Membrane tethered bursicon constructs as heterodimeric modulators of the *Drosophila* G protein-coupled receptor rickets, 2013, *Mol Pharmacol* 83:814-821). Oligonucleotide-directed, site-specific mutagenesis was used to introduce sequences encoding the following peptides with a free carboxy terminus: SubP, RPKPQQFFGLM (SEQ ID NO.: 12) and CCK4, WMDF. For the glycine extended construct, the corresponding oligonucleotide encoded an additional glycine residue at the C-terminus of the CCK4 peptide (i.e. WMDFG (SEQ ID NO.: 13)). The nucleotide sequences of all receptor coding regions and tethered ligands were confirmed by automated DNA sequencing and analyzed using Vector NTI software (Invitrogen).

Peptides

Peptides illustrated in FIG. 9 were synthesized using the in-situ neutralization protocol for t-Boc chemistry (Schnolzer et al., In situ neutralization in Boc-chemistry solid phase peptide synthesis. Rapid, high yield assembly of difficult sequences, 1992, *International journal of peptide and protein research* 40:180-193) on PAM resin on a 0.5 mmol scale. Amino acids were used with the following side chain protecting groups: Arg(Tos), Asp(OBzl), Gln(Xan), Lys(Fmoc), Lys(2-Cl-Z) and Trp(For). Peptide coupling reactions were carried out with a 4-fold excess (2.0 mmol) of activated amino acid for at least 15 min. The t-Boc protecting group on the N-terminus was removed using trifluoroacetic acid (TFA). The PAM resin from the CCK4 peptide synthesis was split into two equal portions. One portion of the resin was used for synthesizing non-lipidated peptides. The CCK4 (s-CCK-Gly-COOH) peptide was left unmodified at the N-terminus. This peptide served as positive control for the lipidated counterparts.

The second portion of the CCK4 peptide and the SubP peptide were modified on resin as follows to yield test lipidated peptides (1-SubP-COOH and 1-CCK4-Gly-COOH). Spacers (these are AA's used between the peg linker and the peptide of interest) were introduced on the peptides before pegylation (KGG for SubP and GG for CCK4). The free N-terminus of the peptide on resin was first pegylated with N-Fmoc-PEG8-propionic acid using standard HBTU coupling conditions. The N-Fmoc protecting group was removed by treatment with 10% piperidine in DMF (N,N-Dimethylformamide) for 5 min. Palmitic acid was subsequently coupled with the N-terminal free amine of the pegylated peptide. Peptides were cleaved from the resin using high HF conditions with minor modifications to the usual procedure.

For the SubP peptide, longer times were used to ensure removal of Arg(Tos) protecting group (90% anhydrous HF/10% anisole at 0° C. for 2 h). For the CCK-4 peptides, 1,3-propanedithiol was used in the HF cleavage mixture to ensure deprotection of the formyl protecting group and prevent oxidation of methionine to its sulfoxide derivative: 85% anhydrous HF/10% anisole/5% PDT (1,3-propanedithiol) at 0° C. for 2 h) (Matsueda, 1982). Following cleavage from resin, peptides were precipitated with cold $Et_2O$. Unmodified peptides were extracted using 10% AcOH in water and the lipidated peptides were extracted using 10% AcOH in $H_2O$ followed by 10% AcOH in 50% $EtOH/H_2O$. Crude peptides were purified by RP-HPLC [Vydac C18, 10 ìm, 22 mm×250 mm]. The purities of the peptides were assessed by analytical RP-HPLC [Vydac C18, 5 ìm, 4 mm×250 mm].

The molar masses of peptides were determined by MALDI-TOF MS. The CCK4 peptide concentrations were determined using tryptophan absorbance (å=5580 $M^{-1} \cdot cm^{-1}$ at 278 nm) and concentration of the lipidated SubP peptide was measured using amino acid analysis performed at the Molecular Biology Core Facility at Dana-Farber Cancer Institute, Boston, Mass.

The lipidated SubP peptide (1-SubP-COOH) included a KGG spacer coupled to the N-terminus to allow attachment of the corresponding PEG8/palmitic acid. In comparison, the lipidated CCK4 analog (1-CCK-Gly-COOH) contains only a GG spacer used for subsequent anchoring. A general scheme of lipidated peptides is illustrated in FIG. 8B. Detailed chemical structures, purities, and molecular weights of the synthetic peptides are shown in FIG. 9.

Assessment of Ligand Activity

Tethered agonist induced signaling was assessed in HEK293 cells 24 hours after transfection. For soluble and lipidated peptides, 20 hours following transfection, cells were stimulated for an additional 4 hours. For antagonist assays, CP 99994 or YM022 (Tocris) were added concurrently with soluble agonist for 4 hours. With tethered ligands, antagonists were added 4 hours after transfection; activity was assessed following an additional 20 hour incubation. Quantification of luciferase and 3-galactosidase activities were performed as previously described (see Fortin et al., Discovery of dual-action membrane-anchored modulators of incretin receptors, 2011, *PLoS One*6:e24693). Data were analyzed by nonlinear curve fitting using Graph Pad Prism 5.0 software.

Results

This Example began with investigations focused on non-amidated SubP (SubP-COOH) as a recombinant MTL (tSubP). Activity of this construct was examined on each of the three human neurokinin receptor subtypes. When coexpressed with either NK1 or NK3 receptor, tSubP led to a concentration dependent increase in receptor mediated signaling (FIGS. 10A and C) whereas tSubP did not activate the NK2R (FIG. 10B). In contrast, as a freely soluble ligand, s-SubP-COOH activated only the NK1R. Efficacy/potency comparisons were then carried out using a corresponding soluble lipidated ligand agent, a SubP peptide with the addition of a PEG linker and a palmitic acid at the amino terminus, i.e. lipidated SubP-COOH (1-SubP-COOH).

This synthetic lipidated peptide mimicked the pharmacological activity of its genetically engineered tethered counterpart (tSubP). Both NK1 and NK3 receptors were activated by 1-SubP-COOH (FIGS. 10A and C). When assessed at the NK2R, no signaling was observed (FIG. 10B). Comparison of soluble and lipidated-SubP-COOH at the NK1R (FIG. 10A) revealed that the lipidated analog had enhanced potency; corresponding $EC_{50}$ values are as follows: l-SubP-COOH ($EC_{50}$=6.1 nM) and s-SubP-COOH ($EC_{50}$=443 nM). To further probe the pharmacological properties of anchored ligand induced receptor activation, we assessed the efficacy of a non-peptide inhibitor to block NK1R mediated signaling. CP 99994, a small molecule neurokinin receptor antagonist, inhibited signaling by freely soluble as well as anchored SubP, either as a recombinant MTL or a soluble lipidated ligand agent. As illustrated in FIG. 11A, tSubP activity was inhibited with an $IC_{50}$ of 69.5 nM. Agonist activity of l-SubP-COOH and s-SubP-COOH were also effectively blocked by CP 9994 (FIG. 11B) with $IC_{50}$ values of 18.0 nM and 6.7 nM, respectively.

In addition to studying how membrane anchoring influences SubP activity, this Example also focused on a second low affinity precursor peptide, glycine extended CCK4 (CCK4-Gly). Like SubP, the mature CCK4 peptide is also endogenously a amidated. $CCK4-NH_2$ is a well-established CCK2R ligand. In preliminary experiments, membrane tethered CCK4 (tCCK4), minimally activated CCK2R. In contrast to tCCK4, we noted that with addition of a C-terminal glycine residue (tCCK4-Gly), activity of this construct at the CCK2R significantly increased. As illustrated in FIG. 12A, tCCK4-Gly activated the CCK2R in a concentration dependent manner. In contrast, this construct showed no activity on the CCK1R (FIG. 12B).

To determine if the activity of the corresponding lipidated peptide would again (as with SubP) parallel the signaling observed with the tethered ligand, we next tested signaling induced by lipidated, glycine extended CCK4 (1-CCK4-Gly-COOH). As with tethered glycine extended CCK4,1-CCK4-Gly-COOH activated the CCK2R (FIG. 12A) and lacked activity at the CCK1R (FIG. 12B). Furthermore, lipidation of CCK4-Gly increased the potency of this ligand when compared with its soluble counterpart (s-CCK4-Gly-COOH) at the CCK2R. To further explore the mechanism underlying agonist mediated signaling, we evaluated the potential of a well-established CCK2R non-peptide antagonist, YM022, to block receptor activation. As illustrated in FIG. 13, YM022 inhibits CCK2 receptor signaling induced by tethered CCK4-Gly-COOH (FIG. 13A) as well as soluble and lipidated CCK4-Gly-COOH (FIG. 13B). $IC_{50}$ values were as follows: tCCK4-Gly ($IC_{50}$=0.54 nM), 1-CCK4-Gly-COOH ($IC_{50}$=10.2 nM), and s-CCK4-Gly-COOH ($IC_{50}$=0.84 nM).

As noted above, non-amidated SubP and glycine extended CCK4, respectively, showed activity when assessed as MTLs or soluble lipidated ligand agents (FIGS. 10 and 12). In light of the known importance of amidation for the function of SubP and CCK4, the activity of the non-amidated precursor peptides was not anticipated (see Cuttitta et al., Peptide amidation: signature of bioactivity, 1993, *Anat Rec* 236:87-93, 172-173; discussion 193-175; and Eipper et al., The biosynthesis of neuropeptides: peptide alpha-amidation, 1992, *Annu Rev Neurosci* 15:57-85). Without wishing to be held to a particular theory, these results suggest that tethered or lipidated precursor peptides may be active and that the requirement for post-translational modification does not necessarily preclude activity as an MTL or soluble lipidated ligand agent.

Example 8: Identification and Generation of a Soluble Lipidated Ligand Agent

This Example describes an exemplary embodiment of a provided method of identifying a candidate soluble lipidated ligand agent and generating said agent.

Initially, a candidate ligand entity is selected. As described herein, there is a wide range of potential ligand entities for use according to various embodiments. Examples include, but are not limited to, peptides, FDA-approved drugs, drugs under investigation for use on a particular membrane associated target, and investigational molecules shown to interact with one or more receptors, ion channels, enzymes, or transporters. In this Example, Chemerin is selected as the candidate ligand entity.

Once a candidate ligand entity (here, Chemerin) is selected, at least two versions of tethered forms of the ligand entity are created to associate with a target. In this Example, the target is CMKLR1. Both versions comprise a membrane tether, which in this Example is a transmembrane domain of either herpes simplex virus type 1, or tumor necrosis factor-α (TNFα). In this Example, the first version comprises Chemerin associated with a transmembrane domain derived from the herpes simplex virus type 1 as described in Fortin et al., Membrane-tethered ligands are effective probes for exploring class B1 G protein-coupled receptor function, 2009, PNAS, 106(19): 8049-8054, such that the N-terminus of Chemerin is free (i.e., projects freely into the extracellular space). The second version comprises Chemerin associated with the transmembrane domain of TNFα such that its C-terminus is free. In each case, a cDNA is created encoding both Chemerin and the appropriate transmembrane domain in the desired orientation.

Once the cDNAs have been made, each is transfected into a population of cells, for example, HEK293 cells. The activity of each MTL and/or MTP is assessed using one or more target-specific assays. Several luciferase-based assays have been described previously that are compatible with this example (as well as to assess signaling through other receptor/membrane targets), including those found in Al-Fulaij et al., Pharmacological analysis of human D1 and D2 dopamine receptor missense variants, 2008, *J. Mol. Neurosci*, 34:211-223; Fortin et al., The mu-opioid receptor variant N190K is unresponsive to peptide agonists yet can be rescued by small-molecule drugs, 2010, *Mol. Pharmacol*, 78: 837-845; Kopin et al., Identification of a series of CCK-2 receptor nonpeptide agonists: sensitivity to stereochemistry and a receptor point mutation, 2003, *Proc Natl Acad Sci USA*, 100: 5525-5530; Fortin et al., Discovery of Dual-Action Membrane-Anchored Modulators of Incretin Receptors, *PLoS One* 2011, 6; Harwood et al., Membrane Tethered Bursicon Constructs as Heterodimeric Modulators of the *Drosophila* G Protein-Coupled Receptor Rickets, *Mol. Pharm.*, 2013, 83:814-821; Fortin et al., Membrane-Tethered Ligands are Effective Probes for Exploring Class B1 G Protein-Coupled Receptor Function, *Proc. Natl. Acad Sci.*, 2009, 106: 8049-8054; Conklin et al., Substitution of three amino acids switches receptor specificity of Gq alpha to that of Gi alpha, 1993, *Nature*, 363: 274-276; Fan et al., Using luciferase assays to study G protein-coupled receptor pathways and a screen for GPCR modulators, 2005, *Cell notes*, 13; and Chang et al., Luciferase reporter assay system for deciphering GPCR pathways, 2010, *Curr Chem Genomics*, 4:84-91.

In this Example, HEK293 cells are transfected with: a) a cDNA encoding CMKLR1, b) cDNA encoding one of the two chemerin-TMD constructs, c) a cDNA encoding G$\alpha$q5i to assess G$\alpha$i signaling, a known downstream effect of CMKLR1 stimulation by chemerin, and d) an SRE-luciferase reporter gene (to assess G$\alpha$i signaling). Once the above reagents are introduced to the cells, expression of the cDNAs is initiated and the level of luciferase activity is recorded. In the assays of this Example, increased observed luciferase activity correlates to increased chemerin activity, and increased chemerin activity indicates that a particular construct is an attractive candidate for development as a soluble lipidated ligand agent.

The most promising construct(s) (e.g., short, active and/or protease-resistant) are then selected for development as soluble lipidated ligand agents. In order to develop a soluble lipidated ligand agent from an MTL/MTP, the ligand entity, in the most desirable or advantageous orientation, is associated with a lipid entity, in some embodiments, with the use of a linker. In this Example, the linker used is polyethylene glycol (PEG), specifically PEG8 and the lipid entity used is palmitic acid. In various embodiments, a variety of linkers and/or lipid entities may be used in order to determine the most desirable combinations for use in creating one or more soluble lipidated ligand agents.

The candidate soluble lipidated ligand agents, here chemerin-PEG$_8$-palmitic acid agents, are then tested in an assay similar to the luciferase assay described above. However, since soluble lipidated ligand agents are not capable of expression from a cDNA, they must be added to the test system exogenously. Other components of the system, such as the target and luciferase reporter, may be introduced via cDNA transfection as described previously and above. The activity of the candidate soluble lipidated ligand agent is then assessed in a manner similar to the MTL/MTP. Comparison is made between the SMAL and a non-lipidated and/or non-tethered forms of the ligand entity (peptide alone, peptide plus linker vs. SMAL).

Once one or more candidate soluble lipidated ligand agents has been identified, it may be desirable to optimize the agent. While any of a variety of optimizations may be used, one exemplary optimization is the enhancement of stability such as through the introduction of one or more D-amino acids, Once one or more optimizations have been performed, the activity of the optimized agent will typically be reassessed. (peptide alone, peptide plus linker and SMAL with original peptide vs. modified peptide alone, modified peptide plus linker and SMAL including modified peptide).

While a very basic method and limited test constructs are described in this Example, many permutations of the above process are possible. For example, it is possible, using provided methods and constructs, to test a wide variety of potential ligand entities including ligand entities that have been modified in some way from their natural form (e.g., via the introduction of one or more non-natural amino acids in a peptidic ligand entity and/or varying the length and/or sequence of the peptidic ligand entity). In addition, it will often be desirable to test a variety of linkers and/or lipid entities when designing candidate soluble lipidated ligand agents. Further, it may be desirable to use more than a single test of activity and/or efficacy for a particular ligand entity and/or soluble lipidated ligand agent. This Example is intended merely to illustrate a particular embodiment of certain provided methods.

Those skilled in the art will recognize, or be able to ascertain using no more than routine experimentation, many equivalents to the specific embodiments of the invention described herein. The scope of the present invention is not intended to be limited to the above Description, but rather as set forth in the following claims.

The invention claimed is:

1. A method of treating neuropathic pain, the method comprising administering to a subject in need thereof a soluble lipidated ligand agent that has the following structure:

(SEQ ID NO.: 11)

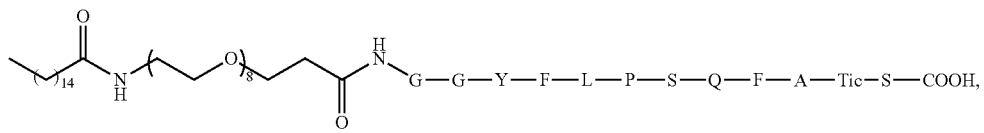

wherein one or more of the Y, S, and A are D-amino acids, and wherein $T_1c$ represents (S)-1,2,3,4-tetrahydroisoquinoline-3-carboxylic acid.

2. The method of claim 1, wherein the soluble lipidated ligand agent is formulated as a pharmaceutical composition comprising the soluble lipidated ligand agent and a pharmaceutically acceptable carrier.

3. The method of claim 1, wherein the soluble lipidated ligand agent is administered at an effective dose at an administration interval such that at least one symptom or feature of neuropathic pain is reduced in intensity, severity, duration, or frequency or has delayed onset.

4. The method of claim 1, wherein the soluble lipidated ligand entity is administered daily, twice a week, once a week, once every two weeks, once every three weeks, once a month, or at a variable interval.

5. The method of claim 1, wherein the soluble lipidated ligand entity is administered intravenously, intradermally, intra-articularly, transdermally, orally, by inhalation, subcutaneously, topically, and/or transmucosally.

* * * * *

UNITED STATES PATENT AND TRADEMARK OFFICE
CERTIFICATE OF CORRECTION

PATENT NO. : 11,254,720 B2  
APPLICATION NO. : 16/245472  
DATED : February 22, 2022  
INVENTOR(S) : Cohen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 239 days.

Signed and Sealed this  
Twenty-ninth Day of November, 2022

Katherine Kelly Vidal  
*Director of the United States Patent and Trademark Office*